(12) United States Patent
Iida et al.

(10) Patent No.: US 10,781,461 B2
(45) Date of Patent: Sep. 22, 2020

(54) USEFUL MICROORGANISM AND METHOD FOR PRODUCING SUBSTANCE OF INTEREST

(71) Applicant: Kao Corporation, Tokyo (JP)

(72) Inventors: Kougo Iida, Kanagawa (JP); Takumi Iwasaki, Kanagawa (JP); Tatsunari Nishi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/034,532

(22) Filed: Jul. 13, 2018

(65) Prior Publication Data

US 2018/0312882 A1 Nov. 1, 2018

Related U.S. Application Data

(63) Continuation of application No. 14/408,400, filed as application No. PCT/JP2013/068205 on Jul. 3, 2013, now Pat. No. 10,047,382.

(30) Foreign Application Priority Data

Jul. 3, 2012 (JP) ................................ 2012-149431

(51) Int. Cl.
| | |
|---|---|
| *C12P 7/42* | (2006.01) |
| *C12N 15/52* | (2006.01) |
| *C12P 7/40* | (2006.01) |
| *C12P 7/44* | (2006.01) |
| *C12N 1/20* | (2006.01) |
| *C12P 13/06* | (2006.01) |
| *C12P 13/14* | (2006.01) |
| *C12P 13/20* | (2006.01) |
| *C12N 9/10* | (2006.01) |

(52) U.S. Cl.
CPC .................. *C12P 7/42* (2013.01); *C12N 1/20* (2013.01); *C12N 9/1055* (2013.01); *C12N 15/52* (2013.01); *C12P 7/40* (2013.01); *C12P 7/44* (2013.01); *C12P 13/06* (2013.01); *C12P 13/14* (2013.01); *C12P 13/20* (2013.01)

(58) Field of Classification Search
None
See application file for complete search history.

(56) References Cited

U.S. PATENT DOCUMENTS

| | | | |
|---|---|---|---|
| 5,272,073 A | 12/1993 | Frost et al. | |
| 5,821,266 A | 10/1998 | Frost | |
| 6,472,169 B1 | 10/2002 | Frost et al. | |
| 7,666,655 B2 | 2/2010 | Vitushkina et al. | |
| 7,935,506 B2 | 5/2011 | Vitushkina et al. | |
| 10,047,382 B2* | 8/2018 | Iida ..................... | C12N 9/1055 |
| 2002/0192746 A1 | 12/2002 | Takano et al. | |
| 2004/0259212 A1 | 12/2004 | Takano et al. | |
| 2005/0202544 A1 | 9/2005 | Retallack et al. | |
| 2006/0172423 A1 | 8/2006 | Van Der Geize et al. | |
| 2010/0068773 A1 | 3/2010 | Marx et al. | |
| 2010/0291644 A1 | 11/2010 | Marx et al. | |
| 2011/0039313 A1 | 2/2011 | Verseck et al. | |
| 2013/0310458 A1 | 11/2013 | Eggeling et al. | |
| 2015/0197775 A1 | 7/2015 | Iida et al. | |
| 2015/0218601 A1 | 8/2015 | Marx et al. | |

FOREIGN PATENT DOCUMENTS

| | | |
|---|---|---|
| CN | 102498086 A | 6/2012 |
| JP | 45-039036 | 12/1970 |
| JP | 50-89592 | 7/1975 |
| JP | 58-067699 | 4/1983 |
| JP | 58-077895 | 5/1983 |
| JP | 60-098989 | 6/1985 |
| JP | 5-049489 | 3/1993 |
| JP | 5-304971 | 11/1993 |
| JP | 08-504561 A | 5/1996 |
| JP | 10-509317 A | 9/1998 |
| JP | 2000-295996 | 10/2000 |
| JP | 2006-506049 A | 2/2006 |
| JP | 2006-508684 | 3/2006 |
| JP | 2007-300809 | 11/2007 |
| JP | P4305184 | 7/2009 |
| JP | 2010-517519 A | 5/2010 |

(Continued)

OTHER PUBLICATIONS

Cohen et al., "Nonchromosomal Antibiotic Resistance in Bacteria: Genetic Transformation of *Escherichia coli* by R-Factor DNA", *Proc. Nat. Acad. Sci. USA*, vol. 69, No. 8, pp. 2110-2114, Aug. 1972.

Ikeda et al., "Hyperproduction of Tryptophan by *Corynebacterium glutamicum* with the Modified Pentose Phosphate Pathway", *Appl. Environ. Microbial.*, vol. 65, No. 6, pp. 2497-2502, 1999.

Sanger et al., "DNA sequencing with chain-terminating inhibitors", *Proc. Nat!. Acad. Sci. USA*, vol. 74, No. 12, pp. 5463-5467, 1977.

Li et al., "Microbial Synthesis of 3-Dehydroshikimic Acid: A Comparative Analysis of D-Xylose, L-Arabinose, and D-Glucose Carbon Sources.", *Biotechnol. Frog.*, vol. 15, No. 5, pp. 876-883, 1999.

Ll, "Benzene-Free Synthesis of Catechol: Interfacing Microbial and Chemical Catalysis", *J. Am. Chern. Soc.*, vol. 127,pp. 2874-2882,2005.

(Continued)

*Primary Examiner* — Iqbal H Chowdhury
(74) *Attorney, Agent, or Firm* — Sterne, Kessler, Goldstein & Fox P.L.L.C.

(57) ABSTRACT

It is an object of the present invention to provide a bacterial strain that can decrease the amount of an intermediate Compound P converted into Metabolite M and efficiently accumulate Compound P in a medium that is not supplemented with Metabolite M or the final product generated from Metabolite M. The present invention provides a prokaryotic organism having all features (a) to (d) as defined in the specification so as to accumulate Compound P by regulating expression level of Enzyme X that converts Compound P as an intermediate metabolite into Metabolite M in a biosynthetic pathway in which Metabolite M indispensable for the growth is produced from a carbon source.

9 Claims, 5 Drawing Sheets

Specification includes a Sequence Listing.

(56) References Cited

FOREIGN PATENT DOCUMENTS

| | | |
|---|---|---|
| JP | 2010-528597 A | 8/2010 |
| JP | 2010-207094 | 9/2010 |
| WO | WO 93/22348 A1 | 11/1993 |
| WO | WO 96/14413 A1 | 5/1996 |
| WO | WO 2007/074991 A1 | 7/2007 |
| WO | WO 2010/085712 A2 | 7/2010 |
| WO | WO 2011/138006 A1 | 11/2011 |

OTHER PUBLICATIONS

Yanisch-Perron et al., "Improved M13 Phage Cloning Vectors and Host Strains: Nucleotide Sequences of the M13mp18 and pUC19 Vectors", *Gene*, vol. 33, pp. 103-119, 1985.

Van der Rest et al., "A Heat Shock Following Electroporation Induces Highly Efficient Transformation of *Corynebacterium glutamicum* with Xenogeneic Plasmid DNA", *Appl. Microbial. Biotechnol.*, vol. 52, pp. 541-545, 1999.

Chandran et al., "Phosphoenolpyruvate Availability and the Biosynthesis of Shikimic Acid", *Biotechnol. Prog.*, vol. 19, pp. 808-814, 2003.

Jäger et al., "Expression of the *Bacillus subtilis* sacB gene Leads to Sucrose Sensitivity in the Gram-positive Bacterium *Corynebacterium glutamicum* but not in *Streptomyces lividans*", *J. Bacterial.*, vol. 174, No. 16, pp. 5462-5465, 1992.

Li, "Fed-Batch Fermentor Synthesis of 3-Dehydroshikimic Acid Using Recombinant *Escherichia coli*", *Biotechnol. Bioeng.*, vol. 64, pp. 61-73, 1999.

Hagino et al., "L-Tyrosine Production by Analog-resistant Mutants Derived from a Phenylalanine Auxotroph of *Corynebacterium glutamicum*", *Agr. Biol. Chern*, vol. 37, No. 9, pp. 2013-2023, 1973.

Hagino et al., "L-Tryptophan Production by Analog-resistant Mutants Derived from a Phenylalanine and Tyrosine Double Auxotroph of *Corynebacterium glutamicum*", *Agr. Biol. Chern.*, vol. 39, No. 2, pp. 343-349, 1975.

Morawski et al., "Repression of *Acinetobacter* Vanillate Demethylase Synthesis by VanR, a Member of the GntR Family of Transcriptional Regulators,", *FEMS Microbial. Lett.*, vol. 187, pp. 65-68, 2000.

Teramoto et al., "Regulation of Expression of Genes Involved in Quinate and Shikimate Utilization in *Corynebacterium glutamicum*,"*Appl. Environ. Microbial.*, vol. 75, No. 11, pp. 3461-3468, 2009.

Dower et al., "High Efficiency Transformation of *E. coli* by High Voltage Eletroporation", *Nucleic Acids Research*, vol. 16, No. 13, pp. 6127-6145, 1988.

International Search Report for PCT/JP2013/068205, dated Oct. 8, 2013, along with an English language translation.

International Preliminary Report on Patentability for PCT/JP2013/068205, dated Jan. 15, 2015, along with an English language translation.

Ikeda, "Towards Bacterial Strains Overproducing L-Tryptophan and Other Aromatics by Metabolic Engineering", *Applied Microbiology and Biotechnology9*, vol. 69, No. 6, pp. 615-626, 2006.

Bongaerts et al., "Metabolic Engineering for Microbial Production of Aromatic Amino Acids and Derived Compounds", *Metabolic Engineering*, vol. 3, pp. 289-300, 2001.

Yi et al., "Altered Glucose Transport and Shikimate Pathway Product Yields in *E. coli*", *Biotechnology Progress*, vol. 19, No. 5, pp. 1450-1459, 2003.

Yi et al., "Modulation of Phosphoenolpyruvate Synthase Expression Increases Shikimate Pathway Product Yields in *E. coli*" *Biotechnology Progress*, vol. 18, No. 6, pp. 1141-1148, 2002.

Bentley, "The Shikimate Pathway—A Metabolic Tree with Many Branches", *Critical Reviews in Biochemistry and Molecular Biology*, vol. 25, No. 5, pp. 307-384, 1990.

Adachi et al., "Enzymatic Preparation of Metabolic Intermediates, 3-Dehydroquinate and 3-Dehydroshikimate, in the Shikimate Pathway", *Bioscience Biotechnology Biochemistry*, vol. 70, No. 12, pp. 3081-3083, 2006.

Extended European Search Report issued in EP Patent Application No. 13812517.4, dated Oct. 23, 2015.

Japanese Notification of Reasons for Refusal issued with respect to JP Application No. 2014-523757, dated Feb. 7, 2017, along with an English Machine Translation.

Li et al., "Synthesis of vanillin from glucose," *J. Am. Chem. Soc.* 1998, 120: 10545-10546.

Tropel et al., "Bacterial Transcriptional Regulators for Degradation Pathways of Aromatic Compounds," *Microbiology and Molecular Biology Reviews*, Sep. 2004, 68(3), p. 474-500.

Guo et al., "PcaR-mediated activation and repression of pca genes from Pseudomonas putida are propagated by its binding to both the −35 and the −10 promoter elements," *Molecular Microbiology* (1999) 32(2), 253-263.

\* cited by examiner

USEFUL MICROORGANISM AND METHOD FOR PRODUCING SUBSTANCE OF INTEREST

TECHNICAL FIELD

The present invention relates to microorganisms used for efficient production of useful substances, such as organic acids or amino acids, and a method for producing useful substances using such microorganisms.

BACKGROUND ART

Techniques for obtaining microorganisms that can efficiently produce useful compounds, such as organic acids, amino acids, nucleic acids, or vitamins, through, for example, introduction of auxotrophic mutation or metabotropic mutation or the recombinant DNA technology have been developed. As shown in FIG. 1, a method for obtaining auxotrophs in which activity of Enzyme X for converting Compound P into Metabolite M has been deleted had been often employed in order to efficiently produce Compound P in a biosynthetic pathway or a metabolic pathway in which Metabolite M indispensable for the growth is generated from a carbon source through Compound P as an intermediate metabolite. When Compound P of interest is to be produced with such mutant, however, the addition of Metabolite M or the final product generated from Metabolite M to a medium was necessary, and the production cost was disadvantageously increased.

For example, it has been reported that shikimic acid as an intermediate metabolite in the shikimic acid pathway shown in FIG. 2 can be efficiently produced with the use of *Escherichia coli* in which shikimate kinase activity had been deleted (Patent Document 1 and Non-Patent Document 1). When the microorganisms were used, however, parahydroxybenzoic acid auxotrophy, p-aminobenzoic acid auxotrophy, and 2,3-dihydroxybenzoic acid auxotrophy were developed in addition to tryptophan auxotrophy, tyrosine auxotrophy, and phenylalanine auxotrophy. This necessitated the addition of these 6 types of compounds to the medium. While it has been reported that 3-dehydroshikimic acid as an intermediate metabolite in the shikimic acid pathway could be efficiently produced with the use of *Escherichia coli* in which shikimate dehydrogenase activity had been deleted, disadvantageously, such microorganisms would also require the above 6 types of compounds (Patent Document 2 and Non-Patent Document 2).

Through the introduction of mutations by means of, for example, treatment with mutagens, such as N-methyl-N'-nitro-N-nitrosoguanidine or ethyl methanesulfonate, UV or radiation application, or spontaneous mutation, a mutation for decreasing the amount of Enzyme X that converts Compound P into Metabolite M may be introduced so as to decrease the amount of Metabolite M produced. Thus, the amount of Compound P may be increased. In such a case, activity of Enzyme X remains, and a part of Compound P is constantly converted into Metabolite M as a consequence. Accordingly, conditions for maximizing the amount of Compound P produced are not easily determined.

The present invention discloses a method for efficiently producing Compound P without the addition of Metabolite M or the final product generated from Metabolite M to a medium by allowing a repressor to artificially direct the transcription of the gene x encoding Enzyme X, so as to regulate the amount of Metabolite M produced. However, no case has been reported in which the productivity of Compound P had been improved by regulating the transcription of the gene x with the use of another promoter, the transcription therefrom is repressed by a repressor, instead of the promoter native to the gene x.

When producing useful compounds with the use of microorganisms, useful compounds are often produced through a pathway branched from Compound P in a biosynthetic pathway or a metabolic pathway in which Metabolite M indispensable for the growth is generated from a carbon source through Compound P as an intermediate metabolite. In such a case, a method for obtaining auxotrophs in which Enzyme X activity had been deleted had been often employed. Such technique, however, required the addition of Metabolite M or the final product generated from Metabolite M to a medium, and the production cost would be disadvantageously increased.

Concerning the production of target substances with the use of the shikimic acid pathway having many branched pathways (FIG. 2), for example, many tryptophan-producing strains are known to have tyrosine and phenylalanine auxotrophy so as to prevent chorismic acid, as an intermediate metabolite, from entering into a tyrosine or phenylalanine synthetic pathway (Patent Document 3 and Non-Patent Documents 3 and 4). Also, phenylalanine-producing strains are known to have tyrosine auxotrophy (Patent Documents 4 and 5 and Non-Patent Document 5). When producing an aromatic amino acid of interest, accordingly, it is necessary to add another type of aromatic amino acid to a medium.

It is also reported that about 40 g/L protocatechuic acid can be produced by creating a mutant in which an enzyme that converts 3-dehydroshikimic acid (hereafter abbreviated to as "DHS") into shikimic acid (i.e., Metabolite M) has been deleted and the amount of 3-deoxy-D-arabino-heptulosonate-7-phosphate (hereafter abbreviated to as "DAHP") as a starting material in the shikimic acid pathway has been increased (Non-Patent Document 6). When such mutant is used, however, in addition to tryptophan auxotrophy, tyrosine auxotrophy, and phenylalanine auxotrophy, p-hydroxybenzoic acid auxotrophy, p-aminobenzoic acid auxotrophy, and 2,3-dihydroxybenzoic acid auxotrophy are developed. Accordingly, the addition of these 6 types of compounds to a medium would be required, disadvantageously. In addition, protocatechuic acid-producing strains have been attained by introducing a mutation into bacteria of *Corynebacterium* (Patent Document 6) or *Brevibacterium* (Patent Documents 7 and 8). Such strain requires nutritional sources, such as tyrosine, in order to produce protocatechuic acid. Further, the maximal amount of protocatechuic acid produced by such mutant is about 13 g/L, and such amount is less than the amount produced by an aromatic amino acid auxotroph (Patent Document 8).

PRIOR ART DOCUMENTS

Patent Documents

Patent Document 1: U.S. Pat. No. 6,472,169
Patent Document 2: U.S. Pat. No. 5,821,266
Patent Document 3: JP Patent 4,305,184
Patent Document 4: JP H05-49489 A (1993)
Patent Document 5: JP H05-304971 A (1993)
Patent Document 6: JP S45-39036 B (1970)
Patent Document 7: JP S50-89592 A (1975)
Patent Document 8: JP S60-98989 A (1985)

Non-Patent Documents

Non-Patent Document 1: Biotechnol. Prog., 19, 808, 2003
Non-Patent Document 2: Biotechol. Bioeng., 64, 61, 1999

Non-Patent Document 3: Agric. Biol. Chem., 39, 343, 1975
Non-Patent Document 4: Appl. Environ. Microbiol., 65, 2497, 1999
Non-Patent Document 5: Agric. Biol. Chem., 37, 2013, 1973
Non-Patent Document 6: J. Am. Chem. Soc., 127, 2874, 2005

SUMMARY OF THE INVENTION

Objects to be Attained by the Invention

It is an object of the present invention to provide a method for obtaining a bacterial strain that can decrease the amount of Compound P converted into Metabolite M and efficiently accumulate Compound P in a medium that is not supplemented with Metabolite M or the final product generated from Metabolite M when producing Compound P with the use of a microorganism having a biosynthetic pathway or a metabolic pathway in which Metabolite M indispensable for the growth is generated from a carbon source through Compound P as an intermediate metabolite (FIG. 1). It is another object to provide a method for producing Compound Q from the accumulated Compound P with the aid of Enzyme Y (FIG. 3).

Means for Attaining the Objects

The present inventors had attempted to attain the above objects through studies aimed at production of a bacterial strain that can efficiently produce a target substance (i.e., DHS) from the *Corynebacterium glutamicum* ATCC13032 strain (hereafter abbreviated to as the "ATCC13032 strain"). At the outset, they produced the NSHΔaroE3 strain by introducing a deletion mutation into the aroE3 (cg1835) gene that encodes shikimate dehydrogenase (Enzyme X) accelerating conversion of DHS into shikimic acid (Metabolite M) from the NSH strain in which expression of a plurality of enzymes associated with the biosynthetic pathway from glucose to DHS (Compound P) has been increased and transcription of the qsuB (cg0502) gene encoding the DHS dehydratase (Enzyme Y) accelerating conversion of DHS into protocatechuic acid is directed by the tuf (cg0587) gene promoter (hereafter abbreviated to as the "Tu promoter"). As a result, they confirmed that the growth rate of the NSHΔaroE3 strain would be significantly decreased without the addition of 3 types of aromatic amino acids (i.e., tryptophan, phenylalanine, and tyrosine). They also confirmed that this NSHΔaroE3 strain would produce 0.5 g/L protocatechuic acid via culture thereof in a medium supplemented with the 3 types of aromatic amino acids and shikimic acid. In order to regulate the expression of the active shikimate dehydrogenase gene (the aroE3 gene) by a repressor encoded by the vanR (cg2615) gene (hereafter abbreviated to as "VanR repressor"), subsequently, the NSHΔaroE3_vanE3 strain was produced from the NSHΔaroE3 strain by incorporating DNA comprising the aroE3 gene ligated to the vanA (cg2616) gene promoter (hereafter abbreviated to as "vanA promoter") into the chromosome. The present inventors discovered that the NSHΔaroE3_vanE3 strain could grow in a synthetic medium that is not supplemented with the 3 types of aromatic amino acids and shikimic acid and such strain would produce 16.6 g/L protocatechuic acid. This has led to the completion of the present invention. In addition, they produced a strain in which aroE3 gene expression is regulated by a repressor encoded by the rhcR (cg1308) gene (hereafter abbreviated to as "RhcR repressor") from the NSHΔaroE3 strain. As a result, productivity of protocatechuic acid at 11.2 g/L was observed, and they discovered that excellent protocatechuic acid productivity could be achieved with the use of a repressor other than the VanR repressor.

In addition to a deletion mutation of the aroE3 gene in the NSHΔaroE3 strain, subsequently, the NSHΔaroE3ΔqsuBΔqsuD strain was produced by introducing deletion mutations into the qsuD (cg0504) gene encoding shikimate dehydrogenase that would accelerate conversion of DHS into shikimic acid (Metabolite M) and the qsuB gene encoding DHS dehydratase. As a result, they confirmed that the NSHΔaroE3ΔqsuBΔqsuD strain would not grow without the addition of the 3 types of aromatic amino acids, vitamin K2, and p-aminobenzoic acid. They also confirmed that this NSHΔaroE3ΔqsuBΔqsuD strain would produce 7.7 g/L DHS via culture thereof in a medium supplemented with the additives described above. In the same manner as in the case of production of the NSHΔaroE3ΔqsuBΔqsuD strain, the NSHΔaroE3_vanE3ΔqsuBΔqsuD strain was produced from the NSHΔaroE3_vanE3 strain by introducing deletion mutations into the qsuD gene and the qsuB gene, and the Pben-vanR strain was produced from the NSHΔaroE3_vanE3ΔqsuBΔqsuD strain by incorporating DNA comprising the benA (cg2637) gene promoter ligated to the vanR gene that encodes the VanR repressor into the chromosome. As a result, they discovered that the Pben-vanR strain could grow in a synthetic medium that is not supplemented with the additives and such strain would produce 15.4 g/L DHS. This has led to the completion of the present invention.

The present invention relates to (1) to (24) below.

(1) A prokaryotic organism having all features (a) to (d) below so as to accumulate Compound P by regulating expression level of Enzyme X that converts Compound P as an intermediate metabolite into Metabolite M in a biosynthetic pathway in which Metabolite M indispensable for the growth is produced from a carbon source:

(a) activity of one or more enzymes selected from among enzymes associated with biosynthesis of Compound P from a carbon source that can be used by the prokaryotic organism is enhanced compared with that of a wild-type prokaryotic organism;

(b) activity of Enzyme X is lost or reduced by a mutation of substitution, deletion, or insertion of one or more nucleotides in a translation region of a wild-type gene x encoding a protein of Enzyme X, a translation regulatory region of the gene, or a promoter region that accelerates the transcription of the gene x;

(c) transcription of DNA encoding active Enzyme X is regulated by Promoter A, which is different from a native promoter that accelerates the transcription of the gene x and wherein the transcription is repressed with the aid of a Repressor R protein; and (d) transcription of one or more copies of the gene z encoding a Repressor R protein is regulated by the promoter native to the gene and/or an inducible Promoter B that is different from the native promoter.

(2) The prokaryotic organism according to (1), wherein the mutation of substitution in a promoter region that accelerates the transcription of the gene x as defined in the feature (b) is a mutation of substitution of the entire or a part of the promoter region with DNA of the Promoter A as defined in the feature (c).

(3) The prokaryotic organism according to (1) or (2), wherein activity of one or more metabolic enzymes other than Enzyme X among the enzymes of the prokaryotic organism that metabolize Compound P is lost or reduced.

(4) The prokaryotic organism according to any one of (1) to (3), wherein Promoter B is induced with the addition of a compound selected from the group consisting of ferulic acid, vanillic acid, vanillin, benzoic acid, 3-hydroxybenzoic acid, resorcinol, 4-hydroxybenzoic acid, 2,4-dihydroxybenzoic acid, fructose, and sucrose.

(5) The prokaryotic organism according to any one of (1) to (4), wherein the gene z encoding a Repressor R protein is the vanR (cg2615) gene, the pcaR (cg2624) gene, or the rhcR (cg1308) gene of the *Corynebacterium glutamicum* ATCC13032 strain.

(6) The prokaryotic organism according to any one of (1) to (5), wherein Promoter A is a vanA (cg2616) gene promoter, a pobA (cg1226) gene promoter, a pcaH (cg2631) gene promoter, or a rhcH (cg1309) gene promoter of the *Corynebacterium glutamicum* ATCC13032 strain.

(7) A method for producing Compound P comprising culturing the prokaryotic organism according to any one of (1) to (6) while repressing Promoter A transcription in the presence of a carbon source.

(8) A method for producing Compound P comprising culturing the prokaryotic organism according to any one of (1) to (6) while repressing Promoter A transcription in the presence of a carbon source, and inducing Promoter B transcription to increase the expression level of the Repressor R protein, thereby decreasing the amount of Metabolite M produced.

(9) A method for producing Compound P comprising culturing the prokaryotic organism according to any one of (1) to (6) while derepressing Promoter A transcription in the presence of a carbon source, and inducing Promoter B transcription to increase the expression level of the Repressor R protein, thereby decreasing the amount of Metabolite M produced.

(10) The method for producing Compound P according to any one of (7) to (9), wherein a combination of Compound P and Metabolite M is any of combinations (f) to (i) below:

(f) Compound P is 3-dehydroshikimic acid and Metabolite M is shikimic acid;

(g) Compound P is glutamic acid and Metabolite M is N-acetylglutamate or γ-glutamyl phosphate;

(h) Compound P is aspartic acid and Metabolite M is β-aspartyl phosphate; and (i) Compound P is serine and Metabolite M is glycine.

(11) The prokaryotic organism according to any one of (1) to (6) having the feature (e) below in addition to the features (a) to (d), so as to convert the accumulated Compound P into Compound Q with the aid of Enzyme Y:

(e) the capacity for converting Compound P into Compound Q is enhanced or gene y expression is regulated differently from a wild-type gene because of a mutation of substitution, deletion, or addition of one or more nucleotides in a translation region of the gene y encoding a protein of Enzyme Y, a translation regulatory region of the gene, or a promoter region that accelerates the transcription of the gene y.

(12) The prokaryotic organism according to (11), wherein activity of one or more metabolic enzymes among the enzymes of the prokaryotic organism that metabolize Compound Q is lost or reduced.

(13) The prokaryotic organism according to (11) or (12), wherein the mutation of substitution in a promoter region that accelerates the transcription of the gene y as defined in the feature (e) is a mutation of substitution of the entire or a part of the promoter region with DNA of the Promoter C that is different from the native promoter that accelerates the gene transcription or Promoter A.

(14) The prokaryotic organism according to (13), wherein Promoter C is the same as Promoter B or Promoter C transcription is regulated by a protein that regulates Protein B transcription.

(15) The prokaryotic organism according to (13) or (14), wherein Promoter C is an inducible promoter.

(16) The prokaryotic organism according to (15), wherein Promoter C is induced with the addition of a compound selected from the group consisting of ferulic acid, vanillic acid, vanillin, benzoic acid, 3-hydroxybenzoic acid, resorcinol, 4-hydroxybenzoic acid, 2,4-dihydroxybenzoic acid, fructose, and sucrose.

(17) A method for producing Compound Q comprising culturing the prokaryotic organism according to any one of (11) to (16) while repressing Promoter A transcription in the presence of a carbon source.

(18) A method for producing Compound Q comprising culturing the prokaryotic organism according to any one of (11) to (16) while repressing Promoter A transcription in the presence of a carbon source, and inducing Promoter B transcription to increase the expression level of the Repressor R protein, thereby decreasing the amount of Metabolite M produced and increasing the amount of Compound Q produced.

(19) A method for producing Compound Q comprising culturing the prokaryotic organism according to any one of (11) to (16) while derepressing Promoter A transcription in the presence of a carbon source, and inducing Promoter B transcription to increase the expression level of the Repressor R protein, thereby decreasing the amount of Metabolite M produced and increasing the amount of Compound Q produced.

(20) The method for producing Compound Q according to any one of (17) to (19) comprising culturing the prokaryotic organism according to any one of (11) to (16) in the presence of a carbon source and then inducing transcription of Promoter C to increase the Enzyme Y expression level, thereby increasing the amount of Compound Q produced.

(21) The method for producing Compound Q according to any one of (17) to (20), wherein a combination of Compound P, Compound Q, and Metabolite M is any of combinations (j) to (w) below:

(j) Compound P is 3-dehydroshikimic acid, Compound Q is protocatechuic acid, and Metabolite M is shikimic acid;

(k) Compound P is chorismic acid, Compound Q is anthranilic acid, and Metabolite M is prephenic acid;

(l) Compound P is prephenic acid, Compound Q is 4-hydroxyphenylpyruvic acid, and Metabolite M is phenylpyruvic acid;

(m) Compound P is prephenic acid, Compound Q is arogenic acid, and Metabolite M is phenylpyruvic acid;

(n) Compound P is prephenic acid, Compound Q is phenylpyruvic acid, and Metabolite M is 4-hydroxyphenylpyruvic acid or arogenic acid;

(o) Compound P is 2-oxoisovaleric acid, Compound Q is 2-isopropylmalic acid, and Metabolite M is valine;

(p) Compound P is 2-oxoisovaleric acid, Compound Q is valine, and Metabolite M is 2-isopropylmalic acid;

(q) Compound P is glutamic acid, Compound Q is γ-glutamyl phosphate, and Metabolite M is N-acetylglutamate;

(r) Compound P is glutamic acid, Compound Q is N-acetylglutamate, and Metabolite M is γ-glutamyl phosphate;

(s) Compound P is aspartic acid, Compound Q is asparagine, and Metabolite M is β-aspartyl phosphate;

(t) Compound P is aspartate β-semialdehyde, Compound Q is 2,3-dihydrodipicolinic acid, and Metabolite M is homoserine;

(u) Compound P is homoserine, Compound Q is o-acetylhomoserine, and Metabolite M is homoserine phosphate;

(v) Compound P is homoserine, Compound Q is homoserine phosphate, and Metabolite M is o-acetylhomoserine; and (w) Compound P is serine, Compound Q is o-acetylserine, and Metabolite M is glycine.

(22) A method for producing the protocatechuic acid described in (j) of (21), wherein Enzyme X is shikimate dehydrogenase and Enzyme Y is 3-dehydroshikimate dehydratase.

(23) The method for producing the protocatechuic acid according to (22), wherein activity of metabolizing protocatechuic acid is lost or reduced through the introduction of a mutation of substitution, deletion, or insertion of one or more nucleotides into a translation region or transcription/translation regulatory region of one or more genes selected from the group consisting of a gene encoding protocatechuate 2,3-dioxygenase, a gene encoding protocatechuate 3,4-dioxygenase, a gene encoding protocatechuate 4,5-dioxygenase, and a gene encoding protocatechuate decarboxylase.

(24) The prokaryotic organism according to any one of (1) to (6) and (11) to (16), which is *Corynebacterium glutamicum* or *Escherichia coli*.

Effects of the Invention

According to the present invention, microorganisms that can efficiently produce useful organic compounds, such as DHS or protocatechuic acid, from a carbon source, such as glucose, can be obtained. With the use of the microorganisms of the present invention, also, DHS or protocatechuic acid can be efficiently produced with the use of a medium that is not supplemented with aromatic amino acids.

BRIEF DESCRIPTION OF THE DRAWINGS

FIG. 10 also demonstrates that Enzyme Y that converts Compound P into Compound Q is induced to express so as to increase the Enzyme Y expression level, and the amount of Compound Q is increased at a late culture stage.

FIG. 11 also demonstrates that Repressor R is induced to express so as to increase the amount of Compound P accumulated, Enzyme Y that converts the accumulated Compound P into Compound Q is induced to express so as to increase the Enzyme Y expression level, and the amount of Compound Q produced is thus increased at a late culture stage.

EMBODIMENTS FOR CARRYING OUT THE INVENTION

Figure 1:
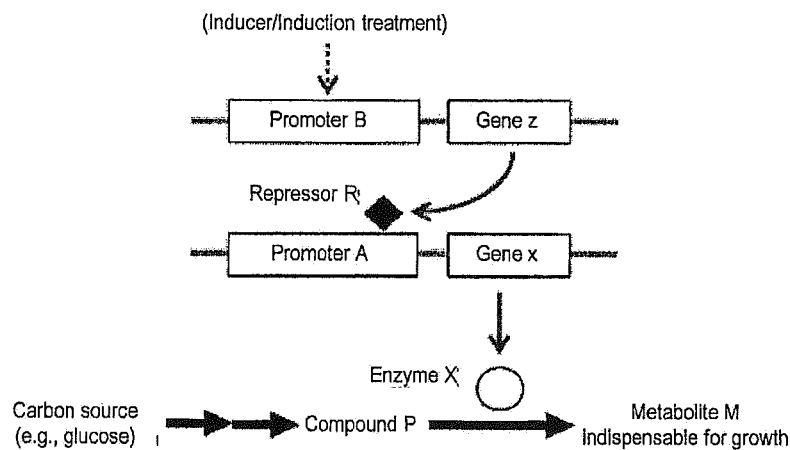
FIG. 1 shows a method for producing Compound P of interest, which is an intermediate metabolite in a biosynthetic pathway from a carbon source to Metabolite M indispensable for the growth, by allowing Repressor R, which is a product of the gene z, to regulate expression of Enzyme X (i.e., an enzyme that plays a role in conversion of Compound P into Metabolite M).
Figure 2:
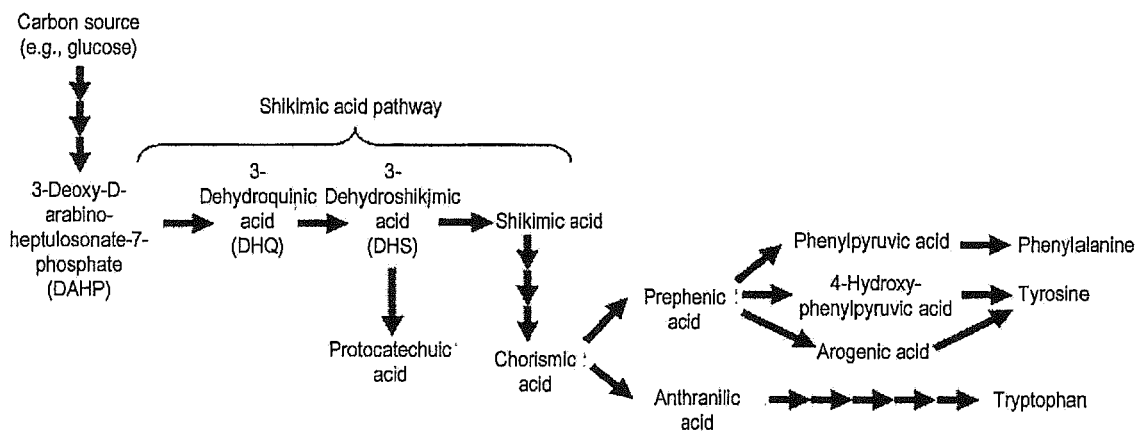
FIG. 2 shows a shikimic acid pathway associated with biosynthesis of aromatic amino acid from a carbon source.
Figure 3:
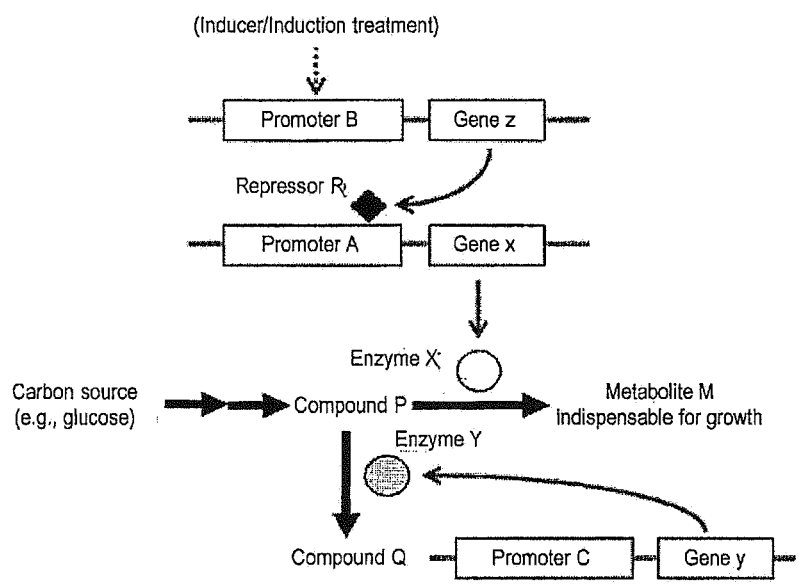
FIG. 3 shows a method of regulating the expression of an enzyme by Repressor R, which is a product of the gene z, to produce Compound P of interest in a biosynthetic pathway from a carbon source to Metabolite M indispensable for the growth and express Enzyme Y that plays a role in conversion of Compound P into Compound Q, thereby producing Compound Q of interest.

Hereafter, the present invention is described in detail with reference to FIG. 1 and FIG. 3.

The microorganisms according to the present invention are used for efficiently producing Compound P of interest, which is an intermediate metabolite in a biosynthetic pathway from a carbon source to Metabolite M indispensable for the growth and such microorganisms have the features (a) to (d) described below. Such microorganisms are preferably prokaryotic organisms in which the transcription regulatory system by Repressor R has been developed for the purpose of gene expression regulation:

(a) activity of one or more enzymes selected from among enzymes associated with biosynthesis of Compound P from a carbon source that can be used by the prokaryotic organism is enhanced compared with that of a wild-type prokaryotic organism;

(b) activity of Enzyme X is lost or reduced by a mutation of substitution, deletion, or insertion of one or more nucleotides in a translation region of a wild-type gene x encoding a protein of Enzyme X that converts Compound P into Metabolite M, a translation regulatory region of the gene, or a promoter region that accelerates the transcription of the gene x;

(c) transcription of DNA encoding active Enzyme X is regulated by Promoter A, which is different from a native promoter that accelerates the transcription of the gene x and wherein the transcription is repressed with the aid of a Repressor R protein; and (d) transcription of one or more copies of the gene z encoding a Repressor R protein is regulated by the promoter native to the gene and/or an inducible Promoter B that is different from the native promoter.

Concerning one or more enzymes selected from among enzymes associated with the biosynthetic pathway from a carbon source, such as glucose, to Compound P, enzyme activity may be enhanced and/or the amount of enzyme protein may be increased in the manner described below. Thus, the microorganisms used in the present invention can be provided with the feature (a). Specifically, enzyme activity may be enhanced and/or the amount of enzyme protein may be increased by, for example, introducing a mutation into a translation origin of the gene encoding the enzyme protein, introducing a mutation into a promoter region of the gene, substituting the promoter with another strong promoter, amplifying the gene via cloning into a multicopy plasmid, increasing the expression of a protein that positively regulates the transcription of the gene, and/or decreasing or deleting the expression of a protein that negatively regulates the transcription of the gene. Thus, the amount of Compound P produced can be increased. In the case of an enzyme that experiences the feedback inhibition by a metabolite located downstream, alternatively, an amino acid mutation that relieves such feedback inhibition may be introduced into the enzyme protein, so as to increase the amount of Compound P produced. Introduction of a mutation into such DNA or a protein can be carried out by mutagenesis, recombinant DNA technology, homologous recombination, or other techniques.

The feature (b) can be provided by deleting activity of Enzyme X via mutagenesis, recombinant DNA technology, or other techniques. Preferably, a deletion mutation is introduced into a translation region of a wild-type gene x via homologous recombination. If the entire translation region is deleted, the expression of the downstream gene may occasionally be inhibited because of the polar effects. Thus, it is preferable that an in-frame deletion mutation be introduced into a translation region at a site other than the 5' end and the 3' end of the translation region. Alternatively, activity of Enzyme X can be deleted by introducing a mutation of substitution, deletion, or insertion of one or more nucleotides into a site in the vicinity of the translation origin of the gene x or a promoter region that accelerates the transcription of the gene x. Also, the native promoter region that accelerates the transcription of the gene x may be substituted with DNA of Promoter A as defined in the feature (c), so as to provide the feature (b) and the feature (c) simultaneously.

The feature (c) can be imparted by introducing DNA encoding a protein of active Enzyme X into a site downstream of Promoter A, the transcription therefrom is repressed by Repressor R. Promoter A is different from the native promoter that accelerates the transcription of the gene x, and any promoter may be used, provided that the transcription therefrom is repressed by Repressor R. Preferable examples of Promoter A to be repressed by Repressor R in the *Escherichia coli* K-12 strain include pL promoter or pR promoter, the transcription therefrom is repressed by the λ phage cI857 gene product, lac promoter, the transcription therefrom is repressed by the lacI gene product, and the gal operon promoter, the transcription therefrom is repressed by the galR gene product. Examples of Promoter A, the transcription therefrom is repressed by Repressor R in the ATCC13032 strain include: a vanA promoter, the transcription therefrom is repressed by the vanR (cg2615) gene (hereafter referred to as "the vanR gene") product (hereafter abbreviated to as "VanR repressor"); a promoter of the rhcH (cg1309) gene (hereafter referred to as "the rhcH gene"), the transcription therefrom is repressed by the rhcR (cg1308) gene (hereafter referred to as "the rhcR gene") product (hereafter abbreviated to as "RhcR repressor") (hereafter abbreviated to as "the rhcH promoter"); and a promoter of the pcaI (cg2623) gene (hereafter referred to as "the pcaI gene"), the transcription therefrom is repressed by the pcaR (cg2624) gene (hereafter referred to as "the pcaR gene") product (hereafter abbreviated to as "PcaR repressor"). As the gene x, a gene originating from the microorganism of the present invention may be used, or a gene derived from a prokaryotic or eukaryotic organism, which is different from the microorganism of the present invention, may be used.

Under usual conditions, the Enzyme X expression level is low as a result of provision of the feature (b) and the feature (c) in the microorganisms of the present invention. However, such microorganisms have a mutation for increasing the amount of Compound P as a result of the provision of the feature (a). Thus, such microorganisms can produce the amount of Metabolite M that is necessary for the growth. When the amount of Compound P produced is very small and the growth conditions are poor, the repressed transcription caused by Repressor R may be relieved, and the Enzyme X expression level may be increased. Thus, the growth conditions of the microorganisms can be improved.

The feature (d) can be provided by constructing a gene z expression unit in which the gene z is located downstream of an inducible Promoter B that is different from the gene z promoter, in addition to a wild-type expression unit of the gene z encoding Repressor R. In addition to a wild-type gene z expression unit, a gene z expression unit located downstream of the inducible Promoter B may be incorporated into the microorganisms of the present invention. Any repressor derived from a prokaryotic organism can be used as Repressor R. It is preferable to use a repressor, the repression of which can be relieved upon, for example, the addition of an inducer or changes in temperatures. When the *Escherichia coli* K-12 strain is used as the microorganism of the present invention, specific examples of repressors that can be used include repressors encoded by the λ phage cI857 gene induced via culture at 38° C. or higher temperature, those encoded by the lacI gene induced with the addition of lactose, those encoded by the galR gene induced with the addition of galactose, and those encoded by the tetR gene induced with the addition of tetracycline. When the ATCC13032 strain is used as the microorganism of the present invention, for example, the VanR repressor, the repression of which can be relieved with the addition of ferulic acid, vanillic acid, or vanillin, the RhcR repressor, the repression of which can be relieved with the addition of resorcinol or 2,4-dihydroxybenzoic acid, or the PcaR repressor, the repression of which can be relieved with the addition of 4-hydroxybenzoic acid may be used.

Any promoter can be used as Promoter B, provided that it is an inducible promoter derived from a prokaryotic organism. When the gene z is to be expressed in the *Escherichia coli* K-12 strain, specifically, λ phage pL promoter or pR promoter, lac promoter, gal operon promoter, trp operon promoter, araBAD promoter, or the like can be used. When the gene z is to be expressed in the ATCC13032 strain, for example, vanA promoter induced with the addition of ferulic acid, vanillic acid, or vanillin, rhcH promoter induced with the addition of resorcinol or 2,4-dihydroxybenzoic acid, pcaI promoter induced with the addition of 4-hydroxybenzoic acid, nagI (cg3351) gene (hereafter referred to as "the nagI gene") promoter induced with the addition of 3-hydroxybenzoic acid (hereafter abbreviated to as "the nagI promoter"), benA (cg2637) gene (hereafter referred to as the benA gene) promoter induced with the addition of benzoic acid (hereafter abbreviated to as "the benA promoter"), or cg2118 gene promoter or ptsS (cg2925) gene (hereafter referred to as "the ptsS gene") promoter induced with the addition of fructose or sucrose can be used.

When the microorganism of the present invention has enzymatic activity for metabolizing Compound P other than Enzyme X activity and the amount of the compound accumulated may be decreased when producing Compound P, activity of one, or more metabolic enzymes for metabolizing Compound P of the microorganism may be preferably lost or reduced via mutagenesis or recombinant DNA technology.

It is preferable that the microorganisms of the present invention be prokaryotic organisms of *Corynebacterium, Brevibacterium, Arthrobacter, Nocardioidaceae, Microbacterium, Streptomyces, Amycolatopsis, Rhodococcus, Kineococcus, Acinetobacter, Pseudomonas, Pantoea, Klebsiella,* or *Escherichia*. It is more preferable that the microorganisms of the present invention be *Corynebacterium glutamicum* that is often used for amino acid production by fermentation or *Escherichia coli*, the properties of which have already been precisely analyzed.

Figure 4:
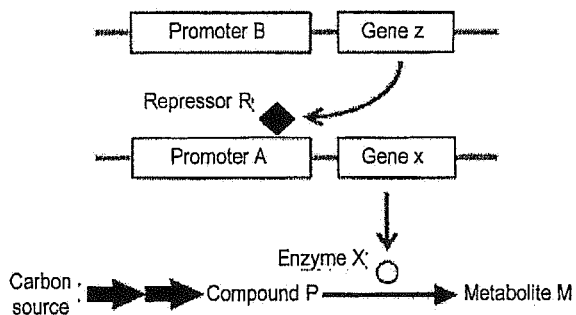
FIG. 4 demonstrates that Compound P can be efficiently produced because of the low Enzyme X expression level and the regulated amount of Metabolite M produced as a result of repression of the Promoter A transcription by Repressor R.

An example of a method for producing Compound P using the microorganism of the present invention is a method in which Compound P of interest is produced by conducting culture in a medium containing a carbon source while repressing Promoter A transcription. Since the transcription level of Promoter A that regulates Enzyme X expression is maintained at a low level by Repressor R in the microorganism of the present invention, the amount of Metabolite M produced is regulated, and Compound P can be efficiently produced (FIG. 4).

Figure 5:
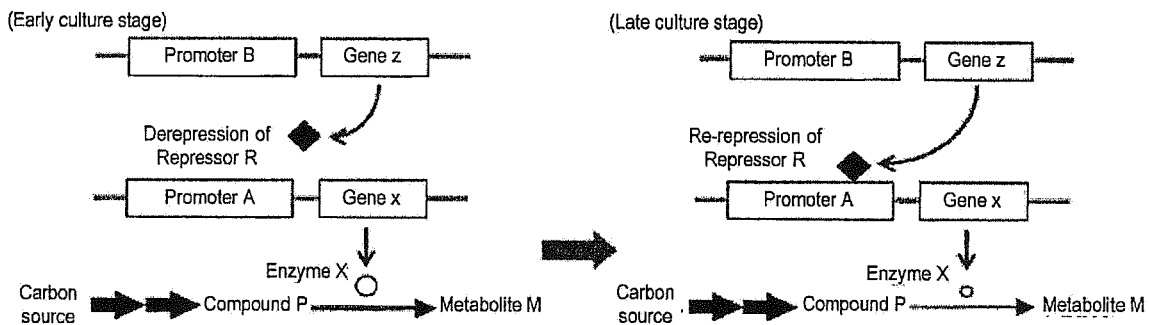
FIG. 5 demonstrates that repression of Promoter A transcription by Repressor R is relieved and Enzyme X is thus produced normally at an early culture stage, Promoter A transcription is re-repressed by Repressor R, the Enzyme X expression level is significantly lowered, and Compound P is thus accumulated at a late culture stage.

In the method of production according to the present invention, when the growth of the microorganism is slow due to a low transcription level of Promoter A that regulates Enzyme X expression, a process for producing Compound P may be divided into two processes; i.e., an early culture stage and a late culture stage. Thus, Compound P of interest can be produced. Specifically, a medium supplemented with a carbon source may be inoculated with the microorganisms, transcription is derepressed by adding an inducer or increasing/decreasing a culture temperature in accordance with the properties of Repressor R, the Enzyme X expression level is increased, and culture is then continued. Thereafter, transcription is re-repressed by Repressor R at an adequate timing, so as to inhibit Enzyme X expression. Thus, the amount of Compound P produced can be increased (FIG. 5). When Promoter A that is induced with the addition of an inducer is used, the amount of the inducer to be added is adjusted so as to deplete the inducer at the late culture stage. Thus, transcription can be re-repressed by Repressor R. When Promoter A that is induced by increasing/decreasing a culture temperature is used, a culture temperature may be returned to the level at which transcription is repressed by Repressor R. Thus, transcription can be re-repressed by Repressor R.

Figure 6:
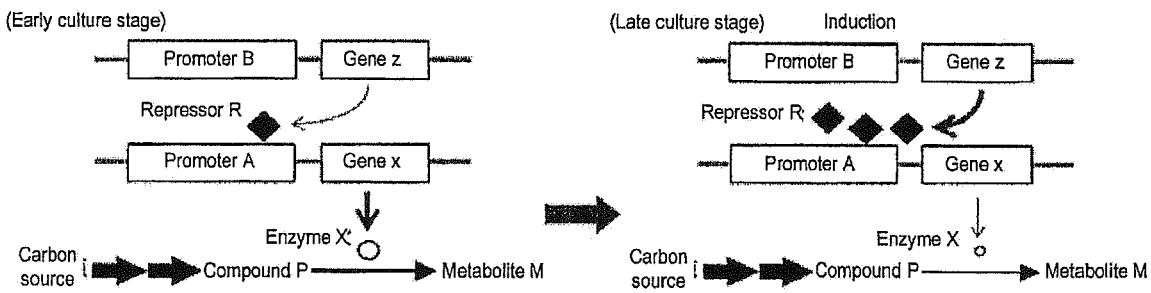
FIG. 6 demonstrates that Promoter A transcription occurs and Enzyme X is produced normally because of a small amount of Repressor R at an early culture stage, the Enzyme X expression level is significantly lowered because of the increased amount of Repressor R, and Compound P is thus accumulated at a late culture stage.

With the use of the microorganism of the present invention in which Repressor R expression is directed by the inducible Promoter B, preferably, the process for producing Compound P is divided into two stages: i.e., the early culture stage and the late culture stage. Thus, Compound P of interest is produced. Specifically, a medium containing a carbon source is inoculated with the microorganisms, the microorganisms are allowed to grow, and an inducer is added or a culture temperature is increased or decreased in accordance with the properties of the inducible Promoter B so as to activate the inducible Promoter B and increase the amount of Repressor R produced. Thus, production of Metabolite M is suppressed, and the amount of Compound P produced is increased (FIG. 6).

According to the method of production with the use of the microorganism of the present invention, as described above, the amount of Compound P produced can be easily maximized via a different culture method with the use of the same microorganisms, in accordance with the growth condition of the microorganisms or the influence of Compound P imposed on the microorganisms.

Any carbon sources can be used, provided that the microorganism of the present invention can use such carbon sources. Examples of carbon sources that can be used include: saccharides, such as glucose, sucrose, and fructose; alcohols, such as ethanol and methanol; organic acids, such as citric acid, malic acid, and succinic acid; glycerol; and blackstrap molasses.

Compound P can be any organic compound, provided that it is a metabolite in a biosynthetic pathway in which a metabolite indispensable for the growth is produced from a carbon source. Examples thereof include DHS, glutamic acid, aspartic acid, and serine.

DHS can be produced by regulating expression of shikimate dehydrogenase (Enzyme X) that produces shikimic acid (Metabolite M). While DHS is useful as an antioxidant (U.S. Pat. No. 5,821,266), it can also be used as a starting material for producing protocatechuic acid, shikimic acid, or the like with the use of microorganisms.

A useful amino acid; i.e., glutamic acid, can be produced by regulating expression of amino acid-N-acetyltransferase (Enzyme X) that produces N-acetylglutamate (Metabolite M) or γ-glutamylkinase (Enzyme X) that produces γ-glutamyl phosphate (Metabolite M).

A useful amino acid; i.e., aspartic acid, can be produced by regulating expression of aspartokinase (Enzyme X) that produces β-aspartyl phosphate (Metabolite M) or asparagine synthetase (Enzyme X) that produces asparagine (Metabolite M).

A useful amino acid; i.e., serine, can be produced by regulating expression of serine hydroxymethyltransferase (Enzyme X) that produces glycine (Metabolite M) or serine transferase (Enzyme X) that produces o-acetylserine (Metabolite M).

As a specific example, a strain derived from the ATCC13032 strain that efficiently produces DHS is described in detail. The genome sequence of the ATCC13032 strain can be obtained from the database of the GenBank (hereafter abbreviated to as "GB") of the National Center for Biotechnology Information (hereafter abbreviated to as "NCBI") under GB Accession Number BX927147. While the genome sequence that is substantially the same as the aforementioned sequence can be obtained under GB Accession Number NC_003450, in the present description, the nucleotide positions and the genetic name are described with reference to the nucleotide numbers and the genetic name of GB Accession Number BX927147.

Strains derived from the ATCC13032 strain that produces DHS are microorganisms having the features (aa) to (dd) described below.

(aa) Among enzymes associated with the biosynthesis of DHS (Compound P) from a carbon source that can be used by the strain identified above, activity of one or more enzymes selected therefrom is enhanced compared with that of a wild-type strain.

(bb) The capacity for conversion of DHS into shikimic acid is lost or reduced because of the presence of a mutation of substitution, deletion, or insertion of one or more nucleotides in a translation region or a translation regulatory region of a wild-type gene (gene X) encoding a protein of shikimate dehydrogenase (Enzyme X) that converts DHS into shikimic acid (Metabolite M) or a promoter region that accelerates the transcription of the gene. The ATCC13032 strain comprises, as the genes encoding active shikimate dehydrogenase, the aroE3 (cg1835) gene (a DNA region comprising nucleotides 1,726,078 to 1,726,908 of a complementary strand), the aroE1 (cg1283) gene (a DNA region comprising nucleotides 1,182,337 to 1,183,143 of a complementary strand), and the qsuD (cg0504) gene (a DNA region comprising nucleotides 446,537 to 447,388). A mutation is introduced into the aroE3 gene that plays a key role in conversion of DHS into shikimic acid, active shikimate dehydrogenase expression of the gene is lost or lowered, and the feature (bb) can be imparted as a consequence. In addition to a mutation of the aroE3 gene, a mutation that results in the lost or lowered active shikimate dehydrogenase expression may be introduced into the qsuD gene and/or aroE1 gene. Thus, the feature (bb) can be imparted.

(cc) Transcription of DNA encoding active Enzyme X is regulated by Promoter A that is different from the native promoter that accelerates the transcription of the gene x and wherein the transcription is repressed with the aid of a Repressor R protein.

(dd) One or more copies of the gene z encoding a Repressor R protein are present, and transcription of such gene is regulated by the promoter native to the gene and/or an inducible Promoter B that is different from the native promoter.

As described above, the VanR repressor, the repression of which can be relieved with the addition of ferulic acid, vanillic acid, or vanillin, the RhcR repressor, the repression of which can be relieved with the addition of resorcinol or 2,4-dihydroxybenzoic acid, or the PcaR repressor, the repression of which can be relieved with the addition of 4-dihydroxybenzoic acid may be used as Repressor R.

Examples of Promoter A that is repressed by Repressor R in the ATCC13032 strain include the vanA promoter, the transcription therefrom is repressed by the VanR repressor, the rhcH promoter, the transcription therefrom is repressed by the RhcR repressor, and the a promoter of the pcaI gene, the transcription therefrom is repressed by the PcaR repressor.

Examples of Promoter B that can be used include the vanA promoter induced with the addition of ferulic acid, vanillic acid, or vanillin, the rhcH promoter induced with the addition of Resorcinol or 2,4-dihydroxybenzoic acid, the pcaI promoter induced with the addition of 4-hydroxybenzoic acid, the nagI promoter induced with the addition of 3-hydroxybenzoic acid, the benA promoter induced with the addition of benzoic acid, and the cg2118 gene promoter or the ptsS promoter induced with the addition of fructose or sucrose.

The native promoter region that accelerates the transcription of the aroE3 gene (gene x) encoding a protein of shikimate dehydrogenase (Enzyme X) may be substituted with DNA of Promoter A as described with regard to the feature (cc), so as to impart the feature (bb) and the feature (cc) simultaneously.

In order to impart the feature (aa), a mutation that potentiates a pathway for generating DHS from DAHP or a mutation that increases the amount of DAHP produced may be introduced in accordance with a conventional technique.

DAHP is converted into 3-dehydroquinic acid (hereafter abbreviated to as "DHQ") by 3-dehydroquinate synthase, and DHQ is further converted into DHS by DHQ dehydratase. Thus, a mutation may be introduced into a transcription/translation regulatory region of the aroB (cg1827) gene encoding DHQ synthetase (hereafter referred to as "the aroB gene") and/or the aroD (cg0503) gene encoding DHQ dehydratase (hereafter referred to as "the aroD gene"), so as to enhance the expression level of DHQ synthetase and/or DHQ dehydratase and increase the amount of DHS. For example, the native promoter that accelerates the transcription of the aroB gene and/or aroD gene may be substituted with the Tu promoter with higher promoter activity, so as to increase the amount of DHS.

Alternatively, the amount of DAHP may be increased, so as to increase the amount of DHS. The amount of DAHP may be increased by relieving feedback inhibition of DAHP synthase by aromatic amino acids, enhancing the DAHP synthase expression level, or increasing the amount of erythrose 4-phosphate (hereafter abbreviated to as "E4P") or phosphoenolpyruvic acid (hereafter abbreviated to as "PEP"), which is a DAHP synthase substrate.

Tryptophan, tyrosine, or phenylalanine often causes the feedback inhibition to DAHP synthase. Since it is known that the feedback inhibition can be relieved by the introduction of a mutation, such as an amino acid substitution, into DAHP synthase, a mutation may be introduced into a DAHP synthase gene, such as the aroF (cg1129) gene (hereafter referred to as "the aroF gene") or the aroG (cg2391) gene (hereafter referred to as "the aroG gene"), so as to increase the amount of DAHP.

DAHP synthase expression can be enhanced by introducing a mutation into a transcription/translation regulatory region of the gene encoding DAHP synthase. For example, the native promoter that accelerates the transcription of the gene encoding DAHP synthase may be substituted with the Tu promoter, so as to increase the amount of DAHP.

For example, the amount of E4P, which is a DAHP synthase substrate, can be increased by introducing a mutation into a transcription/translation regulatory region of an enzyme gene associated with the pentose phosphate pathway, such as the tkt (cg1774) gene encoding transketolase (hereafter referred to as "the tkt gene"), the tal (cg1776) gene encoding transaldolase (hereafter referred to as "the cg1776 gene"), or the zwf (cg1778) gene encoding glucose-6-phosphate-1-dehydrogenase, so as to enhance the expression of such gene.

The amount of PEP, which is a DAHP synthase substrate, can be increased by introducing a mutation into a transcription/translation regulatory region of the pps (cg0644) gene encoding PEP synthetase or the pck (cg3169) gene encoding PEP carboxykinase, so as to enhance the expression of such gene.

Further, a mutation can be introduced into a translation region or the transcription/translation regulatory gene of, for example, the pyk (cg2291) gene encoding pyruvate kinase, the ppc (cg1787) gene encoding PEP carboxylase, or the gene encoding phosphotransferase associated with the uptake of a sugar, such as glucose, (e.g., cg2117 genes). Thus, PEP conversion can be inhibited, and the amount of PEP can then be increased.

A mutation may be introduced into a single gene so as to impart the feature (aa). In order to further increase the amount of DHS produced, it is preferable that mutations be introduced into a plurality of the genes described above.

The strain derived from the ATCC13032 strain having the features (aa) to (dd) described above is capable of producing DHS from a carbon source, such as glucose. The aroD gene encoding DHQ dehydratase constitutes an operon with the qsuB (cg0502) gene encoding DHS dehydratase that converts DHS into protocatechuic acid (hereafter referred to as "the qsuB gene"). If aroD gene expression is enhanced via promoter substitution so as to impart the feature (aa), accordingly, qsuB gene expression is also enhanced, and a part of the accumulated DHS is disadvantageously converted into protocatechuic acid. In order to inhibit the conversion of DHS into protocatechuic acid, it is preferable that a mutation be introduced into a translation region or a transcription/translation regulatory region of the qsuB gene.

When the microorganisms of the present invention have the feature (e) described below in addition to the features (a) to (d) described above, Compound P in a biosynthetic pathway from a carbon source to Metabolite M indispensable for the growth can be converted into Compound Q with the use of such microorganism. Thus, Compound Q of interest can be efficiently produced.

(e) The capacity for converting Compound P into Compound Q is enhanced or gene y expression is regulated differently from a wild-type gene because of a mutation of substitution, deletion, or insertion of one or more nucleotides in a translation region of the gene y encoding a protein of Enzyme Y, a translation regulatory region of the gene, or a promoter region that accelerates the transcription of the gene y.

As to the feature (e), The Enzyme Y expression level is often insufficient in the form of a wild-type strain. Thus, a mutation of substitution, deletion, or insertion of one or more nucleotides is introduced into the translation regulatory region of the gene y or the promoter region that accelerates the transcription of the gene y, so as to enhance the Enzyme Y expression level or regulate gene y transcription in a manner different from that for a wild-type promoter. Thus, the feature (e) can be imparted. The first enzyme in the branched pathway often experiences the feedback inhibition by a final product. Accordingly, a mutation is introduced into the translation region of the gene y, so as to relieve the feedback inhibition and enhance the activity of Enzyme Y. Thus, the feature (e) can be imparted.

Preferably, a part of or the entire promoter region that accelerates the gene y transcription is substituted with DNA of Promoter C, which is different from the native promoter and Promoter A that accelerate gene y transcription. Thus, the feature (e) can be imparted.

A promoter that is different from the promoter native to the gene y or Promoter A can be used as Promoter C. While a constitutive expression promoter can also be used as Promoter C, the use of an inducible promoter is preferable.

Any of the promoters exemplified as Promoter B used to impart the feature (d) above can be used as an inducible promoter.

Examples of Promoter C that can be used include λ phage pL promoter or pR promoter, lac promoter, gal operon promoter, trp operon promoter, araBAD promoter, vanA promoter induced with the addition of ferulic acid, vanillic acid, or vanillin, rhcH promoter induced with the addition of resorcinol or 2,4-dihydroxybenzoic acid, pcaI promoter induced with the addition of 4-hydroxybenzoic acid, nagI promoter induced with the addition of 3-hydroxybenzoic acid, benA promoter induced with the addition of benzoic acid, and cg2118 gene promoter or ptsS promoter induced with the addition of fructose or sucrose.

Promoter C used to impart the feature (e) may be the same as Promoter B used to impart the feature (d). Transcription of Promoter C may be regulated by a protein that regulates the Promoter B transcription.

When the amount of Compound P accumulated may be decreased in the process of production thereof because of enzymatic activity of the microorganism of the present invention for metabolizing Compound Q, activity of one or more enzymes metabolizing Compound P of the microorganism is preferably lost or reduced via mutagenesis or recombinant DNA technology.

Figure 7:
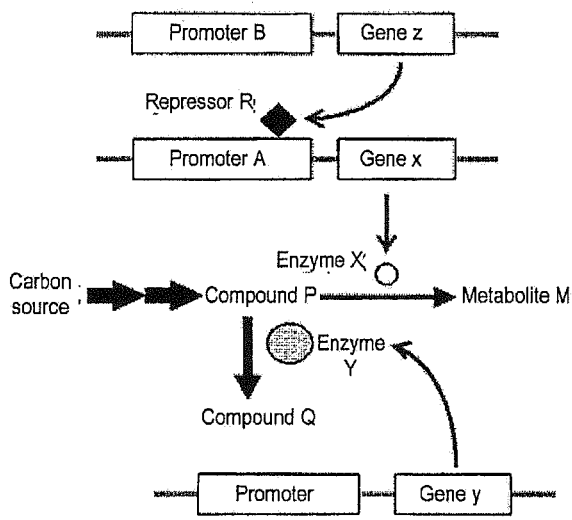
FIG. 7 demonstrates that promoter transcription is repressed by Repressor R encoded by the gene z located downstream of Promoter B, the Enzyme X expression level is significantly lowered, Compound P is accumulated, and Compound P is then converted into Compound Q with the aid of Enzyme Y, which is a product of the gene z.

According to the method for producing Compound Q using the microorganism of the present invention, for example, culture is conducted in a medium containing a carbon source while repressing the Promoter A transcription. Thus, Compound Q is produced. In the microorganism of the present invention, the transcription level of Promoter A that regulates Enzyme X expression is maintained to a low level by Repressor R. Thus, the amount of Metabolite M produced is regulated, and Compound Q can be efficiently produced from Compound P (FIG. 7).

Figure 8:
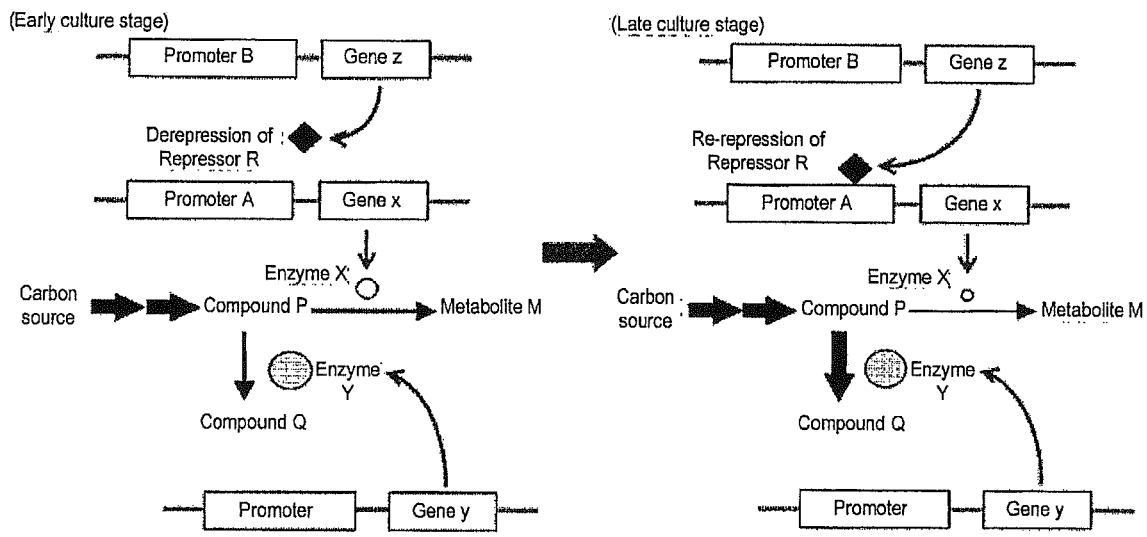
FIG. 8 demonstrates that repression of Promoter A transcription by Repressor R is relieved and Enzyme X is thus produced normally at an early culture stage, Promoter A transcription is re-repressed by Repressor R, the Enzyme X expression level is significantly lowered, and the accumulated Compound P is converted into Compound Q with the aid of Enzyme Y at a late culture stage.

When the microorganism grows slowly because of a low transcription level of Promoter A that regulates Enzyme X expression in the method of production according to the present invention, a process for producing Compound Q is preferably divided into two processes; i.e., an early culture stage and a late culture stage. Specifically, a medium containing a carbon source may be inoculated with the microorganisms, transcription is derepressed by adding an inducer or increasing/decreasing a culture temperature in accordance with the properties of Repressor R, the Enzyme X expression level is increased, and culture is continued. Thereafter, transcription is re-repressed by Repressor R at an adequate timing so as to repress Enzyme X expression. Thus, the amount of Compound Q produced from Compound P can be increased (FIG. 8). When Promoter A that is induced with the addition of an inducer is used, the amount of the inducer to be added is adjusted so as to deplete the inducer at the late culture stage. Thus, transcription can be re-repressed by Repressor R. When Promoter A that is induced by increasing/decreasing a culture temperature is used, a culture temperature may be returned to the level at which transcription is repressed by Repressor R. Thus, transcription can be re-repressed by Repressor R.

Figure 9:
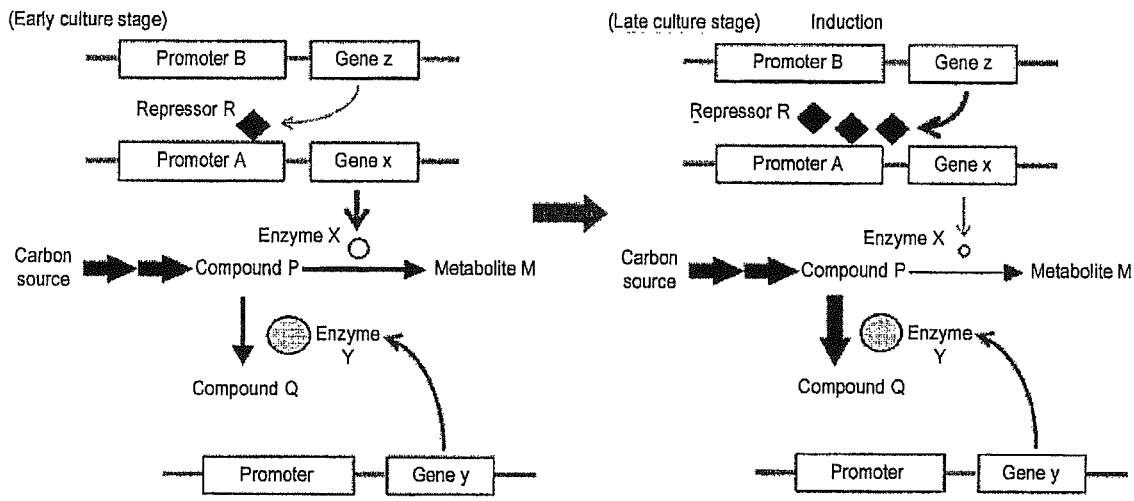
FIG. 9 demonstrates that Promoter A transcription occurs and Enzyme X is produced normally because of a small amount of Repressor R at an early culture stage, the Enzyme X expression level is significantly lowered because of the increased amount of Repressor R, and the accumulated Compound P is converted into Compound Q with the aid of Enzyme Y at a late culture stage.

With the use of the microorganism of the present invention in which Repressor R expression is directed by the inducible Promoter B, preferably, the process for producing Compound Q is divided into two stages: i.e., the early culture stage and the late culture stage, so as to produce Compound Q. Specifically, a medium containing a carbon source is inoculated with the microorganisms, the microorganisms are allowed to grow, and an inducer is added or a culture temperature is increased or decreased in accordance with the properties of the inducible Promoter B so as to activate the inducible Promoter B. Thus, the amount of Repressor R produced is increased, thereby suppressing the production of Metabolite M and increasing the amount of Compound Q produced from Compound P (FIG. 9).

Figure 10:
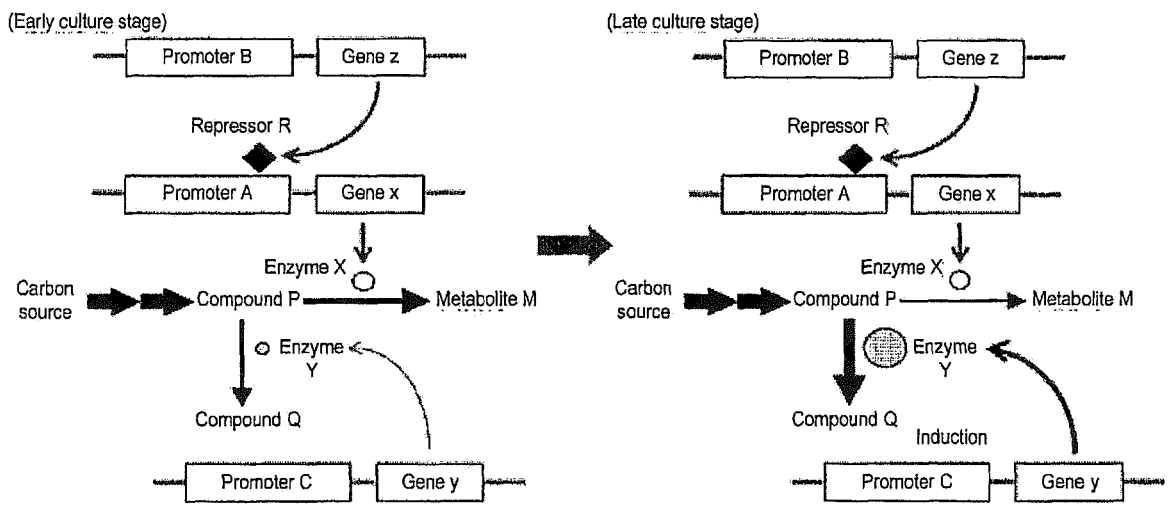
FIG. 10 demonstrates that Promoter A transcription is repressed by Repressor R, the Enzyme X expression level is maintained low so as to regulate the amount of Metabolite M produced, and a small amount of Compound P is thus produced while allowing microorganisms to grow at an early culture stage.
Figure 11:
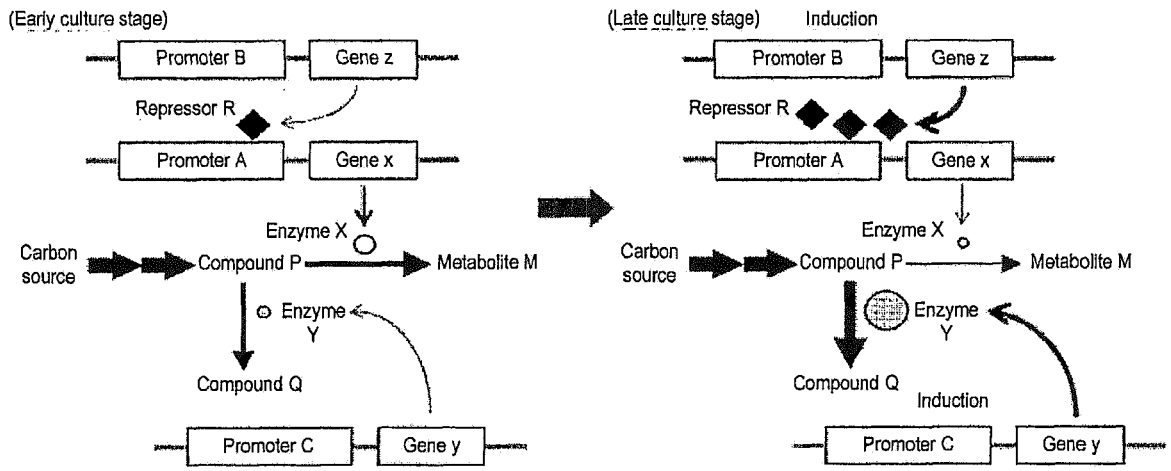
FIG. 11 demonstrates that Promoter A transcription is repressed by Repressor R, the Enzyme X expression level is maintained low so as to regulate the amount of Metabolite M produced, and a small amount of Compound P is thus produced while allowing microorganisms to grow at an early culture stage.

When Compound Q influences the growth of the microorganism of the present invention in the production method according to the present invention, it is preferable that Compound Q be produced with the use of the microorganism of the present invention in which Enzyme Y expression is located downstream of the inducible Promoter C by dividing the process for producing Compound Q into two stages: i.e., the early culture stage and the late culture stage. Specifically, a medium containing a carbon source is inoculated with the microorganisms, the microorganisms are allowed to grow, and an inducer is added or a culture temperature is increased or decreased in accordance with the properties of the inducible Promoter C so as to activate the inducible Promoter C and increase the amount of Enzyme Y produced. Thus, the amount of Compound Q produced from Compound P can be increased (FIG. 10). Further, transcription of the inducible Promoter C is activated at the late culture stage so as to increase the amount of Enzyme Y produced, and the inducible Promoter B is also activated so as to increase the amount of Repressor R produced. Thus, the production of Metabolite M may be suppressed, and the amount of Compound Q produced from Compound P may be increased (FIG. 11).

In such a case, the same promoters are used as Promoter C and as Promoter B, so that Promoter C and Promoter B can be induced at the same time. If Promoter C and Promoter B are selected from among promoters, the transcription of which is regulated by the same regulatory protein, Promoter C and Promoter B can be induced at the same time even if they are different from each other.

According to the method of production with the use of the microorganism of the present invention, as described above, the amount of Compound Q produced can be easily maximized via a different culture method with the use of the same microorganisms, in accordance with the growth condition of the microorganisms or the influence of Compound Q imposed on the microorganisms.

Any compound can be produced as Compound Q that can be produced with the use of the microorganism of the present invention, provided that Compound Q can be produced through a pathway branched from Compound P in a biosynthetic pathway or metabolic pathway in which Metabolite M indispensable for the growth is generated from a carbon source through Compound P.

Compound P can be any organic compound, provided that it is a metabolite in a biosynthetic pathway in which a metabolite indispensable for the growth is produced from a carbon source. Examples thereof include DHS, chorismic acid, prephenic acid, 2-oxoisovaleric acid, glutamic acid, aspartic acid, aspartate β-semialdehyde, homoserine, and serine. Compound Q can be any organic compound, provided that it can be converted from Compound P with the aid of Enzyme Y. Examples thereof include protocatechuic acid, anthranilic acid, 4-hydroxyphenylpyruvic acid, arogenic acid, phenylpyruvic acid, 2-isopropylmalic acid, valine, γ-glutamyl phosphate, N-acetylglutamate, asparagine, 2,3-dihydrodipicolinic acid, and o-acetylhomoserine.

When Compound P is DHS, shikimic acid (Metabolite M) is produced with the aid of shikimate dehydrogenase (Enzyme X), and protocatechuic acid (Compound P) can be produced with the aid of DHS dehydratase (Enzyme Y). While protocatechuic acid serves as a starting material for a pharmaceutical, agricultural, or aromatic product, it can also be used as a starting material for producing 2-pyrone-4,6-dicarboxylic acid, which is expected as a novel plastic raw material, with the use of the microorganism.

When Compound P is chorismic acid, prephenic acid (Metabolite M) is produced with the aid of chorismic acid mutase (Enzyme X), and anthranilic acid (Compound P) can be produced with the aid of anthranilic acid synthetase (Enzyme Y). Anthranilic acid serves as a raw material for synthesizing tryptophan, which is an aromatic amino acid. If such microorganism has a tryptophan biosynthetic pathway, tryptophan can be directly produced.

When Compound P is prephenic acid, phenylpyruvic acid (Metabolite M) is produced with the aid of prephenic acid dehydratase (Enzyme X). When the microorganism of the present invention is the *Escherichia coli* K-12 strain, for example, 4-hydroxyphenylpyruvic acid (Compound Q) can be produced with the aid of prephenic acid dehydrogenase (Enzyme Y). 4-Hydroxyphenylpyruvic acid serves as a raw material for synthesizing tyrosine, which is an aromatic amino acid. If the microorganism has the tyrosine biosynthetic pathway from 4-hydroxyphenylpyruvic acid, accordingly, tyrosine can be directly produced.

When Compound P is prephenic acid, phenylpyruvic acid (Metabolite M) is produced with the aid of prephenic acid dehydratase (Enzyme X). When the microorganism of the present invention is the *Corynebacterium glutamicum*, for example, arogenic acid (Compound Q) can be produced with the aid of prephenic acid aminotransferase (Enzyme Y). Arogenic acid serves as a raw material for synthesizing tyrosine, which is an aromatic amino acid. If the microorganism has the tyrosine biosynthetic pathway from arogenic acid, accordingly, tyrosine can be directly produced.

When Compound P is prephenic acid and the microorganism of the present invention is the *Escherichia coli* K-12 strain, for example, 4-hydroxyphenylpyruvic acid (Metabolite M) is produced with the aid of prephenic acid dehydrogenase (Enzyme X). When the microorganism of the present invention is *Corynebacterium glutamicum*, for example, arogenic acid (Metabolite M) is produced with the aid of prephenic acid dehydrogenase (Enzyme X), and phenylpyruvic acid (Compound Q) can also be produced with the aid of prephenic acid dehydratase (Enzyme Y). Phenylpyruvic acid serves as a raw material for synthesizing phenylalanine, which is an aromatic amino acid. If the microorganism has the phenylalanine biosynthetic pathway, accordingly, phenylalanine can be directly produced.

When Compound P is 2-oxoisovaleric acid, valine (Metabolite M) is produced with the aid of branched-chain-amino-acid aminotransferase (Enzyme X), and 2-isopropylmalic acid (Compound Q) can be produced with the aid of 2-isopropylmalic acid synthetase (Enzyme Y). 2-Isopropylmalic acid serves as a raw material for synthesizing leucine. If the microorganism has the leucine biosynthetic pathway, accordingly, leucine can be directly produced.

When Compound P is 2-oxoisovaleric acid, 2-isopropylmalic acid (Metabolite M) is produced with the aid of 2-isopropylmalic acid synthetase (Enzyme X), and valine (Compound Q) can be produced with the aid of branched-chain-amino-acid aminotransferase (Enzyme Y).

When Compound P is glutamic acid, N-acetylglutamate (Metabolite M) is produced with the aid of amino acid-N-acetyltransferase (Enzyme X), and γ-glutamyl phosphate (Compound Q) can be produced with the aid of γ-glutamylkinase (Enzyme Y). γ-Glutamyl phosphate serves as a raw material for synthesizing proline. If the microorganism has the proline biosynthetic pathway, accordingly, proline can be directly produced.

When Compound P is glutamic acid, γ-glutamyl phosphate (Metabolite M) is produced with the aid of γ-glutamylkinase (Enzyme X), and N-acetylglutamate (Compound Q) can be produced with the aid of amino acid-N-acetyltransferase (Enzyme Y). N-acetylglutamate serves as a raw material for synthesizing arginine. If the microorganism has the arginine biosynthetic pathway, accordingly, arginine can be directly produced.

When Compound P is aspartic acid, β-aspartyl phosphate (Metabolite M) is produced with the aid of aspartokinase (Enzyme X), and asparagine (Compound Q) can be produced with the aid of asparagine synthetase (Enzyme Y).

When Compound P is aspartate β-semialdehyde, homoserine (Metabolite M) is produced with the aid of homoserine dehydrogenase (Enzyme X), and 2,3-dihydrodipicolinic acid (Compound Q) can be produced with the aid of dihydroxypyrophosphate synthetase (Enzyme Y). 2,3-Dihydrodipicolinic acid serves as a raw material for synthesizing lysine. If the microorganism has the biosynthetic pathway in which lysine is synthesized from 2,3-dihydrodipicolinic acid, accordingly, lysine can be directly produced.

When Compound P is homoserine, homoserine phosphate (Metabolite M) is produced with the aid of homoserine kinase (Enzyme X), and o-acetylhomoserine (Compound Q) can be produced with the aid of homoserine acetyltransferase (Enzyme Y). o-Acetylhomoserine serves as a raw material for synthesizing methionine. If the microorganism has the methionine biosynthetic pathway, accordingly, methionine can be directly produced.

When Compound P is homoserine, o-acetylhomoserine (Metabolite M) is produced with the aid of homoserine acetyltransferase (Enzyme X), and homoserine phosphate (Compound Q) can be produced with the aid of homoserine kinase (Enzyme X). Homoserine phosphate serves as a raw material for synthesizing threonine or isoleucine. If the microorganism has the isoleucine biosynthetic pathway, accordingly, threonine or isoleucine can be directly produced.

When Compound P is serine, glycine (Metabolite M) is produced with the aid of serine hydroxymethyltransferase (Enzyme X), and o-acetylserine (Compound Q) can be produced with the aid of serine transferase (Enzyme Y). o-Acetylserine serves as a raw material, for synthesizing cysteine. If the microorganism has the cysteine biosynthetic pathway, accordingly, cysteine can be directly produced.

The gene encoding Enzyme Y associated with the production of Compound Q may be derived from the microorganism of the present invention or it may be derived from a prokaryotic or eukaryotic organism that is different from the microorganism of the present invention. When producing protocatechuic acid with the use of the microorganism of the present invention, for example, the ATCC13032 strain comprises the DHS dehydratase gene, and, accordingly, the gene product thereof may be used for the production of protocatechuic acid. In contrast, the *Escherichia coli* K-12 strain does not comprise the DHS dehydratase gene. This requires the use of the DHS dehydratase gene derived from another microorganism.

As a more specific example, a strain capable of efficiently producing protocatechuic acid, which can be created by imparting a DHS-producing strain derived from the ATCC13032 strain with the feature (ee), is described in detail.

A strain derived from the ATCC13032 strain capable of producing protocatechuic acid has the feature (ee) described below, in addition to the features (aa) to (dd) above.

(ee) Transcription of the qsuB gene is regulated by Promoter C, which is different from the native promoter that accelerates the transcription of the qsuB gene (gene y: nucleotides 444,184 to 446,040) encoding a protein of DHS dehydratase (Enzyme Y) converting DHS into protocatechuic acid, and is different from Promoter A.

A strain derived from the ATCC13032 strain having the features (aa) to (ee) described above is capable of producing protocatechuic acid from a carbon source such as glucose; however, such strain comprises protocatechuic acid dioxygenase. Thus, protocatechuic acid that had been produced may be degraded, and the amount of protocatechuic acid may be decreased. Accordingly, it is preferable that a mutation of substitution, deletion, or insertion of one or more nucleotides be introduced into a translation region or a transcription/translation regulatory region of the pcaG (cg2630) gene encoding the protocatechuate 4,5-dioxygenase alpha subunit protein (nucleotide numbers of the complementary strand: 2,511,382 to 2,511,996) and/or the pcaH (cg2631) gene encoding protocatechuate 4,5-dioxygenase beta subunit protein (nucleotide numbers of the complementary strand: 2,512,008 to 2,512,700), so as to delete or decrease the activity of the enzyme for degradation.

Also, the strain comprises p-hydroxybenzoic acid hydroxylase that hydroxylates position 5 of protocatechuic acid and catalyzes conversion thereof into gallic acid. Thus, a part of protocatechuic acid generated may be converted into gallic acid. Accordingly, it is preferable that a mutation of substitution, deletion, or insertion of one or more nucleotides be introduced into a translation region or a transcription/translation regulatory region of the pobB (cg1226) gene (nucleotide numbers of the complementary strand: 1,126, 301 to 1,127,488) encoding p-hydroxybenzoic acid hydroxylase protein, so as to delete or decrease hydroxylation activity of the p-hydroxybenzoic acid hydroxylase.

Hereafter, methods for DNA cloning and production of mutants are described with reference to the production of the microorganism of the present invention. If the microorganism of the present invention belongs to *Corynebacterium, Brevibacterium, Arthrobacter, Nocardioidaceae, Microbacterium, Streptomyces, Amycolatopsis, Rhodococcus, Kineococcus, Acinetobactor, Pseudomonas, Pantoea, Klebsiella,* or *Escherichia*, as described above, any of such microorganisms can be used. A method of mutagenesis into the ATCC13032 strain is described in detail. The *Escherichia coli* K-12 strain is mainly subjected to DNA cloning or mutagenesis as a host strain.

The *Escherichia coli* K-12 strain and the ATCC13032 strain are cultured in accordance with conventional techniques that are usually employed for culturing bacteria of *Escherichia coli* and *Corynebacterium*, respectively. After the culture, chromosome DNAs of the microorganisms are isolated and purified in accordance with a conventional technique (e.g., the method described in Current Protocols in Molecular Biology). Through techniques, such as digestion with restriction enzymes, polymerase chain reactions (PCR), or hybridization with the use of synthetic DNA, fragments containing DNAs encoding the promoters or metabolic enzymes can be obtained from the chromosome DNAs.

As an *Escherichia coli* vector used for DNA ligation for the purpose of DNA cloning or mutagenesis, a plasmid vector, a phage vector, or other vector can be used, provided that it is capable of autonomous replication in, for example, the *Escherichia coli* K-12 strain. Specific examples of vectors that can be used include pUC19 (Gene, 33, 103, 1985), pUC18, and pBR322.

Any microorganism of *Escherichia coli* can be used as a host for the vector. Specific examples include *Escherichia coli* XL1-Blue MRF' (manufactured by Stratagene, Strategies, 5, 81, 1992), *Escherichia coli* JM109, and *Escherichia coli* BL21.

When the DNA is to be introduced into a microorganism of *Corynebacterium, Brevibacterium, Arthrobacter, Nocardioidaceae, Microbacterium, Streptomyces, Amycolatopsis, Rhodococcus, Kineococcus, Acinetobacter, Pseudomonas, Pantoea, Klebsiella*, or *Escherichia*, a vector that is capable of autonomous replication therein is used. Preferably, a shuttle vector that is capable of autonomous replication both in any of the microorganisms described above and in the *Escherichia coli* K-12 strain is used to introduce the recombinant DNA into the host microorganism.

Examples of shuttle vectors capable of autonomous replication in microorganisms of *Corynebacterium* include pAM330 (JP S58-67699 A (1983)) and pHM1519 (JP S58-77895 A (1983)). Also, a DNA fragment that enables a plasmid to autonomously replicate in *Corynebacterium* is removed from such vector and inserted into an *Escherichia coli-Corynebacterium* shuttle vector. The resulting vector can be used as a vector that is capable of autonomous replication both in *Escherichia coli* and *Corynebacterium*. For example, a replication region of the pHM1519 plasmid of the *Corynebacterium glutamicum* ATCC13058 strain is inserted into the *Escherichia coli* vector, pHSG298 (Takara Bio Inc.), as a replication region that allows a plasmid to be replicated in a *Corynebacterium* strain. Thus, such shuttle vector can be constructed and conserved. The ATCC13032 strain and the *Corynebacterium glutamicum* ATCC13058 strain can be obtained from the Biological Resource Center, the National Institute of Technology and Evaluation (hereafter abbreviated to as "NITE").

DNA can be introduced by any method for introducing DNA into the host cell. Examples of methods include a method involving the use of calcium ions (Proc. Natl. Acad. Sci. U.S.A., 69, 2110, 1972) and electroporation (Nucleic Acids Res., 16, 6127, 1988). DNA can be introduced into *Corynebacterium glutamicum* by the method of van der Rest et al. (Appl. Microbiol. Biotechnol., 52, 541, 1999).

DNA can be extracted from the thus-obtained transformant, and the nucleotide sequence of DNA of the present invention can be determined. The nucleotide sequence can be determined by a conventional method of nucleotide sequence analysis, such as the dideoxy method (Proc. Natl. Acad. Sci. U.S.A., 74, 5463, 1977), or with the use of a nucleotide sequence analyzer, such as the 3730x1 DNA analyzer (manufactured by Applied Biosystems).

On the basis of the DNA nucleotide sequence determined above, the target DNA can be chemically synthesized using the 8905 DNA synthesizer (manufactured by PerSeptive Biosystems, Inc.).

A strain with a phenotype of interest can be obtained by introducing a mutation through, for example, treatment involving the use of mutagens, such as N-methyl-N'-nitro-N-nitrosoguanidine or ethylmethane sulfonate, UV or radiation application, or spontaneous mutation. Alternatively, such strain can be obtained by cloning DNA of a region to which a mutation is to be introduced and introducing a mutation into DNA in vitro. When a large mutation of substitution is to be introduced, a plasmid carrying DNA to be substituted with a vector capable of replication in the strain is first constructed, and the plasmid is introduced into the strain, or the plasmid and chromosome DNA are subjected to homologous recombination in order to introduce a mutation of substitution. As long as a phenotype of interest appears, a mutation to be introduced may be substitution, deletion, or insertion of nucleotides, or it may be a mutation of substitution with a large DNA fragment. In addition, a mutation of one or more nucleotides is sufficient. Hereafter, a mutation is introduced in the manner described above, unless otherwise specified.

When it is necessary to regulate the gene expression level other than the promoter or transcription regulatory protein in the microorganism of the present invention, a distance between the ribosome-binding sequence and the translation initiation codon may be adjusted, a sequence in the vicinity of the translation initiation codon may be modified, or a nucleotide sequence in the translation region may be modified. Thus, the efficiency of the gene translation initiation can be regulated.

In general, DNA used for introduction of a mutation thus obtained is first inserted into a plasmid capable of replication in *Escherichia coli* and it is then introduced into a host strain, *Corynebacterium glutamicum*, by the method of DNA introduction described above. When the plasmid is a temperature-sensitive vector, a transformant resulting from single-crossover homologous recombination is selected via high-temperature culture. When the plasmid has an antibiotic-resistant marker, such as a kanamycin-resistant marker, which can be expressed in the host strain, a transformant resulting from single-crossover homologous recombination is selected based on the antibiotic resistance. In order to obtain a mutant in which DNA had been substituted via double-crossover homologous recombination in a chromosome region homologous to the DNA fragment, in general, a method involving the use of the levansucrase gene (the sacB gene) of the *Bacillus subtilis* 168 strain developed by W. Jäger et al. (J. Bacteriol. 174, 5462, 1992) can be employed. A strain is selected based on sucrose resistance. According to this method, *Corynebacterium glutamicum* in which the sacB gene of the *Bacillus subtilis* 168 strain is expressed is potentially lethal in a medium containing sucrose. Thus, a mutant that has lost the levansucrase gene via double-crossover homologous recombination can be selected based on sucrose resistance.

The microorganism of the present invention can be cultured in a general nutritive medium containing a carbon source, a nitrogen source, an inorganic salt, various vitamins, and the like. Examples of carbon sources include: saccharides, such as glucose, sucrose, and fructose; alcohols, such as ethanol and methanol; organic acids, such as citric acid, malic acid, and succinic acid; glycerol; and blackstrap molasses. Examples of nitrogen sources include ammonia, ammonium sulfate, ammonium chloride, ammonium nitrate, and urea, and these substances can be used alone or in combination. Examples of inorganic salts include potassium monohydrogen phosphate, potassium dihydrogen phosphate, and magnesium sulfate. In addition thereto, nutrients, such as peptone, meat extract, yeast extract, corn steep liquor, casamino acid, and various vitamins such as biotin, can be added to the medium.

Culture is generally conducted under aerobic conditions, such as aeration and agitation culture or shake culture conditions. Culture temperature is not particularly limited, provided that the microorganism of the present invention can grow. During culture, a pH level is not particularly limited, provided that the microorganism of the present invention can grow. During culture, a pH level can be adjusted with the addition of an acid or alkali.

After the completion of culture, the culture solution is subjected to centrifugation or other process, according to need, so as to remove insoluble components, such as bacteria, from the culture solution. Thereafter, the culture solution is subjected to, for example, extraction with an organic solvent such as ethyl acetate, a method involving the use of active carbon, a method involving the use of ion-exchange resin, precipitation via crystallization or salting out, or dilution. These techniques can be employed alone or in combination. Thus, an organic compound of interest can be obtained.

EXAMPLES

Hereafter, production of the microorganism of the present invention, which is the ATCC13032 strain that efficiently produces DHS as Compound P, and a method for producing DHS using such microorganism are described in greater detail with reference to the examples. In addition, production of the microorganism of the present invention, which is the ATCC13032 strain that efficiently produces protocatechuic acid as Compound Q, and a method for producing protocatechuic acid using such microorganism are described in greater detail with reference to the examples. It should be noted that the scope of the present invention is not limited to these examples.

Example 1

Comparison of DHS Productivity Between Pben-vanR Strain and NSHΔaroE3ΔqsuBΔqsuD Strain In the manner described below, the Pben-vanR strain, which had lost the capacity for converting DHS into protocatechuic acid as a result of mutation of in-frame deletion of the qsuB gene and in which aroE3 gene expression is repressed by the VanR repressor encoded by the vanR gene located downstream of the benA promoter (i.e., Reference Example 11), and the NSHΔaroE3ΔqsuBΔqsuD strain, which had lost the capacity for converting DHS into shikimic acid and the capacity for converting DHS into protocatechuic acid as a result of mutation of in-frame deletion of the qsuB gene, the qsuD gene, and the aroE3 gene (i.e., Reference Example 10), were cultured in a 3-liter jar fermenter, and DHS productivity was tested. The amount of DHS produced by such strains is improved from that of a wild-type strain because the transcription of the 4 types of genes (i.e., aroF, aroG, aroB, and aroD genes) associated with synthesis of DHS from DAHP is regulated by the Tu promoter.

As a medium used for preliminary preculture and preculture of these strains, CGXII medium (20 g/L ammonium sulfate, 5 g/L urea, 1 g/L potassium dihydrogen phosphate, 1 g/L dipotassium hydrogen phosphate, 0.25 g/L magnesium sulfate heptahydrate, 10 mg/L calcium chloride, 10 mg/L ferrous sulfate heptahydrate, 10 mg/L manganese sulfate pentahydrate, 1 mg/L zinc sulfate heptahydrate, 0.2 mg/L copper sulfate, 0.02 mg/L nickel chloride hexahydrate, 0.2 mg/L biotin, 20 g/L glucose, and 30 mg/L protocatechuic acid, pH 7.0) was used. The 1% preliminary preculture solution of the strains was inoculated into a preculture solution, and culture was then conducted at 30° C. for 24 hours. After the preculture solution was diluted with CGXII medium so as to adjust the absorbance at 600 nm to 3.0, 1% thereof was selectively inoculated into a medium for main culture (0.9 L) in a 3-liter jar fermenter (BMS-03NP2, manufactured by ABLE Corporation). As a medium for main culture, CGCF medium, which is CGXII medium containing 2.1 g/L anhydrous citric acid and 1.0 g/L ferrous sulfate 7H$_2$O, were used. Hereafter, the experiments for DHS and protocatechuic acid production were carried out in the manner described above, unless otherwise specified.

Since the NSHΔaroE3ΔqsuBΔqsuD strain grows very poorly in CGXII medium and CGCF medium, 0.5 g/L tryptophan, 0.4 g/L phenylalanine, 0.45 g/L tyrosine, 17 mg/L shikimic acid, 45 mg/L vitamin K2, and 14 mg/L p-aminobenzoic acid were added to these media, and culture was conducted therein. After the initiation of main culture, a culture solution was sampled at the appropriate time, diluted 1,000-fold with a 5% acetonitrile aqueous solution, and then analyzed via high-performance liquid chromatography (LCT Premier XE, manufactured by Waters) under the separation conditions shown in Table 1. Thereafter, the ratio of the DHS peak area relative to a DHS aqueous solution with a known concentration (DHS was purchased from Sigma) was determined. Hereafter, quantification of DHS was carried out in the manner described above.

Regarding the Pben-vanR strain, benzoic acid (final concentration: 5 mM) was added when the main culture was initiated, the addition of glucose at a rate of 4.0 g/hour was initiated 38 hours after the initiation of main culture, and culture was conducted for an additional 48 hours. Regarding the NSHΔaroE3ΔqsuBΔqsuD strain, the addition of glucose at a rate of 6.0 g/hour was initiated 45.5 hours after the initiation of main culture, and culture was conducted for an additional 16.5 hours. The amounts of DHS produced by the Pben-vanR strain and the NSHΔaroE3ΔqsuBΔqsuD strain were maximized 86 hours and 62 hours after the initiation of culture, respectively, and the maximal amounts of DHS produced by these strains were 15.4 g/L and 7.7 g/L, respectively. The results demonstrate that, even if the Pben-vanR strain in which aroE gene expression can be artificially regulated by the VanR repressor is cultured in a medium containing no aromatic amino acid, such strain would exhibit DHS productivity superior to that achieved by NSHΔaroE3ΔqsuBΔqsuD strain that has been cultured in a medium containing aromatic amino acid and the like.

TABLE 1

| HPLC analysis conditions for LCT Premier XE | |
|---|---|
| HPLC separation column | Acquity UPLC HSS Tc (i.d.: 2.1 mm; length: 50 mm, Waters) |
| Column temperature | 40° C. |
| Solvent flow rate | 0.4 ml/min |
| Mobile phase A | Water |
| Mobile phase B | Acetonitrile |
| Gradient conditions | 0 min (initiation) 2% Mobile phase B |
| | 0.75 min 5% Mobile phase B |
| | 1.75 min 30% Mobile phase B |
| | 1.76 min 5% Mobile phase B |
| | 2.50 min 5% Mobile phase B |

Example 2

Production of Protocatechuic Acid Using NSHΔaroE3 Strain and NSHΔaroE3_vanE3 Strain In the manner described below, the NSHΔaroE3 strain having a mutation of in-frame deletion in the aroE3 gene (see Reference Example 7) and the NSHΔaroE3_vanE3 strain modified therefrom in which aroE3 gene expression would be directed by the VanR repressor (see Reference Example 8) were cultured in a 3-liter jar fermenter, respectively, and the amounts of protocatechuic acid produced were compared.

The culture solution resulting from culture of these strains in the CGXII was diluted with CGXII medium sous to adjust the absorbance at 600 nm to 3.0, and 1% thereof was selectively inoculated into CGCF medium (0.9 L) in a 3-liter jar fermenter. Because of a mutation of aroE3 gene deletion, the NSHΔaroE3 strain grows very poorly in CGXII medium and CGCF medium. Thus, 50 mg/L tryptophan, 50 mg/L phenylalanine, 50 mg/L tyrosine, and 17 mg/L shikimic acid were added to these media, and culture was conducted therein. The addition of glucose at a rate of 2.0 g/hour was initiated 24 hours after the initiation of main culture, and culture was conducted for an additional 62.5 hours. After the initiation of main culture, a culture solution was sampled at the appropriate time, diluted 1,000-fold with a 5% acetonitrile aqueous solution, and then analyzed via high-performance liquid chromatography (LCT Premier XE, manufactured by Waters) under the separation conditions shown in Table 1. Thereafter, the ratio of the protocatechuic acid peak area relative to a protocatechuic acid aqueous solution with a known concentration (protocatechuic acid was purchased from Wako Pure Chemical Industries, Ltd.) was determined. Hereafter, quantification of protocatechuic acid was carried out in the manner described above. The results demonstrate that the amounts of protocatechuic acid produced by the NSHΔaroE3 strain and the NSHΔaroE3_vanE3 strain were maximized 48 hours and 62.5 hours after the initiation of culture, respectively, and the maximal amounts of protocatechuic acid produced by these strains were 0.5 g/L and 16.6 g/L, respectively. If a strain in which aroE gene expression is regulated by the VanR repressor is cultured in a medium containing no aromatic amino acid or shikimic acid, accordingly, such strain was found to produce protocatechuic acid in an amount about 33 times greater than the amount of protocatechuic acid produced by the NSHΔaroE3 strain, which had been cultured in a medium containing aromatic amino acid and shikimic acid.

Example 3

Production of Protocatechuic Acid Using NSHΔaroE3_vanE3 Strain, NSHΔaroE3_vanE3ΔqsuB_Pben-qsuB Strain, and NSHΔaroE3_vanE3ΔqsuB_Pben-qsuB-vanR Strain In the manner described below, the NSHΔaroE3_vanE3 strain (see Reference Example 8), the NSHΔaroE3_vanE3ΔqsuB_Pben-qsuB strain that had been modified to induce qsuB gene expression with the addition of benzoic acid (see Reference Example 12), and the NSHΔaroE3_vanE3ΔqsuB_Pben-qsuB-vanR that had been modified to induce qsuB gene and vanR gene expression with the addition of benzoic acid (see Reference Example 13) were cultured in a 3-liter jar fermenter, respectively, and the amounts of protocatechuic acid produced were compared. Regarding the NSHΔaroE3_vanE3ΔqsuB_Pben-qsuB strain, benzoic acid (final concentration: 5 mM) was added 14.5 hours after the initiation of main culture so as to induce qsuB gene expression. Regarding the NSHΔaroE3_vanE3ΔqsuB_Pben-qsuB-vanR strain, benzoic acid (final concentration: 5 mM) was added 15.5 hours after the initiation of main culture so as to induce qsuB gene and vanR gene expression. Regarding the NSHΔaroE3_vanE3ΔqsuB_Pben-qsuB strain, the NSHΔaroE3_vanE3ΔqsuB_Pben-qsuB-vanR strain, and the NSHΔaroE3_vanE3 strain, the addition of glucose at a rate of 3.5 g/hour was initiated 14.5 hours, 15.5 hours, and 18.5 hours after the initiation of main culture, respectively, and culture was terminated 62 hours after the initiation of main culture. The results demonstrate that the amounts of protocatechuic acid produced by the NSHΔaroE3_vanE3 strain, the NSHΔaroE3_vanE3ΔqsuB_Pben-qsuB strain, and the NSHΔaroE3_vanE3ΔqsuB_Pben-qsuB-vanR strain were maximized 43.8 hours, 43.8 hours, and 38.5 hours after the initiation of culture, respectively, and the maximal amounts of protocatechuic acid produced by these strains were 8.5 g/L, 8.6 g/L, and 15.2 g/L, respectively. As a result, a strain in which aroE3 gene expression would be directed by the VanR repressor was found to be capable of accumulating a significant amount of protocatechuic acid. Also, protocatechuic acid productivity was found to be improved by potentiating repression of aroE3 gene expression by increasing the amount of VanR repressor.

Example 4

Production of Protocatechuic Acid Using NSHΔaroE3_vanE3ΔqsuB_Pben-qsuB-vanR Strain and tkt Strain In the manner described below, the NSHΔaroE3_vanE3ΔqsuB_Pben-qsuB-vanR strain (Reference Example 13) and the tkt strain modified therefrom via enhanced transketolase expression (Reference Example 14) were cultured in a 3-liter jar fermenter, respectively, and the amounts of protocatechuic acid produced were compared. Regarding both the strains, benzoic acid (final concentration: 5 mM) was added 17 hours after the initiation of main culture, the addition of glucose at a rate of 4.5 g/hour was initiated 24 hours after the initiation of main culture, and culture was terminated 64 hours after the initiation of culture. The results demonstrate that the amounts of protocatechuic acid produced by the NSHΔaroE3_vanE3ΔqsuB_Pben-qsuB-vanR strain and the tkt strain were maximized 40 hours and 45 hours after the initiation of culture, respectively, and the maximal amounts of protocatechuic acid produced by these strains were 14.8 g/L and 20.0 g/L, respectively. As a result, protocatechuic acid productivity was found to improve through enhanced transketolase expression, in addition to regulation of aroE gene expression by the VanR repressor.

Example 5

Production of Protocatechuic Acid Using RhcR Repressor Regulatory System

In the production experiments conducted in the examples above, aroE3 gene expression was directed by the VanR repressor. In this example, differences in protocatechuic acid productivity were inspected on the basis of the occurrence of induction of nagI promoter transcription in the manner described below, with the use of the Pnag-qsuB-rhcR strain (Reference Example 17) in which aroE3 gene expression would be directed by the RhcR repressor instead of the VanR repressor and qsuB gene and rhcR gene expression would be directed by the nagI promoter. When nagI promoter transcription of the Pnag-qsuB-rhcR strain was to be induced, 3-hydroxybenzoic acid was added to a concentration of 5 mM 16.5 hours after the initiation of main culture, the addition of glucose at a rate of 4.9 g/hour was initiated 20.5 hours after the initiation of main culture, and culture was terminated 62.5 hours after the initiation of culture. When nagI promoter transcription of the Pnag-qsuB-rhcR strain was not to be induced, 3-hydroxybenzoic acid was not added, and culture was terminated 62.5 hours after the initiation of culture. The results demonstrate that the amounts of protocatechuic acid produced by the Pnag-qsuB-rhcR strain in which nagI promoter transcription had been induced and the Pnag-qsuB-rhcR in which nagI promoter transcription had not been induced were maximized 47.5 hours and 43.5 hours after the initiation of culture, respectively, and the maximal amounts of protocatechuic acid produced by these strains were 11.2 g/L and 8.4 g/L, respectively. The results demonstrate that a significant amount of protocatechuic acid would be produced when aroE3 gene and qsuB gene expression was directed by the RhcR repressor. Also, protocatechuic acid productivity was found to improve through an increased amount of RhcR repressor at the late culture stage.

Reference Example 1

Construction of pHCG298 E. coli-Corynebacterium Shuttle Vector

The Corynebacterium glutamicum ATCC13058 strain carrying the pHM1519 plasmid was obtained from NITE and the pHM1519 plasmid was isolated in accordance with a conventional technique. Subsequently, two types of DNAs (SEQ ID NOs: 1 and 2) were synthesized in order to add the BglII and NcoI restriction enzyme sites to the pHSG298 E. coli vector (manufactured by Takara Bio Inc.) carrying the kanamycin-resistant gene that functions in the ATCC13032 strain. These DNAs were inserted into a site between the KpnI site and the PstI site of pHSG298, so as to construct the pHSG298BN plasmid. Subsequently, a BglII fragment of about 3.1 kb containing a plasmid replication region was cleaved from the pHM1519 plasmid via BglII digestion, and the cleaved fragment was inserted into the BglII site of pHSG298BN, so as to construct the pHCG100 plasmid. After pHCG100 was digested with the BglII and NcoI restriction enzymes, the ends cleaved with the restriction enzymes were blunt-ended with the use of the Blunting High Kit (manufactured by Toyobo Co., Ltd.). After a BglII (blunt-ended)-NcoI (blunt-ended) fragment of about 1.9 kb derived from pHCG100 was purified, and the fragment was inserted into the StuI site of pHSG298, so that a pHCG298 E. coli-Corynebacterium shuttle vector was constructed.

Reference Example 2

Construction of pHKPsacB1 Plasmid for Levansucrase Constitutive Expression

The pHKPsacB1 plasmid constitutively expressing the levansucrase gene used when incorporating a target DNA region into a particular chromosome region of bacteria of the genus Corynebacterium via double-crossover homologous recombination was constructed in the manner described below.
1. Cloning of Levansucrase Gene
In order to select a strain into which the target DNA region had been incorporated into a particular chromosome region via double-crossover homologous recombination, the sacB gene of the Bacillus subtilis 168 strain encoding levansucrase that would become toxic to the host cell was used as a selection marker. The Bacillus subtilis 168 strain was obtained as the IAM2118 strain from the Japan Collection of Microorganisms, the Institute of Physical and Chemical Research. Also, the genome sequence information for the Bacillus subtilis 168 strain (GB Accession Number: NC_000964) was obtained from NCBI through the interne. Chromosome DNA of the Bacillus subtilis 168 strain was purified using the chromosome DNA extraction kit (manufactured by RBC Bioscience). PCR was carried out using 100 ng of chromosome DNA as a template and two types of DNA primers (SEQ ID NOs: 3 and 4) to obtain an amplified DNA fragment containing the sacB gene. Subsequently, the residue A was added to the 3' end of the amplified DNA fragment using Taq DNA polymerase. The amplified DNA fragment was subjected to gel electrophoresis, recovered, purified, and then incorporated into the pT7Blue-T vector. Thus, the pTBSACB1 plasmid carrying the sacB gene was constructed.
2. Construction of pHKPsacB1 Plasmid
After 8 synthetic DNAs shown in SEQ ID NOs: 5 to 12 were synthesized, the resulting synthetic DNAs were incorporated into the pT7Blue-T vector. Thus, the pTRKD2 plasmid constitutively expressing the sacB gene was constructed. Subsequently, the sacB gene region on the pTB-SACB1 plasmid obtained in 1. above was digested with restriction enzymes, HindIII and KpnI, and restriction enzymes, KpnI and XbaI, and a 1.0-kb HindIII-KpnI fragment and a 0.4-kb KpnI-XbaI fragment derived from the sacB genes were obtained. These two DNA fragments were inserted into a site between the SphI site and the XbaI site of the pHSG298 E. coli cloning vector (Takara Bio., Co. Ltd.) together with the pTRKD2-derived 0.2-kb HindIII-SphI fragment obtained above. Thus, the pHKPsacB1 plasmid for constitutive expression of the sacB gene was constructed. When the pHKPsacB1 plasmid transports DNA that is highly homologous to chromosome DNA of bacteria of the genus Corynebacterium, homologous recombination takes place between chromosome DNA and the plasmid, and the entire plasmid is incorporated into the chromosome. Thus, the resulting strain exhibits kanamycin-resistant and sucrose-sensitive phenotypes. Thereafter, a plasmid-derived DNA region is eliminated from the chromosome upon double-crossover homologous recombination. As a result, the strain exhibits kanamycin-sensitive and sucrose-resistant phenotypes.

Reference Example 3

Production of HT23 Strain Via Disruption of DNA Modification/Restriction Enzyme Gene of ATCC13032 Strain 1. Construction of Plasmid for Disruption of DNA Modification/Restriction Enzyme Gene
In the manner described below, the HT23 strain was produced from the ATCC13032 strain through disruption of a DNA modification/restriction enzyme gene. The ATCC13032 strain was obtained as the NBRC12168 strain from NITE. The nucleotide numbers shown in the examples below are the nucleotide numbers of the genome sequence of the ATCC13032 strain, and the genome sequence information was obtained under Accession Number NC_006958 from the NCBI GB database through the internet. Bacteria of the genus Corynebacterium including the ATCC13032 strain were cultured in CGYE medium (20 g/L ammonium sulfate, 5 g/L urea, 1 g/L KH2PO4, 1 g/L K2HPO4, 0.25 g/L MgSO4.7H2O, 1 g/L yeast extract, 10 mg/L CaCl2, 10 mg/L FeSO4.7H2O, 10 mg/L MnSO4.5H2O, 1 mg/L ZnSO4.7H2O, 0.2 mg/L CuSO4, 0.02 mg/L NiCl2.6H2O, 0.2 mg/L biotin, and 20 g/L glucose, pH 7), unless otherwise specified.

The cglIM (cg1996) gene encoding a DNA modification enzyme of the ATCC13032 strain (nucleotide numbers: 1,879,784 to 1,880,875) and the cglIR (cg1997) gene (nucleotide numbers: 1,880,884 to 1,881,960) and the cglIIR (cg1998) gene (nucleotide numbers: 1,881,962 to 1,883,860) encoding two restriction enzymes are successively present on the genome. In order to delete the expression of these 3 genes, a part of chromosome DNA of the strain (nucleotide numbers: 1,879,784 to 1,883,860) was disrupted in the manner described below.

In order to amplify the 5' flanking region of the DNA modification/restriction enzyme gene (nucleotide numbers: 1,878,625 to 1,879,745), two types of primers (SEQ ID NOs: 13 and 14) were synthesized. PCR was carried out using chromosome DNA of the ATCC13032 strain as a template and the primers prepared above, so as to amplify the 5' flanking region. After the residue A was added to the 3' end of the amplified DNA fragment using Taq DNA polymerase, the amplified DNA fragment was purified via gel electrophoresis, and the resultant was incorporated into the pT7Blue-T vector. Thus, the pTUSR1F plasmid carrying the 5' flanking region was constructed. In order to amplify the 3' flanking region of the DNA modification/restriction enzyme gene (nucleotide numbers: 1,883,891 to 1,885,298), subsequently, two types of primers (SEQ ID NOs: 15 and 16) were synthesized. PCR was carried out using chromosome DNA of the ATCC13032 strain as a template and the primers prepared above, so as to amplify the 3' flanking region. After the residue A was added to the 3' end of the amplified DNA fragment using Taq DNA polymerase, the amplified DNA fragment was purified via gel electrophoresis, and the resultant was incorporated into the pT7Blue-T vector. Thus, the pTDSR1R plasmid carrying the 3' flanking region was constructed. Subsequently, a BamHI-XhoI fragment of about 1.1 kb containing the 5' flanking region was prepared from the pTUSR1F plasmid. Also, an XbaI-XhoI fragment of about 1.4 kb containing the 3' flanking region was prepared from the pTUSR1R plasmid. Further, a BamHI-SphI fragment of about 1.6 kb containing a region for constitutive expression of the sacB gene was prepared from the pHKPsacB1 plasmid (Reference Example 2-2). These three fragments were inserted a site between the BamHI site and the XbaI site of the pHSG298 *E. coli* cloning vector. Thus, the pHKSD0977-9 plasmid for disruption of DNA modification/restriction enzyme gene was constructed.

2. Production of Mutant Strain Via Disruption of DNA Modification/Restriction Enzyme Gene Through a transformation technique via electroporation, the pHKSD0977-9 plasmid was introduced into the ATCC13032 strain, and the SCR strain was selected on the basis of kanamycin resistance. The SCR strain was analyzed via PCR using the primers (SEQ ID NOs: 13 and 16) and the primers for sacB gene confirmation (SEQ ID NOs: 3 and 4), and the results as expected were obtained. Thus, the SCR strain was found to be a transformant resulting from single-crossover homologous recombination in which the pHKSD0977-9 plasmid had been introduced into the region of DNA modification/restriction enzyme gene.

The SCR strain was cultured in 1 mL of LB liquid medium (10 g/l trypton, 5 g/l yeast extract, and 10 g/l sodium chloride) for 24 hours, a part of the culture solution was applied to LB agar medium containing 10% sucrose, and culture was conducted therein. Thus, the HT23 strain was obtained. Through PCR using the primers (SEQ ID NOs: 13 and 14), the HT23 strain was found to be a transformant resulting from double-crossover homologous recombination that had been deprived of the DNA modification/restriction enzyme gene, as expected.

Reference Example 4

Production of Mutant Strain Via pcaH.pcaG Gene Disruption

In the manner described below, the DRHG strain lacking a part of chromosome DNA of the ATCC13032 strain (nucleotide numbers of the complementary strand: 2,511,382 to 2,512,700) was produced from the HT23 strain produced in Reference Example 3, in order to disrupt the pcaH.pcaG gene encoding protocatechuate 4,5-dioxygenase.

1. Construction of Plasmid for pcaH.pcaG Gene Disruption

In order to amplify the 5' flanking region of the pcaH.pcaG gene of the HT23 strain (nucleotide numbers: 2,512,743 to 2,513,990), two types of primers (SEQ ID NOs: 17 and 18) were synthesized. PCR was carried out using chromosome DNA (100 ng) of the HT23 strain as a template and the primers prepared above, so as to amplify the 5' flanking region. After the residue A was added to the 3' end of the amplified DNA fragment using Taq DNA polymerase, subsequently, the amplified DNA fragment was purified via gel electrophoresis, and the resultant was incorporated into the pT7Blue-T vector (manufactured by Novagen). Thus, the pTPCAUSR1F plasmid carrying the 5' flanking region was constructed. Similarly, two types of primers (SEQ ID NOs: 19 and 20) for amplifying the 3' flanking region of the HT23 strain (nucleotide numbers of the complementary strand: 2,510,015 to 2,511,377) were synthesized. PCR was carried out using the purified chromosome DNA of the HT23 strain as a template and the primers prepared above, so as to amplify the 3' flanking region. After the residue A was added to the 3' end of the amplified DNA fragment using Taq DNA polymerase, the amplified DNA fragment was purified via gel electrophoresis, and the resultant was incorporated into the pT7Blue-T vector. Thus, the pTPCADSR1R plasmid carrying the 3' flanking region was constructed. Subsequently, an EcoRI-MluI fragment of about 1.3 kb containing the 5' flanking region was prepared from pTPCAUSR1F via digestion with restriction enzymes. Also, a MluI-BamHI fragment of about 1.4 kb containing the 3' flanking region was prepared from pTPCADSR1R via digestion with restriction enzymes. Further, a BamHI-SphI fragment of about 1.6 kb containing the sacB gene region was prepared from the pHKPsacB1 plasmid (see Reference Example 2) via digestion with restriction enzymes. Thereafter, these 3 fragments were inserted into a region between the EcoRI site and the SphI site of the pHSG298 *E. coli* cloning vector. Thus, the pHKSDPHG1 plasmid for gene disruption was constructed.

2. Production of DRHG Strain

Through a transformation technique via electroporation, the pHKSDPHG1 plasmid was introduced into the HT23 strain, and the SCRHG strain was selected on the basis of kanamycin resistance. The SCRHG strain was analyzed via PCR using the primers (SEQ ID NOs: 21 and 22) and the primers for sacB gene confirmation (SEQ ID NOs: 3 and 4), and the results as expected were obtained. Thus, the SCRHG strain was found to be a transformant resulting from single-crossover homologous recombination in which the pHKSDPHG1 plasmid had been introduced into the pcaH.pcaG gene region.

The SCRHG strain was cultured in 1 mL of LB liquid medium for 24 hours, a part of the culture solution was applied to LB agar medium containing 10% sucrose, and culture was conducted therein. Thus, the DRHG strain was obtained. Through PCR using a set of primers (SEQ ID NOs: 23 and 24), the DRHG strain was found to be a transformant resulting from double-crossover homologous recombination that had been deprived of the pcaH.pcaG gene, as expected. Separately, PCR was carried out using the primers (SEQ ID NOs: 25 and 26), and no amplified DNA fragment was obtained. Thus, the DRHG strain was also found to lack the sacB gene.

Reference Example 5

Production of Mutant Strain Via pobB Gene Disruption

In order to disrupt the pobB gene encoding p-hydroxybenzoate hydroxygenase and suppress production of gallic acid from protocatechuic acid, the DRHG145 strain lacking a part of chromosome DNA (nucleotide numbers of the complementary strand: 1,126,301 to 1,127,488b) was produced from the DRHG strain produced in Reference Example 4 in the manner described below.
1. Construction of Plasmid for pobB Gene Disruption In order to amplify the 3' flanking region of the pobB gene (nucleotide numbers: 1,125,101 to 1,126,300) and add the SphI and XbaI restriction enzyme sites to the both ends of the amplified fragment, two types of DNA primers (SEQ ID NOs: 27 and 28) were synthesized. PCR was carried out using chromosome DNA of the DRHG strain as a template and the primers prepared above, so as to amplify the 3' flanking region of the pobB gene. In order to amplify the 5' flanking region of the pobB gene (nucleotide numbers: 1,127,505 to 1,128,687) and add the XbaI and SalI restriction enzyme sites to the both ends of the amplified fragment, subsequently, two types of DNA primers (SEQ ID NOs: 29 and 30) were synthesized. PCR was carried out using chromosome DNA of the DRHG strain as a template and the primers prepared above, so as to amplify the 5' flanking region of the pobB gene. The amplified DNA fragment of the 3' flanking region was digested with the SphI and XbaI restriction enzymes, the amplified DNA fragment of the 5' flanking region was digested with the XbaI and SalI restriction enzymes, and these DNA fragments were introduced into a site between the SphI site and the SalI site in the multicloning site of the pHKPsacB1 plasmid (see Reference Example 2). Thus, the pHKPsacBΔpobB plasmid was obtained.
2. Production of Mutant Strain Via pobB Gene Disruption Through a transformation technique via electroporation, the pHKPsacBΔpobB plasmid was introduced into the DRHG strain, and the DRHG_Km strain was selected on the basis of kanamycin resistance. The DRHG_Km strain was analyzed via PCR using the primers (SEQ ID NOs: 27 and 30) and the primers for sacB gene confirmation (SEQ ID NOs: 3 and 4), and the results as expected were obtained. Thus, the DRHG_Km strain was found to be a transformant resulting from single-crossover homologous recombination in which the pHKPsacBΔpobB plasmid had been introduced into the pobB gene region.

The DRHG_Km strain was cultured in 1 mL of LB liquid medium for 24 hours, a part of the culture solution was applied to LB agar medium containing 10% sucrose, and culture was conducted therein. Thus, the DRHG145 strain was obtained. Through PCR using a set of primers (SEQ ID NOs: 27 and 30), the DRHG145 strain was found to be a transformant resulting from double-crossover homologous recombination that had been deprived of the pobB gene, as expected.

Reference Example 6

Production of NSH Strain in which Transcription of aroF, aroG, aroB, and aroD Genes is Directed by Tu Promoter In the 4 processes described below, transcription of 4 types of genes associated with synthesis of DHS from DAHP (i.e., aroF, aroG, aroB, and aroD genes) were directed by the Tu promoter of the ATCC13032 strain (nucleotide numbers: 526,013 to 526,374). Thus, the NSH strain with improved DHS productivity was produced.
1. Production of NUA Strain Via Substitution of Promoters of qsuB Gene, aroD Gene, and qsuD Gene, Respectively, with Tu Promoter The qsuB gene, the aroD gene, and the qsuD gene of the ATCC13032 strain constitute an operon (hereafter referred to as the aro operon), and the expression levels thereof are regulated by the same regulator (i.e., the cg0500 gene product). On the basis of the DRHG145 strain produced in Reference Example 5, the NUA strain was produced by substituting the promoter region of the aro operon (nucleotide numbers: 441,597 to 442,756) with the Tu promoter having high transcription activity in the manner described below.
(1) Construction of Plasmid for Substitution of aro Promoter Region of cg0500 Gene with Tu Promoter In order to amplify the 5' flanking region of the cg0500 gene (nucleotide numbers: 440,437 to 441,596) and add the SphI and RsrII restriction enzyme sites to the both ends of the amplified fragment, two types of primers (SEQ ID NOs: 31 and 32) were synthesized. In order to amplify the 3' flanking region of the aro promoter (nucleotide numbers: 442,757 to 443,916) and add the PfoI and SbfI restriction enzyme sites to the both ends of the amplified fragment, two types of primers (SEQ ID NOs: 33 and 34) were synthesized. In order to amplify the Tu promoter region and add the RsrII and PfoI restriction enzyme sites to the both ends of the amplified fragment, two types of primers (SEQ ID NOs: 35 and 36) were synthesized. PCR was carried out using chromosome DNA of the DRHG strain as a template and the 3 sets of primers, so as to amplify the 5' flanking region of the cg0500 gene, the 3' flanking region of the aro operon promoter region, and the Tu promoter region.

The amplified DNA fragment of the 5' flanking region of the cg0500 gene was digested with the SphI and RsrII restriction enzymes, the amplified DNA fragment of the 3' flanking region of the aro operon promoter region was digested with the PfoI and SbfI restriction enzymes, and the amplified DNA fragment of the Tu promoter was digested with the RsrII and PfoI restriction enzymes. Thereafter, the 3 types of DNA fragments obtained via restriction enzyme treatment were introduced into a site between the SbfI site and the SphI site in the multicloning site of the pHKPsacB1 plasmid (see Reference Example 2). Thus, the pHKPsacB_aro-Ntu plasmid was obtained.
(2) Production of Homologous Recombinant Using pHKPsacB_Aro-Ntu Plasmid Through a transformation technique via electroporation, pHKPsacB_Ntu-aro was introduced into the DRHG145 strain, and the DRHG145_Km strain was selected on the basis of kanamycin resistance. The DRHG145_Km strain was analyzed via PCR using the primers (SEQ ID NOs: 31 and 34) and the primers for sacB gene confirmation (SEQ ID NOs: 3 and 4), and the results as expected were obtained. Thus, the DRHG145_Km strain was found to be a transformant resulting from single-crossover homologous recombination in which the pHKPsacB_Ntu-aro plasmid had been introduced into the cg0500 gene region.

The DRHG145_Km strain was cultured in 1 mL of LB liquid medium for 24 hours, a part of the culture solution was applied to LB agar medium containing 10% sucrose, and culture was conducted therein. Thus, the NUA strain was obtained. The primer shown in SEQ ID NO: 37 was synthesized. PCR was carried out using a set of primers (SEQ ID NOs: 37 and 36) and a set of primers (SEQ ID NOs: 31 and 34), and the DRHG145 strain was found to be a transformant resulting from double-crossover homologous recombination in which the cg0500 gene and the aro promoter had each been substituted with the Tu promoter, as expected.

2. Production of NDSGU Strain Via Substitution of aroG Gene Promoter with Tu Promoter The promoter region of the aroG gene encoding DAHP synthase was substituted with the Tu promoter region so as to produce the NDSGU strain from the NUA strain in the manner described below.

(1) Construction of Plasmid for Substitution of aroG Promoter

In order to amplify the 5' flanking region of the aroG gene promoter (nucleotide numbers of the complementary strand: 2,280,842 to 2,282,206) and add the SphI and RsrII restriction enzyme sites to the both ends of the amplified fragment, two types of primers (SEQ ID NOs: 38 and 39) were synthesized. In order to amplify the 3' flanking region of the aroG gene promoter (nucleotide numbers of the complementary strand: 2,279,366 to 2,280,754) and add the PfoI and SbfI restriction enzyme sites to the both ends of the amplified fragment, two types of primers (SEQ ID NOs: 40 and 41) were synthesized. Further, PCR was carried out using chromosome DNA of the DRHG strain as a template and the primers prepared above, so as to amplify the 5' flanking region and the 3' flanking region of the aroG gene promoter, respectively. Separately, PCR was carried out using chromosome DNA of the DRHG strain as a template and the primers (SEQ ID NOs: 35 and 36), so as to amplify the Tu promoter.

The amplified DNA fragment of the 5' flanking region of the aroG gene promoter was digested with the SphI and RsrII restriction enzymes, the amplified DNA fragment of the 3' flanking region of the aroG gene promoter was digested with the PfoI and SbfI restriction enzymes, and the amplified DNA fragment of the Tu promoter was digested with the RsrII and PfoI restriction enzymes. Thereafter, the 3 types of DNA fragments obtained via restriction enzyme treatment were introduced into a site between the SbfI site and the SphI site in the multicloning site of the pHKPsacB1 plasmid (see Reference Example 2). Thus, the pHKPsacB_aroG-Ntu plasmid was obtained.

(2) Production of Homologous Recombinant Using pHKPsacB_aroG-Ntu Plasmid

Through a transformation technique via electroporation, the pHKPsacB_aroG-Ntu plasmid was introduced into the NUA strain, and the NUA_Km strain was selected on the basis of kanamycin resistance. The NUA_Km strain was analyzed via PCR using the primers (SEQ ID NOs: 38 and 41) and the primers for sacB gene confirmation (SEQ ID NOs: 3 and 4), and the results as expected were obtained. Thus, the NUA_Km strain was found to be a transformant resulting from single-crossover homologous recombination in which the pHKPsacB_aroG-Ntu plasmid had been introduced into the aroG gene region.

The NUA_Km strain was cultured in 1 mL of LB liquid medium for 24 hours, a part of the culture solution was applied to LB agar medium containing 10% sucrose, and culture was conducted therein. Thus, the NDSGU strain was obtained. PCR was carried out using the primers (SEQ ID NOs: 38 and 41) and the primers (SEQ ID NOs: 35 and 36), and the NDSGU strain was found to be a transformant resulting from double-crossover homologous recombination in which the aroG promoter region had been substituted with Tu promoter, as expected. Further, the DNA primer located outside the 5' flanking region (SEQ ID NO: 42) and the DNA primer located outside the 3' flanking region (SEQ ID NO: 43) of the aroG gene were synthesized. Separately, PCR was carried out using the primers prepared above, and the NDSGU strain was found to be a transformant resulting from double-crossover homologous recombination in which the aroG promoter region had been substituted with Tu promoter.

3. Production of NSU Strain Via Substitution of aroB Gene Promoter with Tu Promoter The NSU strain was produced from the NDSGU strain in the manner described below via substitution of a promoter region of the aroB gene encoding DHQ synthetase with the Tu promoter region.

(1) Construction of Plasmid for Substitution of aroB Promoter

In order to amplify the 5' flanking region of the aroB gene promoter (nucleotide numbers of the complementary strand: 1,720,573 to 1,721,670) and add the SphI and RsrII restriction enzyme sites to the both ends of the amplified fragment, two types of primers (SEQ ID NOs: 44 and 45) were synthesized. In order to amplify the 3' flanking region of the aroB gene promoter (nucleotide numbers of the complementary strand: 1,719,404 to 1,720,501) and add the PfoI and SbfI restriction enzyme sites to the both ends of the amplified fragment, two types of primers (SEQ ID NOs: 46 and 47) were synthesized. Further, PCR was carried out using chromosome DNA of the DRHG strain as a template and the primers prepared above, so as to amplify the 5' flanking region and the 3' flanking region of the aroB gene promoter, respectively. Separately, PCR was carried out using chromosome DNA of the DRHG strain as a template and the primers (SEQ ID NOs: 35 and 16), so as to amplify the Tu promoter.

The amplified DNA fragment of the 5' flanking region of the aroB gene promoter was digested with the SphI and RsrII restriction enzymes, the amplified DNA fragment of the 3' flanking region of the aroB gene promoter was digested with the PfoI and SbfI restriction enzymes, and the amplified DNA fragment of the Tu promoter was digested with the RsrII and PfoI restriction enzymes. Thereafter, the 3 types of DNA fragments obtained via restriction enzyme treatment were introduced into a site between the SbfI site and the SphI site in the multicloning site of the pHKPsacB1 plasmid (see Reference Example 2). Thus, the pHKPsacB_aroB-Ntu plasmid was obtained.

(2) Production of Homologous Recombinant Using pHKPsacB_aroB-Ntu Plasmid

Through a transformation technique via electroporation, the pHKPsacB_aroB-Ntu plasmid was introduced into the NDSGU strain, and the NDSGU_Km strain was selected on the basis of kanamycin resistance. In order to confirm that the NDSGU_Km strain is a transformant of interest resulting from single-crossover homologous recombination, two types of primers (SEQ ID NOs: 48 and 49) were synthesized based on an upstream fragment of the 5' flanking region and a downstream fragment of the 3' flanking region of the aroB gene promoter. The NDSGU_Km strain was analyzed by PCR using chromosome DNA of the NDSGU_Km strain as a template, the primers (SEQ ID NOs: 48 and 49), the primers (SEQ ID NOs: 35 and 36), and the primers for sacB gene confirmation (SEQ ID NOs: 3 and 4), and the results as expected were obtained. Thus, the NDSGU_Km strain was found to be a transformant resulting from single-crossover homologous recombination in which the pHKPsacB_aroB-Ntu plasmid had been introduced into the aroB gene region.

The NDSGU_Km strain was cultured in 1 mL of LB liquid medium for 24 hours, a part of the culture solution was applied to LB agar medium containing 10% sucrose, and culture was conducted therein. Thus, the NSU strain was obtained. PCR was carried out using the primers (SEQ ID NOs: 44 and 47), the primers (SEQ ID NOs: 48 and 49), and the primers (SEQ ID NOs: 35 and 36), and the NSU strain was found to be a transformant resulting from double-crossover homologous recombination in which the aroB promoter region had been substituted with Tu promoter, as expected.

4. Production of NSH Strain Via Substitution of aroF Gene Promoter with Tu Promoter The NSH strain was produced from the NSH strain in the manner described below via substitution of a promoter region of the aroF gene encoding DHQ synthetase with the Tu promoter region.

(1) Construction of Plasmid for Substitution of aroF Promoter

In order to amplify the 5' flanking region of the aroF gene promoter (nucleotide numbers of the complementary strand: 1,046,619 to 1,047,863) and add the SphI and RsrII restriction enzyme sites to the both ends of the amplified fragment, two types of primers (SEQ ID NOs: 50 and 51) were synthesized. In order to amplify the 3' flanking region of the aroF gene promoter (nucleotide numbers of the complementary strand: 1,046,619 to 1,047,863) and add the PfoI and SbfI restriction enzyme sites to the both ends of the amplified fragment, two types of primers (SEQ ID NOs: 52 and 53) were synthesized. Further, PCR was carried out using chromosome DNA of the DRHG strain as a template and the primers prepared above, so as to amplify the 5' flanking region and the 3' flanking region of the aroF gene promoter, respectively. Separately, PCR was carried out using chromosome DNA of the DRHG strain as a template and the primers (SEQ ID NOs: 35 and 36), so as to amplify the Tu promoter.

The amplified DNA fragment of the 5' flanking region of the aroF gene promoter was digested with the SphI and RsrII restriction enzymes, the amplified DNA fragment of the 3' flanking region of the aroF gene promoter was digested with the PfoI and SbfI restriction enzymes, and the amplified DNA fragment of the Tu promoter was digested with the RsrII and PfoI restriction enzymes. Thereafter, the 3 types of DNA fragments obtained via restriction enzyme treatment were introduced into a site between the SbfI site and the SphI site in the multicloning site of the pHKPsacB1 plasmid (see Reference Example 2). Thus, the pHKPsacB_aroF-Ntu plasmid was obtained.

(2) Production of Homologous Recombinant Using pHKPsacB_aroF-Ntu Plasmid

Through a transformation technique via electroporation, the pHKPsacB_aroF-Ntu plasmid was introduced into the NSU strain, and the NSU_Km strain was selected on the basis of kanamycin resistance. In order to confirm that the NSU_Km strain is a transformant of interest resulting from single-crossover homologous recombination, two types of primers (SEQ ID NOs: 54 and 55) were synthesized based on an upstream fragment of the 5' flanking region and a downstream fragment of the 3' flanking region of the aroF gene promoter. The NSU_Km strain was analyzed by PCR using chromosome DNA of the NSU_Km strain as a template, the primers (SEQ ID NOs: 54 and 55), the primers (SEQ ID NOs: 35 and 36), and the primers for sacB gene confirmation (SEQ ID NOs: 3 and 4), and the results as expected were obtained. Thus, the NSU_Km strain was found to be a transformant resulting from single-crossover homologous recombination in which the pHKPsacB_aroF-Ntu plasmid had been introduced into the aroF gene region.

The NSU_Km strain was cultured in 1 mL of LB liquid medium for 24 hours, a part of the culture solution was applied to LB agar medium containing 10% sucrose, and culture was conducted therein. Thus, the NSH strain was obtained. PCR was carried out using the primers (SEQ ID NOs: 50 and 53), the primers (SEQ ID NOs: 54 and 55), and the primers (SEQ ID NOs: 35 and 36), and the NSU strain was found to be a transformant resulting from double-crossover homologous recombination in which the aroB promoter region had been substituted with Tu promoter, as expected.

Reference Example 7

Production of Mutant Strain Via in-Frame Disruption of aroE1 Gene and aroE3 Gene Encoding Shikimate Dehydrogenase A mutation of in-frame deletion was introduced into the aroE1 gene and the aroE3 gene, which may affect the growth, among the 3 types of shikimate dehydrogenases carried by the ATCC13032 strain, so as to prepare a mutant strain in the manner described below (hereafter, such mutant strain is occasionally referred to as an "strain with in-frame disruption"). The term "mutation of in-frame deletion;" that is, the term "in-frame disruption," refers to a mutation resulting from introduction of a deletion of a number of nucleotides that is a multiple of three into the translation region.

1. Construction of Plasmid for in-Frame Disruption of aroE1 Gene

In order to amplify the 5' flanking region of the aroE1 gene (nucleotide numbers: 1,183,128 to 1,184,160), two types of DNA primers (SEQ ID NOs: 56 and 57) were synthesized. The SphI restriction enzyme site was introduced into the primer shown in SEQ ID NO: 56. PCR was carried out using chromosome DNA of the DRHG strain as a template and the primers prepared above, so as to amplify the 5' flanking region of the aroE1 gene. Subsequently, two types of DNA primers (SEQ ID NOs: 58 and 59) were synthesized in order to amplify the 3' flanking region of the aroE1 gene promoter (nucleotide numbers: 1,181,390 to 1,182,365). The SbfI restriction enzyme site was introduced into the primer shown in SEQ ID NO: 59.

Amplified DNA of the 5' flanking region and amplified DNA of the 3' flanking region of the aroE1 gene thus obtained were mixed with each other. The resulting mixture as a template was amplified via overlap PCR using the DNA primers (SEQ ID NOs: 56 and 59), and the resultant was then digested with the SphI and SbfI restriction enzymes. The resulting DNA fragment was introduced into a site between the SbfI site and the SphI site in the multicloning site of the pHKPsacB1 plasmid (see Reference Example 2). Thus, the pHKPsacBΔaroE1 plasmid was obtained. The pHKPsacBΔaroE1 plasmid was deprived of a region comprising nucleotides 1,181,390 to 1,184,160 of the complementary strand from the aroE1 gene region.

2. Production of Mutant Strain Via in-Frame Disruption of aroE1 Gene

Through a transformation technique via electroporation, the pHKPsacBΔaroE1 plasmid was introduced into the NSH strain, and the NSH_Km strain was selected on the basis of kanamycin resistance. In order to confirm that the NSH_Km strain is a transformant of interest resulting from single-crossover homologous recombination, two types of primers (SEQ ID NOs: 60 and 61) were synthesized based on an upstream fragment of the 5' flanking region and a downstream fragment of the 3' flanking region of the aroE1 gene. The NSH_Km strain was analyzed by PCR using the primers (SEQ ID NOs: 56 and 59) and the primers for sacB gene confirmation (SEQ ID NOs: 3 and 4), and the results as expected were obtained. Thus, the NSH_Km strain was found to be a transformant resulting from single-crossover homologous recombination in which the pHKPsacBΔaroE1 plasmid had been introduced into the aroE1 gene region.

The NSH_Km strain was cultured in 1 mL of LB liquid medium for 24 hours, a part of the culture solution was applied to LB agar medium containing 10% sucrose, and culture was conducted therein. Thus, the NSHΔaroE1 strain was obtained. PCR was carried out using the primers (SEQ ID NOs: 60 and 61), and the NSHΔaroE1 strain was found to be a transformant resulting from double-crossover homologous recombination that had been deprived of the aroE1 gene, as expected.

3. Construction of Plasmid for in-Frame Disruption of aroE3 Gene

In order to amplify the 5' flanking region of the aroE3 gene (nucleotide numbers: 1,726,887 to 1,727,845), two types of DNA primers (SEQ ID NOs: 62 and 63) were synthesized. The SphI restriction enzyme site was introduced into the primer shown in SEQ ID NO: 62. PCR was carried out using chromosome DNA of the DRHG strain as a template and the primers prepared above, so as to amplify the 5' flanking region of the aroE3 gene. Subsequently, two types of DNA primers (SEQ ID NOs: 64 and 65) were synthesized in order to amplify the 3' flanking region of the aroE3 gene (nucleotide numbers: 1,725,101 to 1,726,094). The SbfI restriction enzyme site was introduced into the primer shown in SEQ ID NO: 65. Amplified DNA of the 5' flanking region and amplified DNA of the 3' flanking region of the aroE3 gene thus obtained were mixed with each other. The resulting mixture as a template was amplified via overlap PCR using the DNA primers (SEQ ID NOs: 62 and 65), and the resultant was then digested with the SphI and SbfI restriction enzymes. The resulting DNA fragment was introduced into a site between the SbfI site and the SphI site in the multicloning site of the pHKPsacB1 plasmid (see Reference Example 2). Thus, the pHKPsacBΔaroE3 plasmid was obtained. The pHKPsacBΔaroE3 plasmid was deprived of a region comprising nucleotides 1,726,095 to 1,726,886 of the complementary strand from the aroE3 gene region.

4. Production of Mutant Strain Via in-Frame Disruption of aroE3 Gene

Through a transformation technique via electroporation, the pHKPsacBΔaroE3 plasmid was introduced into the NSH strain, and the NSH_Km2 strain was selected on the basis of kanamycin resistance. In order to confirm that the NSH_Km2 strain is a transformant of interest resulting from single-crossover homologous recombination, two types of primers (SEQ ID NOs: 66 and 67) were synthesized based on an upstream fragment of the 5' flanking region and a downstream fragment of the 3' flanking region of the aroE3 gene. The NSH_Km strain was analyzed by PCR using the primers (SEQ ID NOs: 62 and 65), the primers (SEQ ID NOs: 66 and 67), and the primers for sacB gene confirmation (SEQ ID NOs: 3 and 4), and the results as expected were obtained. Thus, the NSH_Km2 strain was found to be a transformant resulting from single-crossover homologous recombination in which the pHKPsacBΔaroE3 plasmid had been introduced into the aroE3 gene region.

The NSH_Km2 strain was cultured in 1 mL of LB liquid medium for 24 hours, a part of the culture solution was applied to LB agar medium containing 10% sucrose, and culture was conducted therein. Thus, the NSHΔaroE3 strain was obtained. PCR was carried out using the primers (SEQ ID NOs: 66 and 67), and the NSHΔaroE3 strain was found to be a transformant resulting from double-crossover homologous recombination that had been deprived of the aroE3 gene, as expected.

5. Production of Mutant Strain Via Double Disruption of aroE1 Gene and aroE3 Gene In the same manner as described in "Production of mutant strain via in-frame disruption of aroE3 gene" above, a strain with a double disruption was produced from the NSHΔaroE1 strain through in-frame disruption of the aroE3 gene (the resulting strain was designated to be the "NSHΔaroE1ΔaroE3 strain").

6. Test for Aromatic Amino Acid Auxotrophy of NSHΔaroE1 Strain, NSHΔaroE3 Strain, and NSHΔaroE1ΔaroE3 Strain The NSH strain, the NSHΔaroE1 strain, the NSHΔaroE3 strain, and the NSHΔaroE1ΔaroE3 strain produced in the manner described above were tested for aromatic amino acid auxotrophy in the manner described below.

The strains were inoculated into LB medium for preculture, culture was conducted at 30° C. overnight, and 2% of the culture product was transferred to CGXII medium. Another culture experiment was simultaneously conducted in a medium prepared by adding shikimic acid, tryptophan, phenylalanine, and tyrosine to the CGXII medium at the final concentration of 50 mg/L each. As a result, the NSH strain and the NSHΔaroE1 strain were found to grow normally in CGXII medium while the NSHΔaroE3 strain and the NSHΔaroE1ΔaroE3 strain did not grow therein. Also, the NSHΔaroE3 strain and the NSHΔaroE1ΔaroE3 strain were found to regain the growth ability with the addition of shikimic acid, tryptophan, phenylalanine, and tyrosine to CGXII medium. Thus, the aroE3 gene was found to be a main gene encoding shikimate dehydrogenase.

Reference Example 8

Production of NSHΔaroE3_vanE3 Strain that Produces Protocatechuic Acid in which aroE3 Gene Expression is Directed by vanA Promoter The genes encoding vanillic acid demethylase of the ATCC13032 strain are the cg2616 gene (hereafter abbreviated to as the "vanA gene;" nucleotide numbers 2,496,775 to 2,497,905; 1,131 bp) and the cg2617 gene (hereafter abbreviated to as the "vanB gene;" nucleotides numbers 2,497,909 to 2,498,886; 978 bp). A region comprising nucleotides 2,496,775 to 2,498,886 is abbreviated to as the "vanAB gene region." A known repressor that regulates the vanA gene and the vanB gene is the cg2615 gene (hereafter abbreviated to as the "vanR gene;" nucleotide numbers 2,496,013 to 2,496, 591 of the complementary strand; 579 bp). The aroE3 gene was introduced into the vanA gene region and the vanB gene region with the aid of the vanR gene, and the aroE3 gene was substituted in a region downstream of the vanR gene. The NSHΔaroE3 strain as described in Reference Example 7 was used as a parent strain.

1. Construction of Vector for Substitution of vanAB Gene Region with aroE3 Gene

In order to substitute the vanAB gene region of the ATCC13032 strain with the aroE3 gene, a vector for substitution was constructed in the manner described below. At the outset, two types of DNA primers (SEQ ID NOs: 68 and 69) were synthesized, in order to amplify the 5' flanking region of the vanAB gene region (nucleotide numbers: 2,495,799 to 2,496,774; size 976 kp) on the basis of the genome sequence of the ATCC13032 strain. In order to amplify the 3' flanking region of the vanAB gene region (nucleotide numbers: 2,498,887 to 2,499,870; 984 kp), two types of primers (SEQ ID NOs: 70 and 71) were synthesized. PCR was carried out using the primers prepared above and chromosome DNA of the NSH strain as a template, so as to amplify the 5' flanking region of the vanAB gene and the 3' flanking region of the vanAB gene. The 5' flanking region of the vanAB gene was amplified, and the SphI restriction enzyme site was introduced into the DNA primer (SEQ ID NO: 68). The 3' flanking region of the vanAB gene was amplified, and the SbfI restriction enzyme site was introduced into the DNA primer (SEQ ID NO: 71). Also, two types of primers (SEQ ID NOs: 72 and 73) were synthesized in order to amplify the aroE3 gene. The aroE3 gene was amplified, a 3'-terminal 15-bp region of the 5' flanking region of the vanAB gene region was added to the DNA primer (SEQ ID NO: 72), and the 5' terminal 15-bp region of the 3' flanking region of the vanAB gene region was added to the DNA primer (SEQ ID NO: 73), followed by amplification. The amplified 5' flanking region was mixed with the aroE3 gene. The resulting DNA fragment, as a template, was amplified by overlap PCR using the DNA primers (SEQ ID NOs: 68 and 73). Alternatively, the amplified 3' flanking region was mixed with the aroE3 gene, and the resulting DNA fragment, as a template, was amplified by overlap PCR using the DNA primers (SEQ ID NOs: 72 and 71). The amplified DNA fragments were digested with the SphI restriction enzyme in combination with the internal restriction enzyme site, AscI, of the aroE3 gene and the SbfI restriction enzyme in combination with the internal restriction enzyme site, AscI, of the aroE3 gene, respectively. The resultants were introduced into a site between the SbfI site and the SpltI site in the multicloning site of the pHKPsacB1 plasmid (see Reference Example 2). Thus, the pHKPsacB_vanR_Pvan-aroE3 plasmid was obtained.

2. Production of Mutant Strain Via Substitution of vanAB Gene Region with aroE3 Gene Through a transformation technique via electroporation, the pHKPsacB_vanR_Pvan-aroE3 plasmid was introduced into the NSHΔaroE3 strain, and the kanamycin-resistant NSHΔaroE3 strain was obtained. In order to confirm that a region comprising nucleotides 2,496,775 to 2,498,886 in a region (nucleotide numbers: 2,495,799 to 2,499,870; 4,071 bp) on chromosome DNA of the obtained kanamycin-resistant strain has been substituted with the aroE3 gene, the following experiment was carried out. The DNA primers (SEQ ID NOs: 74 and 75) were produced in a 112-bp region outside the 5' flanking region and a 106-bp region outside the 3' flanking region of the vanAB gene. With the use of these DNA primers and the DNA primers used for amplification of the 5' flanking region and the 3' flanking region of the vanAB gene (SEQ ID NOs: 68 and 71), PCR was carried out using, as a direct template, a colony of the kanamycin-resistant NSHΔaroE3 strain. The size of the amplified DNA fragment obtained by PCR in which chromosome DNA of the kanamycin-resistant NSHΔaroE3 strain as a template was amplified with the aid of the DNA primers (SEQ ID NOs: 74 and 71) was 4,194 bp, and the size of the amplified DNA fragment obtained by PCR in which amplification was carried out with the use of the DNA primers (SEQ ID NOs: 68 and 75) was 2,905 bp. Or, the size of the amplified DNA fragment obtained by PCR in which amplification was carried out with the use of the DNA primers (SEQ ID NOs: 74 and 71) was 2,913 bp, and the size of the amplified DNA fragment obtained by PCR in which amplification was carried out with the aid of the DNA primers (SEQ ID NOs: 68 and 75) was 4,186 bp. Since the sacB gene region was detected via PCR or other analysis, the NSHΔaroE3 strain was found to be a transformant resulting from single-crossover homologous recombination.

A transformant resulting from single-crossover homologous recombination of the NSHΔaroE3 strain was cultured in 1 mL of LB liquid medium for 24 hours, a small amount of the culture product was applied to LB agar medium containing 10% sucrose, and culture was conducted therein. In the chromosome DNA of the grown NSHΔaroE3 strain, it was predicted that the sacB gene region, the kanamycin-resistant gene region, and the vanAB gene region were substituted with the aroE3 gene, respectively, and the strain was designated to be the NSHΔaroE3_vanE3 strain. The NSHΔaroE3_vanE3 strain was subjected to PCR using two types of DNA primers (SEQ ID NOs: 74 and 75) and found to be a transformant resulting from double-crossover homologous recombination in which the vanAB gene region had been substituted with the aroE3 gene, as expected.

3. Confirmation of Growth of NSHΔaroE3_vanE3 Strain

With the use of CGXII medium supplemented with 17.5 mg/L shikimic acid, 50 mg/L tryptophan, 50 mg/L phenylalanine, 50 mg/L tyrosine, 10 mg/L p-hydroxybenzoic acid, and 10 mg/L p-aminobenzoic acid (hereafter referred to as "6 types of additives") and CGXII medium not supplemented with the 6 types of additives, the growth conditions of the NSHΔaroE3_vanE3 strain and the NSHΔaroE3 strain were examined. While the NSHΔaroE3_vanE3 strain was found to grow normally in the former medium, the growth rate thereof was slow up to the middle culture stage in the latter medium. While the NSHΔaroE3 strain was found to grow in the former medium, it did not grow in the latter medium. When the NSHΔaroE3_vanE3 strain was cultured in a medium prepared by adding ferulic acid, vanillic acid, or vanillin in an amount of 50 μM or more to the CGXII medium not supplemented with the 6 types of additives, the NSHΔaroE3_vanE3 strain was found to grow normally.

Reference Example 9

Production of Mutant Strain Via in-Frame Disruption of DHS Dehydratase Gene

A mutation of in-frame deletion was introduced into the qsuB gene of the NSH strain, the NSHΔaroE3 strain, and the NSHΔaroE3_vanE3 strain described in Reference Examples 6, 7, and 8, respectively, as parent strains, and strains in which conversion of DHS into protocatechuic acid was blocked were produced in the manner described below.

1. Construction of Plasmid for qsuB Gene Disruption

In order to amplify the 5' flanking region of the qsuB gene (nucleotide numbers: 443,184 to 444,207) and add the SbfI and XbaI restriction enzyme sites to the both ends of the amplified fragment, two types of DNA primers (SEQ ID NOs: 76 and 77) were synthesized. In order to amplify the 3' flanking region of the qsuB gene (nucleotide numbers: 446,032 to 447,053) and add the XbaI and SalI restriction enzyme sites to the both ends of the amplified fragment, also, two types of DNA primers (SEQ ID NOs: 78 and 79) were synthesized. PCR was carried out using chromosome DNA of the NSH strain as a template and the primers prepared above, so as to amplify the 5' flanking region and the 3' flanking region of the qsuB gene. The amplified product of the 5' flanking region was digested with the SbfI and XbaI restriction enzymes, and the amplified product of the 3' flanking region was digested with the XbaI and SalI restriction enzymes. Thereafter, these DNA fragments were introduced into a site between the SbfI site and the SalI site in the multicloning site of the pHKPsacB1 plasmid (see Reference Example 2). Thus, the pHKPsacBΔqsuB plasmid for qsuB gene disruption was obtained.

2. Production of Mutant Strain Via qsuB Gene Disruption

The pHKPsacBΔqsuB plasmid was introduced into the NSH strain, the NSHΔaroE3 strain, and the NSHΔaroE3_vanE3 strain, respectively, and the NSH_qsuB_Km strain, the NSHΔaroE3_qsuB_Km strain, and the NSHΔaroE3_vanE3_qsuB_Km strain were selected on the basis of kanamycin resistance. In order to analyze the obtained strains by PCR, the DNA primer identical to the upstream sequence of the 5' flanking region (SEQ ID NO: 80) and the DNA primer identical to the downstream sequence of the 3' flanking region (SEQ ID NO: 81) of the qsuB gene were synthesized. PCR was carried out using a set of primers (SEQ ID NOs: 79 and 80) and a set of primers (SEQ ID NOs: 76 and 81). The results as expected were obtained via PCR analysis using either set of primers. Thus, these strains were found to be transformants resulting from single-crossover homologous recombination in which the pHKPsacBΔqsuB plasmid had been introduced into the qsuB gene region.

The NSHΔqsuB_Km strain, the NSHΔaroE3ΔqsuB_Km strain, and the NSHΔaroE3_vanE3ΔqsuB_Km strain were cultured in 1 mL of LB liquid medium for 24 hours, respectively, a part of the culture solution was applied to LB agar medium containing 10% sucrose, and culture was conducted therein. Thus, the NSHΔqsuB strain, the NSHΔaroE3ΔqsuB strain, and the NSHΔaroE3_vanE3ΔqsuB strain were obtained therefrom, respectively. PCR was carried out using the primers (SEQ ID NOs: 80 and 81) and the primers for sacB gene confirmation (SEQ ID NOs: 3 and 4), and these strains were found to be transformants resulting from double-crossover homologous recombination that had been deprived of a region comprising nucleotides 444,208 to 446,031 in the qsuB gene.

Reference Example 10

Production of Mutant Strain Via in-Frame Disruption of Shikimic Acid Dehydratase Gene Mutant strains were produced as described below from the NSHΔaroE3ΔqsuB strain and the NSHΔaroE3_vanE3ΔqsuB strain via introduction of a mutation of in-frame deletion into the qsuD gene encoding shikimic acid dehydratase, in order to lower activity of remaining shikimic acid dehydratase.

1. Construction of Plasmid for in-Frame Disruption of qsnD Gene

In order to amplify the 5' flanking region of the qsuD gene (nucleotide numbers: 443,644 to 446,553; a region comprising nucleotides 444,199 to 446,031 is a region of in-frame disruption of the qsuB gene), two types of DNA primers (SEQ ID NOs: 82 and 83) were synthesized. The SbfI restriction enzyme site was introduced into the primer shown in SEQ ID NO: 82. PCR was carried out using chromosome DNA of the NSHΔqsuB strain as a template and the primers prepared above, so as to amplify the 5' flanking region of the qsuD gene. Subsequently, two types of DNA primers (SEQ ID NOs: 84 and 85) were synthesized in order to amplify the 3' flanking region of the qsuD gene promoter (nucleotide numbers: 447,385 to 448,441). The XhoI restriction enzyme site was introduced into the primer shown in SEQ ID NO: 85. Amplified DNA of the 5' flanking region and amplified DNA of the 3' flanking region of the aroE gene thus obtained were mixed with each other. The resulting mixture as a template was amplified via overlap PCR using the DNA primers (SEQ ID NOs: 82 and 85), and the resultant was then digested with the SbfI and XhoI restriction enzymes. The resulting DNA fragment was introduced into a site between the SbfI site and the SphI site in the multicloning site of the pHKPsacB1 plasmid (see Reference Example 2). Thus, the pHKPsacBΔqsuD plasmid was obtained. The pHKPsacBΔqsuD plasmid was deprived of a region comprising nucleotides 446,554 to 447,384 from the qsuD gene region.

2. Production of Mutant Strain Via in-Frame Disruption of qsuD Gene

Through a transformation technique via electroporation, the pHKPsacBΔqsuD plasmid was introduced into the NSHΔaroE3qsuB strain and the NSHΔaroE3_vanE3ΔqsuB strain, and the NSHΔaroE3ΔqsuB_Km strain and NSHΔaroE3_vanE3ΔqsuB_km strain were selected on the basis of kanamycin resistance. In order to confirm that the NSHΔaroE3ΔqsuB_Km strain and the NSHΔaroE3_vanE3ΔqsuB_kin strain are transformants of interest resulting from single-crossover homologous recombination, two types of primers (SEQ ID NOs: 86 and 87) were synthesized based on an upstream fragment of the 5' flanking region and a downstream fragment of the 3' flanking region of the qsuD gene. The NSHΔaroE3ΔΔqsuB_Km strain and the NSHΔaroE3_vanE3ΔqsuB3_km strain were analyzed by PCR using the primers (SEQ ID NOs: 86 and 85), the primers (SEQ ID NOs: 82 and 87), and the primers for sacB gene confirmation (SEQ ID NOs: 3 and 4), and the results as expected were obtained. Thus, the NSHΔaroE3ΔqsuB_Km strain and the NSHΔaroE3_vanE3ΔqsuB_km strain were found to be transformants resulting from single-crossover homologous recombination in which the pHKPsacBΔqsuD plasmid had been introduced into the qsuD gene region.

The NSHΔaroE3ΔqsuB_Km strain and the NSHΔaroE3_vanE3ΔqsuB_km strain were cultured in 1 mL of LB liquid medium for 24 hours, respectively, a part of the culture solution was applied to LB agar medium containing 10% sucrose, and culture was conducted therein. Thus, the NSHΔaroE3ΔqsuBΔqsuD strain and the NSHΔaroE3_vanE3ΔqsuBΔqsuD strain were obtained. PCR was carried out using the primers (SEQ ID NOs: 86 and 87), and the NSHΔaroE3ΔqsuBΔaroE strain and the NSHΔaroE3_vanE3ΔqsuBΔqsuD strain were found to be transformants resulting from double-crossover homologous recombination that had been deprived of the aroE gene, as expected.

3. Test for Aromatic Amino Acid Auxotrophy of NSHΔaroE3ΔqsuBΔqsuD Strain

The NSH strain, the NSHΔaroE3 strain, the NSHΔaroE3ΔqsuB strain, the NSHΔaroE3ΔqsuBΔaroE1 strain, the NSHΔaroE3_vanE3ΔqsuB strain, and the NSHΔaroE3ΔqsuBΔqsuD strain produced in the manner described above were tested for aromatic amino acid auxotrophy in the manner described below.

The strains were inoculated into CGXII medium for preculture supplemented with 17.5 mg/L shikimic acid, 50 mg/L tryptophan, 50 mg/L phenylalanine, and 50 mg/L tyrosine, culture was conducted at 30° C. overnight, and the cultured strains were washed twice and then transferred to CGXII medium for main culture while adjusting. OD 600 at about 0.05. Another culture experiment was simultaneously conducted in a medium prepared by adding 17.5 mg/L shikimic acid; 50 mg/L tryptophan, 50 mg/L phenylalanine, and 50 mg/L tyrosine to the CGXII medium for main culture. As a result, only the NSHΔaroE3ΔqsuBΔqsuD strain among the NSH strain, the NSHΔaroE3 strain, the NSHΔaroE3ΔqsuB strain, the NSHΔaroE3ΔqsuBΔaroE1 strain, the NSHΔaroE3_vanE3ΔqsuB strain, and the NSHΔaroE3ΔqsuBΔqsuD strain was found to grow only when shikimic acid, tryptophan, phenylalanine, and tyrosine were added. This indicates that activity of remaining shikimic acid dehydratase is substantially quenched by deletion of the qsuD gene.

Reference Example 11

Production of DHS-Producing Strain Capable of Regulating aroE3 Gene Expression by Induction of VanR Repressor Expression The benABCD gene region of the NSHΔaroE3_vanE3ΔqsuBΔqsuD strain produced in Reference Example 10 was substituted with the vanR gene. Thus, a mutant strain in which vanR gene expression would be directed by the benA promoter was produced.

1. Construction of Plasmid for Substitution of benABCD Gene Region with vanR Gene In order to amplify the 5' flanking region of the benABCD gene region (nucleotide numbers: 2,515,963 to 2,516,969), two types of DNA primers (SEQ ID NOs: 88 and 89) were synthesized. In order to amplify the 3' flanking region of the benABCD gene region (nucleotide numbers: 2,521,372 to 2,522,498), also, two types of DNA primers (SEQ ID NOs: 90 and 91) were synthesized. The primers shown in SEQ ID NOs: 88 and 91 each comprise the SalI and SbfI restriction enzyme sites. PCR was carried out using chromosome DNA of the HT23 strain (Reference Example 3) as a template and the primers prepared above, so as to amplify the 5' flanking region and the 3' flanking region of the benABCD gene. In order to amplify the vanR gene, further, two types of DNA primers (SEQ ID NOs: 92 and 93) were synthesized. PCR was carried out using chromosome DNA of the HT23 strain as a template and the primers (SEQ ID NOs: 92 and 93), so as to amplify the vanR gene region. Amplified DNA of the 5' flanking region of the benABCD gene thus obtained and amplified DNA of the qsuB gene region were mixed with each other. The resulting mixture as a template was amplified via overlap PCR using the primers (SEQ ID NOs: 88 and 93), and the resultant was then digested with the SalI and NarI restriction enzymes. Thus, a DNA fragment cleaved with the SalI site in the primer (SEQ ID NO: 88) and the NarI site in the vanR gene was obtained. Also, amplified DNA of the vanR gene region was mixed with amplified DNA of the 3' flanking region of the benABCD gene. The resulting mixture as a template was amplified via overlap PCR using the primers (SEQ ID NOs: 91 and 92), and the resultant was then digested with the NarI and SbfI restriction enzymes. Thus, a DNA fragment cleaved with the NarI site in the vanR gene and the SbfI site in the primer (SEQ ID NO: 91) was obtained. These 2 types of DNA fragments were introduced into a site between the SalI site and the SbfI site in the multicloning site of the pHKPsacB1 plasmid (see Reference Example 2). Thus, the pHKPsacB_Pben-vanR plasmid was obtained.

2. Production of Mutant Strain Via Substitution of benABCD Gene Region with vanR Gene Through a transformation technique via electroporation, the pHKPsacB_Pben-vanR plasmid was introduced into the NSHΔaroE3_vanE3ΔqsuBΔqsuD strain, and the kanamycin-resistant NSHΔaroE3_vanE3ΔqsuBΔqsuD_Km strain was obtained. In order to analyze the NSHΔaroE3_vanE3ΔqsuBΔqsuD_Km strain by PCR, subsequently, the primer identical to the upstream sequence of the 5' flanking region (SEQ ID NO: 94) and the primer identical to the downstream sequence of the 3' flanking region (SEQ ID NO: 95) of the vanR gene were synthesized. Thereafter, the NSHΔaroE3_vanE3ΔqsuBΔqsuD_Km strain was analyzed by PCR using the primers (SEQ ID NOs: 94 and 91) and the primers (SEQ ID NOs: 88 and 95). The results as expected were obtained via PCR analysis using either set of primers. Thus, the NSHΔaroE3_vanE3ΔqsuBΔqsuD_Km strain was found to be a transformant resulting from single-crossover homologous recombination in which the pHKPsacB_Pben-vanR plasmid had been introduced into the benABCD gene region.

The NSHΔaroE3_vanE3ΔqsuBΔqsuD_Km strain was cultured in 1 mL of LB liquid medium for 24 hours, a part of the culture solution was applied to LB agar medium containing 10% sucrose, and culture was conducted therein. Thus, the Pben-vanR strain was obtained. PCR was carried out using the primers (SEQ ID NOs: 94 and 95), and the Pben-vanR strain was found to be a transformant resulting from double-crossover homologous recombination in which the benABCD gene region had been substituted with the vanR gene.

Reference Example 12

Production of NSHΔaroE3_vanE3ΔqsuB_Pben-qsuB Strain Producing Protocatechuic Acid in which qsuB Gene Expression is Directed by benA Promoter In the manner described below, the benABCD gene operon region of the NSHΔaroE3_vanE3ΔqsuB strain produced in Reference Example 9 was substituted with the qsuB gene. Thus, a mutant strain in which qsuB gene expression would be directed by the benA promoter was produced.

1. Construction of Plasmid for Substitution of benABCD Gene Region with qsuB Gene In order to amplify the 5' flanking region of the benABCD gene region, two types of DNA primers (SEQ ID NOs: 88 and 89) were used, and two types of DNA primers (SEQ ID NOs: 90 and 91) were used in order to amplify the 3' flanking region of the benABCD gene region. PCR was carried out using chromosome DNA of the HT23 strain (Reference Example 3) as a template and the primers prepared above, so as to amplify the 5' flanking region and the 3' flanking region of the benABCD gene. Also, two types of DNA primers (SEQ ID NOs: 96 and 97) were synthesized in order to amplify the qsuB gene. PCR was carried out using chromosome DNA of the HT23 strain as a template and the primers prepared above, so as to amplify the qsuB gene region. Amplified DNA of the 5' flanking region of the benABCD gene and amplified DNA of the qsuB gene region thus obtained were mixed with each other. The resulting mixture as a template was amplified via overlap PCR using the primers (SEQ ID NOs: 88 and 97), and the resultant was then digested with the SalI and NarI restriction enzymes. Thus, a DNA fragment cleaved with the SalI site in the primer (SEQ ID NO: 88) and the NarI site in the qsuB gene was obtained. Also, amplified DNA of the qsuB gene region was mixed with amplified DNA of the 3' flanking region of the benABCD gene. The resulting mixture as a template was amplified via overlap PCR using the primers (SEQ ID NOs: 91 and 96), and the resultant was then digested with the NarI and SbfI restriction enzymes. Thus, a DNA fragment cleaved with the NarI site in the qsuB gene and the SbfI site in the primer (SEQ ID NO: 91) was obtained. These 2 types of DNA fragments were introduced into a site between the SalI site and the SbfI site in the multicloning site of the pHKPsacB1 plasmid (see Reference Example 2). Thus, the pHKPsacB_Pben-qsuB plasmid was obtained.

2. Production of Mutant Strain Via Substitution of ben-ABCD Gene Region with qsuB Gene Through a transformation technique via electroporation, the pHKPsacB_Pben-qsuB plasmid was introduced into the NSHΔaroE3_vanE3ΔqsuB strain, and the kanamycin-resistant NSHΔaroE3_vanE3ΔqsuB_Km strain was obtained. In order to analyze the NSHΔaroE3_vanE3ΔqsuB_Km strain by PCR, subsequently, the primer identical to the upstream sequence of the 5' flanking region (SEQ ID NO: 98) and the primer identical to the downstream sequence of the 3' flanking region (SEQ ID NO: 99) of the qsuB gene were synthesized. Thereafter, the NSHΔaroE3_vanE3ΔqsuB_Km strain was analyzed by PCR using the primers (SEQ ID NOs: 88 and 99) and the primers (SEQ ID NOs: 91 and 98). The results as expected were obtained via PCR analysis using either set of primers. Thus, the NSHΔaroE3_vanE3ΔqsuB_Km strain was found to be a transformant resulting from single-crossover homologous recombination in which the pHKPsacB_Pben-qsuB plasmid had been introduced into the benABCD gene region.

The NSHΔaroE3_vanE3ΔqsuB_Km strain was cultured in 1 mL of LB liquid medium for 24 hours, a part of the culture solution was applied to LB agar medium containing 10% sucrose, and culture was conducted therein. Thus, the NSHΔaroE3_vanE3ΔqsuB_Pben-qsuB strain was obtained. PCR was carried out using the primers (SEQ ID NOs: 88 and 99) and the primers (SEQ ID NOs: 91 and 98), and the NSHΔaroE3_vanE3ΔqsuB_Pben-qsuB strain was found to be a transformant resulting from double-crossover homologous recombination in which the benABCD gene region had been substituted with the qsuB gene.

Reference Example 13

Production of NSHΔaroE3_vanE3ΔqsuB_Pben-qsuB-vanR Strain Producing Protocatechuic Acid in which qsuB and vanR Gene Expression is Directed by benA Promoter The vanR gene was introduced into the NSHΔaroE3_vanE3ΔqsuB_Pben-qsuB strain produced in Reference Example 12 while allowing the vanR gene to constitute an operon with the qsuB gene. A mutant strain in which qsuB and vanR gene expression would be directed by the benA promoter because of the operon formed with the qsuB gene was produced in the manner described below.

1. Construction of Plasmid for Insertion of vanR Gene into Downstream of qsuB Gene In order to amplify the 5' flanking region of a region of vanR gene insertion (nucleotide numbers: 2,520,333 to 2,521,374), two types of DNA primers (SEQ ID NOs: 100 and 101) were synthesized. In order to amplify the 3' flanking region of a region of vanR gene insertion (nucleotide numbers: 2,521,372 to 2,522,498), also, two types of primers (SEQ ID NOs: 102 and 103) were synthesized. The primers shown in SEQ ID NOs: 100 and 103 each comprise the SalI and SbfI restriction enzyme sites. PCR was carried out using chromosome DNA of the NSHΔaroE3_vanE3ΔqsuB_Pben-qsuB strain as a template and the primers prepared above, so as to amplify the 5' flanking region and the 3' flanking region of the region of vanR gene insertion. In order to amplify the vanR gene, further, two types of DNA primers (SEQ ID NOs: 104 and 105) were synthesized. PCR was carried out using chromosome DNA of the HT23 strain (Reference Example 3) as a template and the primers prepared above, so as to amplify the vanR gene region. Amplified DNA of the 5' flanking region of the region of vanR gene insertion and amplified DNA of the vanR gene region thus obtained were mixed with each other. The resulting mixture as a template was amplified via overlap PCR using the primers (SEQ ID NOs: 100 and 105), and the resultant was then digested with the SalI and BamHI restriction enzymes. Thus, a DNA fragment cleaved with the San site in the primer (SEQ ID NO: 100) and the BamHI site in the vanR gene was obtained. Also, amplified DNA of the vanR gene region was mixed with amplified DNA of the 3' flanking region of the region of vanR gene insertion. The resulting mixture as a template was amplified via overlap PCR using the primers (SEQ ID NOs: 104 and 103), and the resultant was then digested with the BamHI and SbfI restriction enzymes. Thus, a DNA fragment cleaved with the BamHI site in the vanR gene and the SbfI site in the primer (SEQ ID NO: 103) was obtained. These 2 types of DNA fragments were introduced into a site between the SalI site and the SbfI site in the multicloning site of the pHKPsacB1 plasmid (see Reference Example 2). Thus, the pHKPsacB_Pben-qsuB-vanR plasmid was obtained.

2. Production of Mutant Strain Via Insertion of vanR Gene into Downstream of qsuB Gene Through a transformation technique via electroporation, the pHKPsacB_Pben-qsuB-vanR plasmid was introduced into the NSHΔaroE3_vanE3ΔqsuB_Pben-qsuB strain, and the kanamycin-resistant NSHΔaroE3_vanE3ΔqsuB_Pben-qsuB_Km strain was obtained. In order to analyze the NSHΔaroE3_vanE3ΔqsuB_Pben-qsuB_Km strain by PCR, subsequently, the primer identical to the upstream sequence of the 5' flanking region (SEQ ID NO: 106) and the primer identical to the downstream sequence of the 3' flanking region (SEQ ID NO: 107) of the region of vanR gene insertion were synthesized. Thereafter, the NSHΔaroE3_vanE3ΔqsuB_Pben-qsuB_Km strain was analyzed by PCR using the primers (SEQ ID NOs: 100 and 103). The results as expected were obtained via PCR analysis using either set of primers. Thus, the NSHΔaroE3_vanE3ΔqsuB_Pben-qsuB_Km strain was found to be a transformant resulting from single-crossover homologous recombination in which the pHKPsacB_Pben-qsuB-vanR plasmid had been introduced into the region of vanR gene insertion.

The NSHΔaroE3_vanE3ΔqsuB_Pben-qsuB_Km strain was cultured in 1 mL of LB liquid medium for 24 hours, a part of the culture solution was applied to LB agar medium containing 10% sucrose, and culture was conducted therein. Thus, the NSHΔaroE3_vanE3ΔqsuB_Pben-qsuB-vanR strain was obtained. PCR was carried out using the primers (SEQ ID NOs: 106 and 107). Thus, the NSHΔaroE3_vanE3ΔqsuB_Pben-qsuB-vanR strain was found to be a transformant resulting from double-crossover homologous recombination in which the vanR gene had been introduced into a downstream region of the qsuB gene in the benABCD gene region.

Reference Example 14

Production of tkt Strain Producing Protocatechuic Acid that Constitutively Expresses tkt Gene With the use of the NSHΔaroE3_vanE3ΔqsuB_Pben-qsuB-vanR strain produced in Reference Example 13 as the parent strain, the transcription unit comprising the tkt gene associated with synthesis of erythrose-4-phosphate ligated to the Tu promoter (Reference Example 6) (hereafter, abbreviated to as the "Ptu-tkt transcription unit") was inserted into the site of DNA modification/restriction enzyme gene disruption to produce the tkt strain in the manner described below.

1. Construction of Plasmid for Construction of Ptu-tkt Transcription Unit

In order to amplify the 5' flanking region of the site of DNA modification/restriction enzyme gene disruption (nucleotide numbers: 1,885,120 to 1,883,861), two types of DNA primers (SEQ ID NOs: 108 and 109) were synthesized. In order to amplify the 3' flanking region of the site of DNA modification/restriction enzyme gene disruption (nucleotide numbers: 1,879,744 to 1,878,664), also, two types of DNA primers (SEQ ID NOs: 110 and 111) were synthesized. Further, the DNA primers (SEQ ID NOs: 112 and 36) were synthesized in order to amplify the Tu promoter, and two types of DNA primers (SEQ ID NOs: 113 and 114) were synthesized in order to amplify the tkt gene. The primers shown in SEQ ID NOs: 108 and 111 each comprise the SbfI and SalI restriction enzyme sites.

PCR was carried out using chromosome DNA of the HT23 strain (Reference Example 3) as a template and the primers prepared above, so as to amplify the 5' flanking region and the 3' flanking region of the site of DNA modification/restriction enzyme gene disruption. Amplified DNA of the 5' flanking region was mixed with amplified DNA of the tkt gene. The resulting mixture as a template was amplified via overlap PCR using the primers (SEQ ID NOs: 108 and 113), and the resultant was then digested with the SbfI and PfoI restriction enzymes. Thus, a DNA fragment cleaved with the SbfI site in the primer (SEQ ID NO: 108) and the PfoI site in the primer (SEQ ID NO: 113) was obtained. Also, amplified DNA of the Tu promoter was mixed with amplified DNA of the 3' flanking region. The resulting mixture as a template was amplified via overlap PCR using the primers (SEQ ID NOs: 36 and 111), and the resultant was then digested with the PfoI and SalI restriction enzymes. Thus, a DNA fragment cleaved with the PfoI site in the primer (SEQ ID NO: 36) and the SalI site in the primer (SEQ ID NO: 111) was obtained. These 2 types of DNA fragments were introduced into a site between the SbfI site and the SalI site in the multicloning site of the pHKPsacB1 plasmid (see Reference Example 2). Thus, the pHKCPsacB_Ptu-tkt plasmid was obtained.

2. Production of Mutant Strain Comprising Ptu-tkt Transcription Unit Incorporated Therein Through a transformation technique via electroporation, the pHKPsacB_Ptu-tkt plasmid was introduced into the NSHΔaroE3_vanE3ΔqsuB_Pben-qsuB-vanR strain, and the kanamycin-resistant NSHΔaroE3_vanE3ΔqsuB_Pben-qsuB-vanR_Km strain was obtained. In order to analyze the NSHΔaroE3_vanE3ΔqsuB_Pben-qsuB-vanR_Km strain by PCR, subsequently, the primer identical to the upstream sequence of the 5' flanking region (SEQ ID NO: 115) and the primer identical to the downstream sequence of the 3' flanking region (SEQ ID NO: 116) were synthesized. Thereafter, the NSHΔaroE3_vanE3ΔqsuB_Pben-qsuB-vanR_Km strain was analyzed by PCR using the primers (SEQ ID NOs: 115 and 116) and the primers (SEQ ID NOs: 108 and 111). The results as expected were obtained via PCR analysis using either set of primers. Thus, the NSHΔaroE3_vanE3ΔqsuB_Pben-qsuB-vanR_Km strain was found to be a transformant resulting from single-crossover homologous recombination into which the pHKPsacB_Ptu-tkt plasmid had been introduced.

The NSHΔaroE3_vanE3ΔqsuB_Pben-qsuB-vanR_Km strain was cultured in 1 mL of LB liquid medium for 24 hours, a part of the culture solution was applied to LB agar medium containing 10% sucrose, and culture was conducted therein. Thus, the tkt strain was obtained. As a result of PCR using the primers (SEQ ID NOs: 115 and 116) and the primers (SEQ ID NOs: 108 and 111) and digestion of the amplified fragment with restriction enzymes, the strain was found to be a transformant resulting from double-crossover homologous recombination in which the Ptu-tkt transcription unit had been incorporated into the site of DNA modification/restriction enzyme gene disruption.

Reference Example 15

Production of Mutant Strain in which aroE3 Gene Expression is Directed by rhcH Promoter A region from the cg1309 gene to the cg1311 gene (hereafter, abbreviated to as the "rhcHMD gene region") was substituted with the aroE3 gene to produce a mutant strain in the manner described below.

1. Construction of Plasmid for genH Gene Disruption

In order to amplify the 5' flanking region (nucleotide numbers: 3,201,424 to 3,202,403) of the cg3354 gene encoding 3-hydroxybenzoate 6-hydroxylase (hereafter referred to as the genH gene) and add the KpnI and SbfI restriction enzyme sites to the both ends of the amplified fragment, two types of DNA primers (SEQ ID NOs: 117 and 118) were synthesized. PCR was carried out using chromosome DNA of the DRHG strain as a template and the primers prepared above, so as to amplify the 5' flanking region of the genH gene. In order to amplify the 3' flanking region of the genH gene (nucleotide numbers: 3,203,894 to 3,204,901) and add the SbfI and SalI restriction enzyme sites to the both ends of the amplified fragment, subsequently, two types of DNA primers (SEQ ID NOs: 119 and 120) were synthesized. PCR was carried out using chromosome DNA of the DRHG strain as a template and the primers prepared above, so as to amplify the 3' flanking region of the genH gene. The amplified DNA fragment of the 5' flanking region was digested with the KpnI and SbfI restriction enzymes, and the amplified DNA fragment of the 3' flanking region was digested with the SbfI and SalI restriction enzymes. Thereafter, these DNA fragments were introduced into a site between the KpnI site and the SalI site in the multicloning site of the pHKPsacB1 plasmid (see Reference Example 2). Thus, the pHKPsacBΔgenH plasmid was obtained.

2. Production of Mutant Strain Via genH Gene Disruption

Through a transformation technique via electroporation, the pHKPsacBΔgenH plasmid was introduced into the NSHΔaroE3 strain, and the NSHΔaroE3_Km strain was selected on the basis of kanamycin resistance. The NSHΔaroE3_Km strain was analyzed by PCR using the primers (SEQ ID NOs: 117 and 120) and the primers for sacB gene confirmation (SEQ ID NOs: 3 and 4), and the results as expected were obtained. Thus, the NSHΔaroE3_Km strain was found to be a transformant resulting from single-crossover homologous recombination in which the pHKPsacBΔgenH plasmid had been introduced into the genH gene region.

The NSHΔaroE3_Km strain was cultured in 1 mL of LB liquid medium for 24 hours, a part of the culture solution was applied to LB agar medium containing 10% sucrose, and culture was conducted therein. Thus, the NSHΔaroE3ΔgenH strain was obtained. As a result of PCR using the primers (SEQ ID NOs: 117 and 120), the NSHΔaroE3ΔgenH strain was found to be a transformant resulting from double-crossover homologous recombination that had been deprived of the genH gene, as expected.

3. Construction of Vector for Substitution of rhcHMD Gene Region with aroE3 Gene In order to amplify the 5' flanking region (nucleotide numbers: 1,213,341 to 1,214,736) of the rhcHMD gene region, two types of DNA primers (SEQ ID NOs: 121 and 122) were synthesized. The SbfI restriction enzyme site was introduced into the primer shown in SEQ ID NO: 121. PCR was carried out using chromosome DNA of the NSH strain as a template and the primers prepared above, so as to amplify the 5' flanking region of the rhcHMD gene region. In order to amplify the 3' flanking region (nucleotide numbers: 1,218,296 to 1,219,545) of the rhcHMD gene, subsequently, two types of DNA primers (SEQ ID NOs: 123 and 124) were synthesized. The SalI restriction enzyme site was introduced into the primer shown in SEQ ID NO: 124.

In order to amplify the aroE3 gene, also, DNA primers (SEQ ID NOs: 125 and 126) were synthesized. Amplified DNA fragments of the 5' flanking region of the rhcHMD gene region and the aroE3 gene as templates were amplified via overlap PCR using the DNA primers (SEQ ID NOs: 121 and 126). Amplified DNA fragments of the 3' flanking region and the aroE3 gene as templates were amplified via overlap PCR using the DNA primers (SEQ ID NOs: 125 and 124). The amplified DNA fragments were digested with restriction enzymes, SbfI in combination with AvrII or AvrII in combination with SalI, and the fragments were introduced into a site between the SbfI site and the SalI site in the multicloning site of the pHKPsacB1 plasmid (see Reference Example 2). Thus, the PHKPsacB_rhcR_Prhc-rhcE3 plasmid was obtained.

4. Production of Mutant Strain Via Substitution of rhcHMD Gene Region with aroE3 Gene Through a transformation technique via electroporation, the pHKPsacB_rhcR_Prhc-rhcE3 plasmid was introduced into the NSHΔaroE3ΔgenH strain, and the NSHΔaroE3ΔgenH_Km strain was selected on the basis of kanamycin resistance. The NSHΔaroE3ΔgenH_Km strain was analyzed by PCR using the DNA primers (SEQ ID NOs: 127 and 128), the primers (SEQ ID NOs: 121 and 124), and the primers for sacB gene confirmation (SEQ ID NOs: 3 and 4), and the results as expected were obtained. Thus, the NSHΔaroE3ΔgenH_Km strain was found to be a transformant resulting from single-crossover homologous recombination in which the pHKPsacB_rhcR_Prhc-rhcE3 plasmid had been introduced into the rhcHMD gene region.

A transformant resulting from single-crossover homologous recombination of the NSHΔaroE3ΔgenH strain was cultured in 1 mL of LB liquid medium for 24 hours, a part of the culture solution was applied to LB agar medium containing 10% sucrose, and culture was conducted therein. Thus, the NSHΔaroE3ΔgenH_rhcE3 strain was obtained. As a result of PCR using the primers (SEQ ID NOs: 127 and 128), substitution of the rhcHMD gene region with the aroE3 gene was detected in the NSHΔaroE3ΔgenH_rhcE3 strain, and the strain was found to be a transformant resulting from double-crossover homologous recombination, as expected.

5. Test for Amino Acid Auxotrophy of NSHΔaroE3_vanE3 Strain and NSHΔaroE3ΔgenH_rhcE3 Strain The NSH strain, the NSHΔaroE3 strain, the NSHΔaroE3_vanE3 strain, and the NSHΔaroE3ΔgenH_rhcE3 strain produced in the manner described above were tested for aromatic amino acid auxotrophy in the manner described below.

The strains were inoculated into CGXII medium for preculture, culture was conducted at 30° C. overnight, and the cultured strains were washed twice and then transferred to CGXII medium for main culture while adjusting OD 600 at about 0.1. Another culture experiment was simultaneously conducted in a medium prepared by adding 17.5 mg/L shikimic acid, 50 mg/L tryptophan, 50 mg/L phenylalanine, and 50 mg/L tyrosine to CGXII medium. The results demonstrate that the NSH strain grew normally in CGXII medium but the NSHΔaroE3 strain grew very slowly. Regarding the NSHΔaroE3_vanE3 strain and the NSHΔaroE3ΔgenH_rhcE3 strain, the growth thereof became slow from the early culture stage to the middle culture stage, and the growth ability thereof was regained at the late culture stage. Also, the NSHΔaroE3_vanE3 strain and the NSHΔaroE3ΔgenH_rhcE3 strain were found to regain the growth ability with the addition of shikimic acid, tryptophan, phenylalanine, and tyrosine to CGXII medium. Thus, the VanR repressor and the RhcR repressor were found to be capable of regulating aroE3 gene expression.

Reference Example 16

Production of Mutant Strain in which rhcR Gene Expression is Directed by nagI Promoter In order to construct a system of regulating aroE3 gene transcription by the RhcR repressor encoded by the rhcR gene, a mutant strain in which rhcR gene expression would be directed by the nagI promoter was produced in the manner described below.

1. Construction of Vector for Substitution of nagIKL Gene Operon Region with rhcR Gene The nagIKL gene operon region of the NSHΔaroE3ΔgenH strain produced above was substituted with the rhcR gene in the manner described below. Thus, a mutant strain in which rhcR gene expression would be directed by the nagI promoter was produced.

In order to amplify the 5' flanking region (nucleotide numbers of the complementary strand: 3,199,996 to 3,200,904) of the nagIKL gene operon region, two types of DNA primers (SEQ ID NOs: 129 and 130) were synthesized. The SbfI restriction enzyme site was introduced into the primer shown in SEQ ID NO: 129. PCR was carried out using chromosome DNA of the NSH strain as a template and the primers prepared above, so as to amplify the 5' flanking region of the nagIKL gene operon region. In order to amplify the 3' flanking region (nucleotide numbers of the complementary strand: 3,196,321 to 3,197,306) of the nagIKL gene operon region, subsequently, two types of DNA primers (SEQ ID NOs: 131 and 132) were synthesized. The SalI restriction enzyme site was introduced into the primer shown in SEQ ID NO: 132.

In order to amplify the rhcR gene, also, the DNA primers (SEQ ID NOs: 133 and 134) were synthesized. Amplified DNA fragments of the 5' flanking region of the nagIKL gene operon region and the rhcR gene as templates were amplified via overlap PCR using the DNA primers (SEQ ID NOs: 133 and 134). Amplified DNA fragments of the 3' flanking region and the rhcR gene as templates were amplified via overlap PCR using the DNA primers (SEQ ID NOs: 132 and 133). The amplified DNA fragments were digested with restriction enzymes, SbfI in combination with AvrII or AvrII in combination with SalI, and the fragments were introduced into a site between the SbfI site and the SalI site in the multicloning site of the pHKPsacB1 plasmid (see Reference Example 2). Thus, the pHKPsacB_Pnag-rhcR plasmid was obtained.

2. Production of Mutant Strain in which rhcR Gene Expression is Directed by nagI Promoter Through a transformation technique via electroporation, the pHKPsacB_Pnag-rhcR plasmid was introduced into the NSHΔaroE3ΔgenH_rhcE3 strain, and the NSHΔaroE3ΔgenH_rhcE3_Km strain was selected on the basis of kanamycin resistance. The NSHΔaroE3ΔgenH_rhcE3_Km strain was analyzed by PCR using the DNA primers (SEQ ID NOs: 135 and 136), the primers (SEQ ID NOs: 129 and 132), and the primers for sacB gene confirmation (SEQ ID NOs: 3 and 4), and the results as expected were obtained. Thus, the NSHΔaroE3ΔgenH_rhcE3_Km strain was found to be a transformant resulting from single-crossover homologous recombination in which the pHKPsacB_Pnag-rhcR plasmid had been introduced into the nagIKL gene operon region.

A transformant resulting from single-crossover homologous recombination of the NSHΔaroE3ΔgenH_rhcE3 strain was cultured in 1 mL of LB liquid medium for 24 hours, a part of the culture solution was applied to LB agar medium containing 10% sucrose, and culture was conducted therein. Thus, the Pnag-rhcR strain was obtained. As a result of PCR using the primers (SEQ ID NOs: 135 and 136), substitution of the nagIKL gene region with the rhcR gene was detected in the Pnag-rhcR strain, and the strain was found to be a transformant resulting from double-crossover homologous recombination, as expected.

Reference Example 17

Production of Pnag-qsuB-rhcR Strain Producing Protocatechuic Acid in which qsuB and rhcR Gene Expression is Directed by nagI Promoter A mutant strain in which the qsuB gene had been introduced under a control of of the nagI promoter of the Pnag-rhcR strain was produced in the manner described below.

1. Construction of Plasmid for Insertion of qsuB Gene into Downstream of nagI Promoter In order to amplify the 5' flanking region (nucleotide numbers: 3,199,996 to 3,200,904) of the region of qsuB gene insertion, two types of DNA primers (SEQ ID NOs: 137 and 138) were synthesized. In order to amplify the 3' flanking region (nucleotide numbers: 3,198,925 to 3,199,995; this region has been substituted with the rhcR gene) of the region of qsuB gene insertion, also, two types of DNA primers (SEQ ID NOs: 139 and 140) were synthesized. The primers shown in SEQ ID NOs: 137 and 140 each comprise the SbfI and SphI restriction enzyme sites. PCR was carried out using chromosome DNA of the Pnag-rhcR strain (Reference Example 16) as a template and the primers prepared above, so as to amplify the 5' flanking region and the 3' flanking region of the region of qsuB gene insertion. In order to amplify the qsuB gene, further, two types of DNA primers (SEQ ID NOs: 141 and 142) were synthesized. PCR was carried out using chromosome DNA of the HT23 strain (Reference Example 3) as a template and the primers prepared above, so as to amplify the qsuB gene region. Amplified DNA of the 5' flanking region of the region of qsuB gene insertion and amplified DNA of the qsuB gene region thus obtained were mixed with each other. The resulting mixture as a template was amplified via overlap PCR using the primers (SEQ ID NOs: 137 and 142), and the resultant was then digested with the SbfI and XhoI restriction enzymes. Thus, a DNA fragment cleaved with the SbfI site in the primer (SEQ ID NO: 137) and the XhoI site in the qsuB gene was obtained. Also, amplified DNA of the qsuB gene region was mixed with amplified DNA of the 3' flanking region of the region of qsuB gene insertion. The resulting mixture as a template was amplified via overlap PCR using the DNA primers (SEQ ID NOs: 140 and 141), and the resultant was then digested with the XhoI and SphI restriction enzymes. Thus, a DNA fragment cleaved with the XhoI site in the qsuB gene and the SphI site in the primer (SEQ ID NO: 140) was obtained. These 2 types of DNA fragments were introduced into a site between the SbfI site and the SphI site in the multicloning site of the pHKPsacB1 plasmid (see Reference Example 2). Thus, the pHKPsacB_Pnag-qsuB-rhcR plasmid was obtained.

2. Production of Mutant Strain in which qsuB and rhcR Gene Expression is Directed by nagI Promoter Through a transformation technique via electroporation, the pHKPsacB_Pnag-qsuB-rhcR plasmid was introduced into the Pnag-rhcR strain, and the kanamycin-resistant Pnag-rhcR_Km strain was obtained. In order to analyze the Pnag-rhcR_Km strain by PCR, subsequently, the primer identical to the upstream sequence of the 5' flanking region (SEQ ID NO: 143) and the primer identical to the downstream sequence of the 3' flanking region (SEQ ID NO: 144) of the region of qsuB gene insertion were synthesized. The Pnag-rhcR_Km strain was then analyzed by PCR using the primers (SEQ ID NOs: 137 and 140). The results as expected were obtained via PCR analysis using either set of primers. Thus, the Pnag-rhcRKm strain was found to be a transformant resulting from single-crossover homologous recombination in which the pHKPsacB_Pnag-qsuB-rhcR plasmid had been introduced into a downstream region of the nagI promoter.

The Pnag-rhcR_Km strain was cultured in 1 mL of LB liquid medium for 24 hours, a part of the culture solution was applied to LB agar medium containing 10% sucrose, and culture was conducted therein. Thus, the Pnag-qsuB-rhcR strain was obtained. As a result of PCR conducted with the use of the primers (SEQ ID NOs: 143 and 144), the strain was found to be a transformant resulting from double-crossover homologous recombination in which the qsuB gene had been introduced into a downstream region of the nagI promoter.

The invention claimed is:

1. A genetically-modified prokaryotic organism comprising features (a) to (d) below:

(a) activity of at least one enzyme necessary for the production of chorismic acid selected from 3-deoxy-D-arabino-heptulosonate 7-phosphate synthase, phosphoenolpyruvic acid synthetase, phosphoenolpyruvic acid carboxykinase, transketolase, and transaldolase;

is enhanced compared with that of a corresponding wild-type organism;

(b) activity of a first chorismic acid mutase is lost or reduced by mutation to a translation region or promoter of the gene encoding the first chorismic acid mutase compared with that of a corresponding wild-type organism;

(c) a van A, rhcH, or pcaI gene promoter is functionally linked to a gene encoding a second chorismic acid mutase, and (d) a benA gene promoter or a nagI gene promoter is functionally linked to a gene encoding vanR, rhcR, or pcaR.

2. The prokaryotic organism of claim 1, wherein activity of one or more metabolic enzymes that use prephenic acid, anthranilic acid, phenylpyruvic acid, 4-hydroxyphenylpyruvic acid, or arogenic acid as a substrate is lost or reduced compared with that of a corresponding wild-type organism.

3. The prokaryotic organism of claim 1, wherein the prokaryotic organism expresses vanR, rhcR or pcaR and the activity of vanR, rhcR or pcaR is repressed by exposure to ferulic acid, vanillic acid, vanillin, resorcinol, 4-hydroxybenzoic acid, and/or 2,4-dihydroxybenzoic acid compared with that of a corresponding wild-type organism.

4. The prokaryotic organism of claim 1, wherein the gene encoding vanR, rhcR, or pcaR is from the *Corynebacterium glutamicum* ATCC13032 strain.

5. The prokaryotic organism of claim 1, wherein the vanA, rhcH, or pcaI gene promoter functionally linked to the gene encoding the second chorismic acid mutase is from the *Corynebacterium glutamicum* ATCC13032 strain.

6. A method for producing chorismic acid comprising culturing the genetically-modified prokaryotic organism of claim 1, wherein the genetically-modified prokaryotic organism expresses vanR, rhcR, or pcaR.

7. A method for producing chorismic acid comprising culturing the genetically-modified prokaryotic organism of claim 1, wherein the genetically-modified prokaryotic organism expresses vanR, rhcR, or pcaR in response to activation of the benA gene promoter or nagI gene promoter by exposure to 3-hydroxybenzoic acid or benzoic acid.

8. A method for producing chorismic acid comprising culturing the genetically-modified prokaryotic organism of claim 1, wherein the genetically-modified prokaryotic organism expresses vanR, rhcR, or pcaR in response to activation of the benA gene promoter or nagI gene promoter but the second chorismic acid mutase is still expressed by one of the following:

reducing the culture temperature to a level at which vanR, rhcR, or pcaR are inhibited, or adding ferulic acid, vanillic acid, vanillin, resorcinol, 2,4-dihydroxybenzoic acid, or 4-hydroxybenzoic acid in amounts that inhibit vanR, rhcR, or pcaR compared with that of a corresponding wild-type organism.

9. The prokaryotic organism of claim 1, which is *Corynebacterium glutamicum* or *Escherichia coli*.

* * * * *

SEQUENCE LISTING

<160> NUMBER OF SEQ ID NOS: 144

<210> SEQ ID NO 1
<211> LENGTH: 27
<212> TYPE: DNA
<213> ORGANISM: Artificial Sequence
<220> FEATURE:
<223> OTHER INFORMATION: Synthetic DNA

<400> SEQUENCE: 1
catgggatcc tctagatctg acctgca                                           27

<210> SEQ ID NO 2
<211> LENGTH: 27
<212> TYPE: DNA
<213> ORGANISM: Artificial Sequence
<220> FEATURE:
<223> OTHER INFORMATION: Synthetic DNA

<400> SEQUENCE: 2
ggtcagatct agaggatccc atggtac                                           27

<210> SEQ ID NO 3
<211> LENGTH: 36
<212> TYPE: DNA
<213> ORGANISM: Artificial Sequence
<220> FEATURE:
<223> OTHER INFORMATION: Synthetic DNA

<400> SEQUENCE: 3
aagcttaaat gaacatcaaa aagtttgcaa aacaag                                 36

<210> SEQ ID NO 4
<211> LENGTH: 30
<212> TYPE: DNA
<213> ORGANISM: Artificial Sequence
<220> FEATURE:
<223> OTHER INFORMATION: Synthetic DNA

<400> SEQUENCE: 4 gcgttttat ttgttaactg ttaattgtcc                                         30

<210> SEQ ID NO 5
<211> LENGTH: 45
<212> TYPE: DNA
<213> ORGANISM: Artificial Sequence
<220> FEATURE:
<223> OTHER INFORMATION: Synthetic DNA

<400> SEQUENCE: 5
ttcgatttat tcaacaaagc cacgttgtgt ctcaaaatct ctgat                       45

<210> SEQ ID NO 6
<211> LENGTH: 42
<212> TYPE: DNA
<213> ORGANISM: Artificial Sequence
<220> FEATURE:
<223> OTHER INFORMATION: Synthetic DNA

<400> SEQUENCE: 6
gttacattgc acaagataaa aatatatcat catgaacaat aa                          42

<210> SEQ ID NO 7
<211> LENGTH: 40
<212> TYPE: DNA
<213> ORGANISM: Artificial Sequence

```
<220> FEATURE:
<223> OTHER INFORMATION: Synthetic DNA

<400> SEQUENCE: 7
aactgtctgc ttacataaac agtaatacaa ggagctcaca                           40

<210> SEQ ID NO 8
<211> LENGTH: 42
<212> TYPE: DNA
<213> ORGANISM: Artificial Sequence
<220> FEATURE:
<223> OTHER INFORMATION: Synthetic DNA

<400> SEQUENCE: 8
catgactatc aacaaattgg aagcttaaat gtggtagcat ga                        42

<210> SEQ ID NO 9
<211> LENGTH: 41
<212> TYPE: DNA
<213> ORGANISM: Artificial Sequence
<220> FEATURE:
<223> OTHER INFORMATION: Synthetic DNA

<400> SEQUENCE: 9
agattttgag acacaacgtg gctttgttga ataaatcgaa a                         41

<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
tcatgatgat atattttat cttgtgcaat gtaacatcag                            40

<210> SEQ ID NO 11
<211> LENGTH: 41
<212> TYPE: DNA
<213> ORGANISM: Artificial Sequence
<220> FEATURE:
<223> OTHER INFORMATION: Synthetic DNA

<400> SEQUENCE: 11
ctccttgtat tactgtttat gtaagcagac agttttattg t                         41

<210> SEQ ID NO 12
<211> LENGTH: 47
<212> TYPE: DNA
<213> ORGANISM: Artificial Sequence
<220> FEATURE:
<223> OTHER INFORMATION: Synthetic DNA

<400> SEQUENCE: 12
catgctacca catttaagct tccaatttgt tgatagtcat gtgtgag                   47

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13
gcattgacag aggcgaagaa tg                                              22
```

<210> SEQ ID NO 14
<211> LENGTH: 32
<212> TYPE: DNA
<213> ORGANISM: Artificial Sequence
<220> FEATURE:
<223> OTHER INFORMATION: Synthetic DNA

<400> SEQUENCE: 14
ctcgagtgtg tctattacac aggtaccgat gg                        32

<210> SEQ ID NO 15
<211> LENGTH: 31
<212> TYPE: DNA
<213> ORGANISM: Artificial Sequence
<220> FEATURE:
<223> OTHER INFORMATION: Synthetic DNA

<400> SEQUENCE: 15
ctcgagccac caccaaaaaa catacaaaca c                         31

<210> SEQ ID NO 16
<211> LENGTH: 27
<212> TYPE: DNA
<213> ORGANISM: Artificial Sequence
<220> FEATURE:
<223> OTHER INFORMATION: Synthetic DNA

<400> SEQUENCE: 16
agcagacaat gaaatcgtct ctgtaga                              27

<210> SEQ ID NO 17
<211> LENGTH: 32
<212> TYPE: DNA
<213> ORGANISM: Artificial Sequence
<220> FEATURE:
<223> OTHER INFORMATION: Synthetic DNA

<400> SEQUENCE: 17
ttgaattcaa tccagagagt cacatcaact tc                        32

<210> SEQ ID NO 18
<211> LENGTH: 28
<212> TYPE: DNA
<213> ORGANISM: Artificial Sequence
<220> FEATURE:
<223> OTHER INFORMATION: Synthetic DNA

<400> SEQUENCE: 18
ataacgcgtg atgattgagg ccgttgac                             28

<210> SEQ ID NO 19
<211> LENGTH: 31
<212> TYPE: DNA
<213> ORGANISM: Artificial Sequence
<220> FEATURE:
<223> OTHER INFORMATION: Synthetic DNA

<400> SEQUENCE: 19
ataacgcgta cccgatcttt atactccgac c                         31

<210> SEQ ID NO 20
<211> LENGTH: 25
<212> TYPE: DNA
<213> ORGANISM: Artificial Sequence
<220> FEATURE:
<223> OTHER INFORMATION: Synthetic DNA

<400> SEQUENCE: 20
aaggatcccg atggtttcct gatcc                                    25

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
tcccgtggaa tcatgaaagc                                          20

<210> SEQ ID NO 22
<211> LENGTH: 36
<212> TYPE: DNA
<213> ORGANISM: Artificial Sequence
<220> FEATURE:
<223> OTHER INFORMATION: Synthetic DNA

<400> SEQUENCE: 22
aagcttaaat gaacatcaaa aagtttgcaa aacaag                        36

<210> SEQ ID NO 23
<211> LENGTH: 46
<212> TYPE: DNA
<213> ORGANISM: Artificial Sequence
<220> FEATURE:
<223> OTHER INFORMATION: Synthetic DNA

<400> SEQUENCE: 23
ttgacgtccg gaccgaaacg atctgttcta aacagccgcc atgagc              46

<210> SEQ ID NO 24
<211> LENGTH: 31
<212> TYPE: DNA
<213> ORGANISM: Artificial Sequence
<220> FEATURE:
<223> OTHER INFORMATION: Synthetic DNA

<400> SEQUENCE: 24
aagcatgcaa gttttcgacg ccgacatcat c                             31

<210> SEQ ID NO 25
<211> LENGTH: 27
<212> TYPE: DNA
<213> ORGANISM: Artificial Sequence
<220> FEATURE:
<223> OTHER INFORMATION: Synthetic DNA

<400> SEQUENCE: 25
catgggatcc tctagatctg acctgca                                  27

<210> SEQ ID NO 26
<211> LENGTH: 27
<212> TYPE: DNA
<213> ORGANISM: Artificial Sequence
<220> FEATURE:
<223> OTHER INFORMATION: Synthetic DNA

<400> SEQUENCE: 26
ggtcagatct agaggatccc atggtac                                  27

<210> SEQ ID NO 27

<210> SEQ ID NO 27
<211> LENGTH: 29
<212> TYPE: DNA
<213> ORGANISM: Artificial Sequence
<220> FEATURE:
<223> OTHER INFORMATION: Synthetic DNA

<400> SEQUENCE: 27
ttgcatgcgt tggcactgac aagcagacc                                    29

<210> SEQ ID NO 28
<211> LENGTH: 28
<212> TYPE: DNA
<213> ORGANISM: Artificial Sequence
<220> FEATURE:
<223> OTHER INFORMATION: Synthetic DNA

<400> SEQUENCE: 28
aatctagaac gctcgtgtca acgaccac                                     28

<210> SEQ ID NO 29
<211> LENGTH: 29
<212> TYPE: DNA
<213> ORGANISM: Artificial Sequence
<220> FEATURE:
<223> OTHER INFORMATION: Synthetic DNA

<400> SEQUENCE: 29
tttctagatg acccactgga ggtgaagtc                                    29

<210> SEQ ID NO 30
<211> LENGTH: 31
<212> TYPE: DNA
<213> ORGANISM: Artificial Sequence
<220> FEATURE:
<223> OTHER INFORMATION: Synthetic DNA

<400> SEQUENCE: 30
ttgtcgaccg tagaaacgcc ctcatcagaa c                                 31

<210> SEQ ID NO 31
<211> LENGTH: 31
<212> TYPE: DNA
<213> ORGANISM: Artificial Sequence
<220> FEATURE:
<223> OTHER INFORMATION: Synthetic DNA

<400> SEQUENCE: 31
aagcatgcaa gttttcgacg ccgacatcat c                                 31

<210> SEQ ID NO 32
<211> LENGTH: 46
<212> TYPE: DNA
<213> ORGANISM: Artificial Sequence
<220> FEATURE:
<223> OTHER INFORMATION: Synthetic DNA

<400> SEQUENCE: 32
ttgacgtccg gaccgaaacg atctgttcta aacagccgcc atgagc                 46

<210> SEQ ID NO 33
<211> LENGTH: 46
<212> TYPE: DNA
<213> ORGANISM: Artificial Sequence
<220> FEATURE:
<223> OTHER INFORMATION: Synthetic DNA

<400> SEQUENCE: 33
aagacgtctc caggaggaca tacaatgagc gaacaacttc agggtg        46

<210> SEQ ID NO 34
<211> LENGTH: 32
<212> TYPE: DNA
<213> ORGANISM: Artificial Sequence
<220> FEATURE:
<223> OTHER INFORMATION: Synthetic DNA

<400> SEQUENCE: 34
aacctgcagg gcgaaaccaa tctgagttcc aa        32

<210> SEQ ID NO 35
<211> LENGTH: 21
<212> TYPE: DNA
<213> ORGANISM: Artificial Sequence
<220> FEATURE:
<223> OTHER INFORMATION: Synthetic DNA

<400> SEQUENCE: 35
ttcggtccga aggaaaacgt c        21

<210> SEQ ID NO 36
<211> LENGTH: 21
<212> TYPE: DNA
<213> ORGANISM: Artificial Sequence
<220> FEATURE:
<223> OTHER INFORMATION: Synthetic DNA

<400> SEQUENCE: 36
cctcctggac ttcgtggtgg c        21

<210> SEQ ID NO 37
<211> LENGTH: 22
<212> TYPE: DNA
<213> ORGANISM: Artificial Sequence
<220> FEATURE:
<223> OTHER INFORMATION: Synthetic DNA

<400> SEQUENCE: 37
ggtgaactcg atgctgtgat gc        22

<210> SEQ ID NO 38
<211> LENGTH: 29
<212> TYPE: DNA
<213> ORGANISM: Artificial Sequence
<220> FEATURE:
<223> OTHER INFORMATION: Synthetic DNA

<400> SEQUENCE: 38
aagcatgcac ctacgccaga agcaattgc        29

<210> SEQ ID NO 39
<211> LENGTH: 47
<212> TYPE: DNA
<213> ORGANISM: Artificial Sequence
<220> FEATURE:
<223> OTHER INFORMATION: Synthetic DNA

<400> SEQUENCE: 39
ttgacgtccg gaccgaaacg atctctaaga gacgcgatcc cttttac        47

<210> SEQ ID NO 40
<211> LENGTH: 47
<212> TYPE: DNA

```
<213> ORGANISM: Artificial Sequence
<220> FEATURE:
<223> OTHER INFORMATION: Synthetic DNA

<400> SEQUENCE: 40
aagacgtctc caggaggaca tacagtgagt tggacagttg atatccc         47

<210> SEQ ID NO 41
<211> LENGTH: 28
<212> TYPE: DNA
<213> ORGANISM: Artificial Sequence
<220> FEATURE:
<223> OTHER INFORMATION: Synthetic DNA

<400> SEQUENCE: 41
ttctcgagct aagagacgcg atcccttt                              28

<210> SEQ ID NO 42
<211> LENGTH: 21
<212> TYPE: DNA
<213> ORGANISM: Artificial Sequence
<220> FEATURE:
<223> OTHER INFORMATION: Synthetic DNA

<400> SEQUENCE: 42
tccacgcaca gattggttag c                                     21

<210> SEQ ID NO 43
<211> LENGTH: 22
<212> TYPE: DNA
<213> ORGANISM: Artificial Sequence
<220> FEATURE:
<223> OTHER INFORMATION: Synthetic DNA

<400> SEQUENCE: 43
gctgacaaca attgttgtca gc                                    22

<210> SEQ ID NO 44
<211> LENGTH: 27
<212> TYPE: DNA
<213> ORGANISM: Artificial Sequence
<220> FEATURE:
<223> OTHER INFORMATION: Synthetic DNA

<400> SEQUENCE: 44
ttgcatgctg attgttgaag gcctgcc                               27

<210> SEQ ID NO 45
<211> LENGTH: 49
<212> TYPE: DNA
<213> ORGANISM: Artificial Sequence
<220> FEATURE:
<223> OTHER INFORMATION: Synthetic DNA

<400> SEQUENCE: 45
ttgacgtccg gaccgaaacg atctttaatc gatttctaga tgatgcaac       49

<210> SEQ ID NO 46
<211> LENGTH: 45
<212> TYPE: DNA
<213> ORGANISM: Artificial Sequence
<220> FEATURE:
<223> OTHER INFORMATION: Synthetic DNA

<400> SEQUENCE: 46
aagacgtctc caggaggaca taatgagc gcagtgcaga ttttc             45
```

<210> SEQ ID NO 47
<211> LENGTH: 34
<212> TYPE: DNA
<213> ORGANISM: Artificial Sequence
<220> FEATURE:
<223> OTHER INFORMATION: Synthetic DNA

<400> SEQUENCE: 47
ttcctgcagg ttagtggctg attgcctcat aagc                    34

<210> SEQ ID NO 48
<211> LENGTH: 23
<212> TYPE: DNA
<213> ORGANISM: Artificial Sequence
<220> FEATURE:
<223> OTHER INFORMATION: Synthetic DNA

<400> SEQUENCE: 48
aagacgctga agaatccatg atc                                23

<210> SEQ ID NO 49
<211> LENGTH: 22
<212> TYPE: DNA
<213> ORGANISM: Artificial Sequence
<220> FEATURE:
<223> OTHER INFORMATION: Synthetic DNA

<400> SEQUENCE: 49
tatcagccaa agccatgttc tc                                 22

<210> SEQ ID NO 50
<211> LENGTH: 30
<212> TYPE: DNA
<213> ORGANISM: Artificial Sequence
<220> FEATURE:
<223> OTHER INFORMATION: Synthetic DNA

<400> SEQUENCE: 50
aagcatgcat gaaacacgtg agtggtctac                         30

<210> SEQ ID NO 51
<211> LENGTH: 46
<212> TYPE: DNA
<213> ORGANISM: Artificial Sequence
<220> FEATURE:
<223> OTHER INFORMATION: Synthetic DNA

<400> SEQUENCE: 51
ttgacgtccg gaccgaaacg atctttaaag gaagcccttt ttggac        46

<210> SEQ ID NO 52
<211> LENGTH: 45
<212> TYPE: DNA
<213> ORGANISM: Artificial Sequence
<220> FEATURE:
<223> OTHER INFORMATION: Synthetic DNA

<400> SEQUENCE: 52
aagacgtctc caggaggaca tacaatgagt tctccagtct cactc         45

<210> SEQ ID NO 53
<211> LENGTH: 31
<212> TYPE: DNA
<213> ORGANISM: Artificial Sequence
<220> FEATURE:

<223> OTHER INFORMATION: Synthetic DNA

<400> SEQUENCE: 53
aacctgcagg acacatgatg gcaacgtgac c                                    31

<210> SEQ ID NO 54
<211> LENGTH: 21
<212> TYPE: DNA
<213> ORGANISM: Artificial Sequence
<220> FEATURE:
<223> OTHER INFORMATION: Synthetic DNA

<400> SEQUENCE: 54
aatcgagttg gtcacctata c                                               21

<210> SEQ ID NO 55
<211> LENGTH: 22
<212> TYPE: DNA
<213> ORGANISM: Artificial Sequence
<220> FEATURE:
<223> OTHER INFORMATION: Synthetic DNA

<400> SEQUENCE: 55
acgtctacat catcacacca gc                                              22

<210> SEQ ID NO 56
<211> LENGTH: 30
<212> TYPE: DNA
<213> ORGANISM: Artificial Sequence
<220> FEATURE:
<223> OTHER INFORMATION: Synthetic DNA

<400> SEQUENCE: 56
ttgcatgctg cggtagatca gttcacgtgc                                      30

<210> SEQ ID NO 57
<211> LENGTH: 21
<212> TYPE: DNA
<213> ORGANISM: Artificial Sequence
<220> FEATURE:
<223> OTHER INFORMATION: Synthetic DNA

<400> SEQUENCE: 57
cgacgtagtt gaccatgaca g                                               21

<210> SEQ ID NO 58
<211> LENGTH: 37
<212> TYPE: DNA
<213> ORGANISM: Artificial Sequence
<220> FEATURE:
<223> OTHER INFORMATION: Synthetic DNA

<400> SEQUENCE: 58
tggtcaacta cgtcgtcatt gctgcggagg agttctc                              37

<210> SEQ ID NO 59
<211> LENGTH: 33
<212> TYPE: DNA
<213> ORGANISM: Artificial Sequence
<220> FEATURE:
<223> OTHER INFORMATION: Synthetic DNA

<400> SEQUENCE: 59
ttcctgcagg tgattacggt gaatgaggtg agc                                  33

```
<210> SEQ ID NO 60
<211> LENGTH: 20
<212> TYPE: DNA
<213> ORGANISM: Artificial Sequence
<220> FEATURE:
<223> OTHER INFORMATION: Synthetic DNA

<400> SEQUENCE: 60
tgctcaggta gcaaggaacc                                              20

<210> SEQ ID NO 61
<211> LENGTH: 23
<212> TYPE: DNA
<213> ORGANISM: Artificial Sequence
<220> FEATURE:
<223> OTHER INFORMATION: Synthetic DNA

<400> SEQUENCE: 61
aagtatctcc ggtatttccg agc                                          23

<210> SEQ ID NO 62
<211> LENGTH: 28
<212> TYPE: DNA
<213> ORGANISM: Artificial Sequence
<220> FEATURE:
<223> OTHER INFORMATION: Synthetic DNA

<400> SEQUENCE: 62
aagcatgcaa ctcagcgttc caaacagc                                     28

<210> SEQ ID NO 63
<211> LENGTH: 20
<212> TYPE: DNA
<213> ORGANISM: Artificial Sequence
<220> FEATURE:
<223> OTHER INFORMATION: Synthetic DNA

<400> SEQUENCE: 63
ggtgagtgat gtgagaaccc                                              20

<210> SEQ ID NO 64
<211> LENGTH: 35
<212> TYPE: DNA
<213> ORGANISM: Artificial Sequence
<220> FEATURE:
<223> OTHER INFORMATION: Synthetic DNA

<400> SEQUENCE: 64
tcacatcact cacctctcag aagaacacta agtcc                             35

<210> SEQ ID NO 65
<211> LENGTH: 31
<212> TYPE: DNA
<213> ORGANISM: Artificial Sequence
<220> FEATURE:
<223> OTHER INFORMATION: Synthetic DNA

<400> SEQUENCE: 65
ttcctgcagg tacatcatcg ttttacacag c                                 31

<210> SEQ ID NO 66
<211> LENGTH: 22
<212> TYPE: DNA
<213> ORGANISM: Artificial Sequence
<220> FEATURE:
<223> OTHER INFORMATION: Synthetic DNA
```

```
<400> SEQUENCE: 66
tctatatcgg tgtagccacc tc                                       22

<210> SEQ ID NO 67
<211> LENGTH: 20
<212> TYPE: DNA
<213> ORGANISM: Artificial Sequence
<220> FEATURE:
<223> OTHER INFORMATION: Synthetic DNA

<400> SEQUENCE: 67
tttcgcagac caatccgaac                                          20

<210> SEQ ID NO 68
<211> LENGTH: 28
<212> TYPE: DNA
<213> ORGANISM: Artificial Sequence
<220> FEATURE:
<223> OTHER INFORMATION: Synthetic DNA

<400> SEQUENCE: 68
aagcatgcac aaggtcacgt tgaagaac                                 28

<210> SEQ ID NO 69
<211> LENGTH: 21
<212> TYPE: DNA
<213> ORGANISM: Artificial Sequence
<220> FEATURE:
<223> OTHER INFORMATION: Synthetic DNA

<400> SEQUENCE: 69
catggtgaac tcctaaagaa c                                        21

<210> SEQ ID NO 70
<211> LENGTH: 20
<212> TYPE: DNA
<213> ORGANISM: Artificial Sequence
<220> FEATURE:
<223> OTHER INFORMATION: Synthetic DNA

<400> SEQUENCE: 70
aggagcctgg catggatatc                                          20

<210> SEQ ID NO 71
<211> LENGTH: 32
<212> TYPE: DNA
<213> ORGANISM: Artificial Sequence
<220> FEATURE:
<223> OTHER INFORMATION: Synthetic DNA

<400> SEQUENCE: 71
ttcctgcagg tgaaggtcat cagtgtgttt cg                            32

<210> SEQ ID NO 72
<211> LENGTH: 36
<212> TYPE: DNA
<213> ORGANISM: Artificial Sequence
<220> FEATURE:
<223> OTHER INFORMATION: Synthetic DNA

<400> SEQUENCE: 72
ctttaggagt tcaccatggg ttctcacatc actcac                        36

<210> SEQ ID NO 73
<211> LENGTH: 36
```

<212> TYPE: DNA
<213> ORGANISM: Artificial Sequence
<220> FEATURE:
<223> OTHER INFORMATION: Synthetic DNA

<400> SEQUENCE: 73
ccatgccagg ctcctttagt gttcttctga gatgcc        36

<210> SEQ ID NO 74
<211> LENGTH: 22
<212> TYPE: DNA
<213> ORGANISM: Artificial Sequence
<220> FEATURE:
<223> OTHER INFORMATION: Synthetic DNA

<400> SEQUENCE: 74
aacctggata agctgctcat gc        22

<210> SEQ ID NO 75
<211> LENGTH: 22
<212> TYPE: DNA
<213> ORGANISM: Artificial Sequence
<220> FEATURE:
<223> OTHER INFORMATION: Synthetic DNA

<400> SEQUENCE: 75
acacaaccat tgatcagcat gc        22

<210> SEQ ID NO 76
<211> LENGTH: 32
<212> TYPE: DNA
<213> ORGANISM: Artificial Sequence
<220> FEATURE:
<223> OTHER INFORMATION: Synthetic DNA

<400> SEQUENCE: 76
aacctgcagg agtccagtgc gatttccgtt tc        32

<210> SEQ ID NO 77
<211> LENGTH: 29
<212> TYPE: DNA
<213> ORGANISM: Artificial Sequence
<220> FEATURE:
<223> OTHER INFORMATION: Synthetic DNA

<400> SEQUENCE: 77
aatctagaaa cagtggcaat ggatgtacg        29

<210> SEQ ID NO 78
<211> LENGTH: 31
<212> TYPE: DNA
<213> ORGANISM: Artificial Sequence
<220> FEATURE:
<223> OTHER INFORMATION: Synthetic DNA

<400> SEQUENCE: 78
aatctagacc aaactagcat cccgaactag c        31

<210> SEQ ID NO 79
<211> LENGTH: 30
<212> TYPE: DNA
<213> ORGANISM: Artificial Sequence
<220> FEATURE:
<223> OTHER INFORMATION: Synthetic DNA

<400> SEQUENCE: 79

```
ttgtcgactg ttgatgacat ctgccagtgc                                    30
```

<210> SEQ ID NO 80
<211> LENGTH: 21
<212> TYPE: DNA
<213> ORGANISM: Artificial Sequence
<220> FEATURE:
<223> OTHER INFORMATION: Synthetic DNA

<400> SEQUENCE: 80

```
atcaggtcgg ttacttggct c                                             21
```

<210> SEQ ID NO 81
<211> LENGTH: 22
<212> TYPE: DNA
<213> ORGANISM: Artificial Sequence
<220> FEATURE:
<223> OTHER INFORMATION: Synthetic DNA

<400> SEQUENCE: 81

```
ttcagtttcg atgggcatgt ac                                            22
```

<210> SEQ ID NO 82
<211> LENGTH: 31
<212> TYPE: DNA
<213> ORGANISM: Artificial Sequence
<220> FEATURE:
<223> OTHER INFORMATION: Synthetic DNA

<400> SEQUENCE: 82

```
aacctgcagg actgattgcg attcctttgt c                                  31
```

<210> SEQ ID NO 83
<211> LENGTH: 25
<212> TYPE: DNA
<213> ORGANISM: Artificial Sequence
<220> FEATURE:
<223> OTHER INFORMATION: Synthetic DNA

<400> SEQUENCE: 83

```
agaatactgt cgttcatatt tttgg                                         25
```

<210> SEQ ID NO 84
<211> LENGTH: 40
<212> TYPE: DNA
<213> ORGANISM: Artificial Sequence
<220> FEATURE:
<223> OTHER INFORMATION: Synthetic DNA

<400> SEQUENCE: 84

```
gaacgacagt attctctaaa agagtcagta aaacctcgac                         40
```

<210> SEQ ID NO 85
<211> LENGTH: 29
<212> TYPE: DNA
<213> ORGANISM: Artificial Sequence
<220> FEATURE:
<223> OTHER INFORMATION: Synthetic DNA

<400> SEQUENCE: 85

```
aactcgagaa atggcagagt gatgtgtcc                                     29
```

<210> SEQ ID NO 86
<211> LENGTH: 20
<212> TYPE: DNA
<213> ORGANISM: Artificial Sequence
<220> FEATURE:
<223> OTHER INFORMATION: Synthetic DNA

<400> SEQUENCE: 86
ttgctggttc cagttgttgc                                                    20

<210> SEQ ID NO 87
<211> LENGTH: 22
<212> TYPE: DNA
<213> ORGANISM: Artificial Sequence
<220> FEATURE:
<223> OTHER INFORMATION: Synthetic DNA

<400> SEQUENCE: 87
acggtcgaat ccaacaggta gc                                                 22

<210> SEQ ID NO 88
<211> LENGTH: 30
<212> TYPE: DNA
<213> ORGANISM: Artificial Sequence
<220> FEATURE:
<223> OTHER INFORMATION: Synthetic DNA

<400> SEQUENCE: 88
ttgtcgactg cagggtcttg atcttgtagc                                         30

<210> SEQ ID NO 89
<211> LENGTH: 24
<212> TYPE: DNA
<213> ORGANISM: Artificial Sequence
<220> FEATURE:
<223> OTHER INFORMATION: Synthetic DNA

<400> SEQUENCE: 89
gtgaacctcc aagagagtga aaag                                               24

<210> SEQ ID NO 90
<211> LENGTH: 22
<212> TYPE: DNA
<213> ORGANISM: Artificial Sequence
<220> FEATURE:
<223> OTHER INFORMATION: Synthetic DNA

<400> SEQUENCE: 90
taacccttgg tcaatcttag gg                                                 22

<210> SEQ ID NO 91
<211> LENGTH: 32
<212> TYPE: DNA
<213> ORGANISM: Artificial Sequence
<220> FEATURE:
<223> OTHER INFORMATION: Synthetic DNA

<400> SEQUENCE: 91
ttcctgcagg tttggatcaa ttgcagcaaa tg                                      32

<210> SEQ ID NO 92
<211> LENGTH: 37
<212> TYPE: DNA
<213> ORGANISM: Artificial Sequence
<220> FEATURE:
<223> OTHER INFORMATION: Synthetic DNA

<400> SEQUENCE: 92
ctcttggagg ttcacatgac tctacgatct gcattac                                 37

<210> SEQ ID NO 93
<211> LENGTH: 35
<212> TYPE: DNA
<213> ORGANISM: Artificial Sequence
<220> FEATURE:
<223> OTHER INFORMATION: Synthetic DNA

<400> SEQUENCE: 93
gattgaccaa gggttaaagg gtatcgagta gtttc                          35

<210> SEQ ID NO 94
<211> LENGTH: 22
<212> TYPE: DNA
<213> ORGANISM: Artificial Sequence
<220> FEATURE:
<223> OTHER INFORMATION: Synthetic DNA

<400> SEQUENCE: 94
atcatgaggg atctggtaag gc                                        22

<210> SEQ ID NO 95
<211> LENGTH: 21
<212> TYPE: DNA
<213> ORGANISM: Artificial Sequence
<220> FEATURE:
<223> OTHER INFORMATION: Synthetic DNA

<400> SEQUENCE: 95
agtcctaccc aacgcatatc c                                         21

<210> SEQ ID NO 96
<211> LENGTH: 37
<212> TYPE: DNA
<213> ORGANISM: Artificial Sequence
<220> FEATURE:
<223> OTHER INFORMATION: Synthetic DNA

<400> SEQUENCE: 96
ctcttggagg ttcacatgcg tacatccatt gccactg                        37

<210> SEQ ID NO 97
<211> LENGTH: 34
<212> TYPE: DNA
<213> ORGANISM: Artificial Sequence
<220> FEATURE:
<223> OTHER INFORMATION: Synthetic DNA

<400> SEQUENCE: 97
gattgaccaa gggttagttt gggattcccc gctc                           34

<210> SEQ ID NO 98
<211> LENGTH: 22
<212> TYPE: DNA
<213> ORGANISM: Artificial Sequence
<220> FEATURE:
<223> OTHER INFORMATION: Synthetic DNA

<400> SEQUENCE: 98
atcatgaggg atctggtaag gc                                        22

<210> SEQ ID NO 99
<211> LENGTH: 21
<212> TYPE: DNA
<213> ORGANISM: Artificial Sequence
<220> FEATURE:
<223> OTHER INFORMATION: Synthetic DNA

<400> SEQUENCE: 99
agtcctaccc aacgcatatc c                                      21

<210> SEQ ID NO 100
<211> LENGTH: 33
<212> TYPE: DNA
<213> ORGANISM: Artificial Sequence
<220> FEATURE:
<223> OTHER INFORMATION: Synthetic DNA

<400> SEQUENCE: 100
ttcctgcagg ttgggtgatc ttgacgatac tgc                         33

<210> SEQ ID NO 101
<211> LENGTH: 39
<212> TYPE: DNA
<213> ORGANISM: Artificial Sequence
<220> FEATURE:
<223> OTHER INFORMATION: Synthetic DNA

<400> SEQUENCE: 101
ggtgcagttt agctattagt tttcgaacac gtccgtatc                   39

<210> SEQ ID NO 102
<211> LENGTH: 37
<212> TYPE: DNA
<213> ORGANISM: Artificial Sequence
<220> FEATURE:
<223> OTHER INFORMATION: Synthetic DNA

<400> SEQUENCE: 102
gaagcaggtt taacgatggg ttctcacatc actcacc                     37

<210> SEQ ID NO 103
<211> LENGTH: 31
<212> TYPE: DNA
<213> ORGANISM: Artificial Sequence
<220> FEATURE:
<223> OTHER INFORMATION: Synthetic DNA

<400> SEQUENCE: 103
ttgcatgctg atatctcgac attgctgtgt c                           31

<210> SEQ ID NO 104
<211> LENGTH: 22
<212> TYPE: DNA
<213> ORGANISM: Artificial Sequence
<220> FEATURE:
<223> OTHER INFORMATION: Synthetic DNA

<400> SEQUENCE: 104
tagctaaact gcaccactta cc                                     22

<210> SEQ ID NO 105
<211> LENGTH: 23
<212> TYPE: DNA
<213> ORGANISM: Artificial Sequence
<220> FEATURE:
<223> OTHER INFORMATION: Synthetic DNA

<400> SEQUENCE: 105
cgttaaacct gcttccttgt tac                                    23

<210> SEQ ID NO 106

<211> LENGTH: 21
<212> TYPE: DNA
<213> ORGANISM: Artificial Sequence
<220> FEATURE:
<223> OTHER INFORMATION: Synthetic DNA

<400> SEQUENCE: 106
ttggttggaa gatcagacct g                                             21

<210> SEQ ID NO 107
<211> LENGTH: 21
<212> TYPE: DNA
<213> ORGANISM: Artificial Sequence
<220> FEATURE:
<223> OTHER INFORMATION: Synthetic DNA

<400> SEQUENCE: 107
agtcctaccc aacgcatatc c                                             21

<210> SEQ ID NO 108
<211> LENGTH: 33
<212> TYPE: DNA
<213> ORGANISM: Artificial Sequence
<220> FEATURE:
<223> OTHER INFORMATION: Synthetic DNA

<400> SEQUENCE: 108
ttcctgcagg tgctctactg gttcataggt tgc                                33

<210> SEQ ID NO 109
<211> LENGTH: 37
<212> TYPE: DNA
<213> ORGANISM: Artificial Sequence
<220> FEATURE:
<223> OTHER INFORMATION: Synthetic DNA

<400> SEQUENCE: 109
ggtcttaagc acatctgtgt ctattacaca ggtaccg                            37

<210> SEQ ID NO 110
<211> LENGTH: 38
<212> TYPE: DNA
<213> ORGANISM: Artificial Sequence
<220> FEATURE:
<223> OTHER INFORMATION: Synthetic DNA

<400> SEQUENCE: 110
cttcggatct aaacgatacc tcgccaccac caaaaaac                           38

<210> SEQ ID NO 111
<211> LENGTH: 30
<212> TYPE: DNA
<213> ORGANISM: Artificial Sequence
<220> FEATURE:
<223> OTHER INFORMATION: Synthetic DNA

<400> SEQUENCE: 111
ttgtcgactc aggtgagcga catgttgtac                                    30

<210> SEQ ID NO 112
<211> LENGTH: 22
<212> TYPE: DNA
<213> ORGANISM: Artificial Sequence
<220> FEATURE:
<223> OTHER INFORMATION: Synthetic DNA

<400> SEQUENCE: 112
atcgtttaga tccgaaggaa aa                                          22

<210> SEQ ID NO 113
<211> LENGTH: 38
<212> TYPE: DNA
<213> ORGANISM: Artificial Sequence
<220> FEATURE:
<223> OTHER INFORMATION: Synthetic DNA

<400> SEQUENCE: 113
aagtccagga ggacatacaa tgaccacctt gacgctgt                         38

<210> SEQ ID NO 114
<211> LENGTH: 23
<212> TYPE: DNA
<213> ORGANISM: Artificial Sequence
<220> FEATURE:
<223> OTHER INFORMATION: Synthetic DNA

<400> SEQUENCE: 114
gatgtgctta agacccttttg tac                                        23

<210> SEQ ID NO 115
<211> LENGTH: 21
<212> TYPE: DNA
<213> ORGANISM: Artificial Sequence
<220> FEATURE:
<223> OTHER INFORMATION: Synthetic DNA

<400> SEQUENCE: 115
atcttgtcga aacggtgacg c                                           21

<210> SEQ ID NO 116
<211> LENGTH: 23
<212> TYPE: DNA
<213> ORGANISM: Artificial Sequence
<220> FEATURE:
<223> OTHER INFORMATION: Synthetic DNA

<400> SEQUENCE: 116
acgaggggat aaggtgtttc tgc                                         23

<210> SEQ ID NO 117
<211> LENGTH: 27
<212> TYPE: DNA
<213> ORGANISM: Artificial Sequence
<220> FEATURE:
<223> OTHER INFORMATION: Synthetic DNA

<400> SEQUENCE: 117
aaggatcctg tgcatttgct ccaaacc                                     27

<210> SEQ ID NO 118
<211> LENGTH: 28
<212> TYPE: DNA
<213> ORGANISM: Artificial Sequence
<220> FEATURE:
<223> OTHER INFORMATION: Synthetic DNA

<400> SEQUENCE: 118
aacctgcagg ttgaaaaagg gggttagc                                    28

<210> SEQ ID NO 119
<211> LENGTH: 29
<212> TYPE: DNA

```
<213> ORGANISM: Artificial Sequence
<220> FEATURE:
<223> OTHER INFORMATION: Synthetic DNA

<400> SEQUENCE: 119
aacctgcagg agcttgaggt attggaacc                                    29

<210> SEQ ID NO 120
<211> LENGTH: 25
<212> TYPE: DNA
<213> ORGANISM: Artificial Sequence
<220> FEATURE:
<223> OTHER INFORMATION: Synthetic DNA

<400> SEQUENCE: 120
aagtcgacaa aaacatgctc cctgc                                        25

<210> SEQ ID NO 121
<211> LENGTH: 33
<212> TYPE: DNA
<213> ORGANISM: Artificial Sequence
<220> FEATURE:
<223> OTHER INFORMATION: Synthetic DNA

<400> SEQUENCE: 121
ttcctgcagg agctcatcaa catagaacgc gac                               33

<210> SEQ ID NO 122
<211> LENGTH: 29
<212> TYPE: DNA
<213> ORGANISM: Artificial Sequence
<220> FEATURE:
<223> OTHER INFORMATION: Synthetic DNA

<400> SEQUENCE: 122
aaccatggga tctaacccctt cttgaatag                                   29

<210> SEQ ID NO 123
<211> LENGTH: 25
<212> TYPE: DNA
<213> ORGANISM: Artificial Sequence
<220> FEATURE:
<223> OTHER INFORMATION: Synthetic DNA

<400> SEQUENCE: 123
ttccatgggt tctcacatca ctcac                                        25

<210> SEQ ID NO 124
<211> LENGTH: 37
<212> TYPE: DNA
<213> ORGANISM: Artificial Sequence
<220> FEATURE:
<223> OTHER INFORMATION: Synthetic DNA

<400> SEQUENCE: 124
ctacttagac attgccttag tgttcttctg agatgcc                           37

<210> SEQ ID NO 125
<211> LENGTH: 25
<212> TYPE: DNA
<213> ORGANISM: Artificial Sequence
<220> FEATURE:
<223> OTHER INFORMATION: Synthetic DNA

<400> SEQUENCE: 125
ttccatgggt tctcacatca ctcac                                        25
```

<210> SEQ ID NO 126
<211> LENGTH: 37
<212> TYPE: DNA
<213> ORGANISM: Artificial Sequence
<220> FEATURE:
<223> OTHER INFORMATION: Synthetic DNA

<400> SEQUENCE: 126
ctacttagac attgccttag tgttcttctg agatgcc                              37

<210> SEQ ID NO 127
<211> LENGTH: 21
<212> TYPE: DNA
<213> ORGANISM: Artificial Sequence
<220> FEATURE:
<223> OTHER INFORMATION: Synthetic DNA

<400> SEQUENCE: 127
agagcgttct tgacaacctg c                                               21

<210> SEQ ID NO 128
<211> LENGTH: 21
<212> TYPE: DNA
<213> ORGANISM: Artificial Sequence
<220> FEATURE:
<223> OTHER INFORMATION: Synthetic DNA

<400> SEQUENCE: 128
ttggcaacca tcgtgatggt c                                               21

<210> SEQ ID NO 129
<211> LENGTH: 31
<212> TYPE: DNA
<213> ORGANISM: Artificial Sequence
<220> FEATURE:
<223> OTHER INFORMATION: Synthetic DNA

<400> SEQUENCE: 129
aacctgcagg cgtgactctg gaagtttgac c                                    31

<210> SEQ ID NO 130
<211> LENGTH: 20
<212> TYPE: DNA
<213> ORGANISM: Artificial Sequence
<220> FEATURE:
<223> OTHER INFORMATION: Synthetic DNA

<400> SEQUENCE: 130
tgttggagtc ctcctttacg                                                 20

<210> SEQ ID NO 131
<211> LENGTH: 23
<212> TYPE: DNA
<213> ORGANISM: Artificial Sequence
<220> FEATURE:
<223> OTHER INFORMATION: Synthetic DNA

<400> SEQUENCE: 131
ctggctgtag tttccacaca ttc                                             23

<210> SEQ ID NO 132
<211> LENGTH: 28
<212> TYPE: DNA
<213> ORGANISM: Artificial Sequence
<220> FEATURE:

<223> OTHER INFORMATION: Synthetic DNA

<400> SEQUENCE: 132
tagtcgacat catcttgccg ctgattgc                                    28

<210> SEQ ID NO 133
<211> LENGTH: 32
<212> TYPE: DNA
<213> ORGANISM: Artificial Sequence
<220> FEATURE:
<223> OTHER INFORMATION: Synthetic DNA

<400> SEQUENCE: 133
ggaggactcc aacaatgccc acgccttcgc ag                               32

<210> SEQ ID NO 134
<211> LENGTH: 34
<212> TYPE: DNA
<213> ORGANISM: Artificial Sequence
<220> FEATURE:
<223> OTHER INFORMATION: Synthetic DNA

<400> SEQUENCE: 134
ggaaactaca gccagttact gcggtttgac tggg                             34

<210> SEQ ID NO 135
<211> LENGTH: 22
<212> TYPE: DNA
<213> ORGANISM: Artificial Sequence
<220> FEATURE:
<223> OTHER INFORMATION: Synthetic DNA

<400> SEQUENCE: 135
tgtcgacatt gcattgcagc tc                                          22

<210> SEQ ID NO 136
<211> LENGTH: 21
<212> TYPE: DNA
<213> ORGANISM: Artificial Sequence
<220> FEATURE:
<223> OTHER INFORMATION: Synthetic DNA

<400> SEQUENCE: 136 acactttga cactgtggtg c                                            21

<210> SEQ ID NO 137
<211> LENGTH: 31
<212> TYPE: DNA
<213> ORGANISM: Artificial Sequence
<220> FEATURE:
<223> OTHER INFORMATION: Synthetic DNA

<400> SEQUENCE: 137
aacctgcagg cgtgactctg gaagtttgac c                                31

<210> SEQ ID NO 138
<211> LENGTH: 20
<212> TYPE: DNA
<213> ORGANISM: Artificial Sequence
<220> FEATURE:
<223> OTHER INFORMATION: Synthetic DNA

<400> SEQUENCE: 138
tgttggagtc ctcctttacg                                             20

```
<210> SEQ ID NO 139
<211> LENGTH: 36
<212> TYPE: DNA
<213> ORGANISM: Artificial Sequence
<220> FEATURE:
<223> OTHER INFORMATION: Synthetic DNA

<400> SEQUENCE: 139
aaaaaaagga tttgattcat gcccacgcct tcgcag                                 36

<210> SEQ ID NO 140
<211> LENGTH: 30
<212> TYPE: DNA
<213> ORGANISM: Artificial Sequence
<220> FEATURE:
<223> OTHER INFORMATION: Synthetic DNA

<400> SEQUENCE: 140
aagcatgcac accttggaac acctagtagc                                        30

<210> SEQ ID NO 141
<211> LENGTH: 36
<212> TYPE: DNA
<213> ORGANISM: Artificial Sequence
<220> FEATURE:
<223> OTHER INFORMATION: Synthetic DNA

<400> SEQUENCE: 141
ggaggactcc aacaatgcgt acatccattg ccactg                                 36

<210> SEQ ID NO 142
<211> LENGTH: 35
<212> TYPE: DNA
<213> ORGANISM: Artificial Sequence
<220> FEATURE:
<223> OTHER INFORMATION: Synthetic DNA

<400> SEQUENCE: 142
caaatccttt ttttattagt ttgggattcc ccgct                                  35

<210> SEQ ID NO 143
<211> LENGTH: 22
<212> TYPE: DNA
<213> ORGANISM: Artificial Sequence
<220> FEATURE:
<223> OTHER INFORMATION: Synthetic DNA

<400> SEQUENCE: 143
tgtcgacatt gcattgcagc tc                                                22

<210> SEQ ID NO 144
<211> LENGTH: 20
<212> TYPE: DNA
<213> ORGANISM: Artificial Sequence
<220> FEATURE:
<223> OTHER INFORMATION: Synthetic DNA

<400> SEQUENCE: 144
atgacgcatt gcgtcatacc                                                   20
```